(12) United States Patent
Briggs et al.

(10) Patent No.: US 11,679,150 B2
(45) Date of Patent: Jun. 20, 2023

(54) MYCOPLASMA BOVIS VACCINE PRODUCT

(71) Applicant: The United States of America, as represented by the Secretary of Agriculture, Washington, DC (US)

(72) Inventors: Robert E Briggs, Boone, IA (US); Fred M Tatum, Nevada, IA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 17/190,182

(22) Filed: Mar. 2, 2021

(65) Prior Publication Data

US 2021/0275660 A1    Sep. 9, 2021

Related U.S. Application Data

(60) Provisional application No. 62/984,700, filed on Mar. 3, 2020.

(51) Int. Cl.
| | | |
|---|---|---|
| *C07K 14/00* | (2006.01) | |
| *A61K 39/102* | (2006.01) | |
| *A61P 31/04* | (2006.01) | |
| *A61K 39/04* | (2006.01) | |
| *A61K 39/00* | (2006.01) | |

(52) U.S. Cl.
CPC ............ *A61K 39/102* (2013.01); *A61K 39/04* (2013.01); *A61P 31/04* (2018.01); *A61K 2039/5256* (2013.01)

(58) Field of Classification Search
CPC .................................................. A61K 39/102
See application file for complete search history.

(56) References Cited

PUBLICATIONS

Beltran et al (The Veterinary Journal vol. 190, pp. 181-183) (Year: 2011).*

* cited by examiner

*Primary Examiner* — Albert M Navarro
(74) *Attorney, Agent, or Firm* — John D. Fado; Maria Restrepo-Hartwig

(57) ABSTRACT

The present invention relates to modified *Mannheimia haemolytica* (*M. haemolytica*) lktCA gene cluster cassettes, compositions comprising such cassettes, methods of using such cassettes and compositions, and kits comprising such cassettes and compositions. Also described herein are *Mycoplasma bovis* (*M. bovis*) protective antigens, compositions comprising such antigens, methods of using such antigens and compositions, and kits comprising such antigens and compositions. Also described herein are modified *M. haemolytica* lktCA gene cluster cassettes engineered to express *M. bovis* protective antigens, compositions comprising such cassettes, methods of using such cassettes and compositions, and kits comprising such cassettes and compositions.

5 Claims, 9 Drawing Sheets

Specification includes a Sequence Listing.

SEQUENCE LISTING

<160> NUMBER OF SEQ ID NOS: 29

<210> SEQ ID NO 1
<211> LENGTH: 4364
<212> TYPE: DNA
<213> ORGANISM: Mannheimia haemolytica

<400> SEQUENCE: 1

| | | | | | |
|---|---|---|---|---|---|
| ttctctttg | ctaaatagtg | ttggtaagta | gtcccatttt | gcacaccaat | cgttttcacc | 60 |
| ttagcaaaat | ctgtatcttt | tttcgcaatg | aaggcagcag | agcttggaaa | gtaaggctcg | 120 |
| ctaaataata | cttgtttctt | acgtggttcc | gtaataccca | tacctgaaat | tgcagcatca | 180 |
| aattgttttt | gttttaggct | ttggattaag | ctatcaaaag | gttggctatg | aatgtacaa | 240 |
| tttgcattca | tctctttaca | gatagcattt | gcaatatcca | catcaaaacc | gataatttct | 300 |
| cccttctctt | cggtcatttc | aaatggagga | tagcttggct | ccatcacaaa | tttgatatct | 360 |
| tgtgcctgcg | cagtaaccac | acacccgaat | aaaagggtca | aaagtgtttt | tttcataaaa | 420 |
| agtccctgtg | ttttcattat | aaggattacc | actttaacgc | agttactttc | ttaaaaaaag | 480 |
| tcttcttttc | ataaagtttg | ttttatgtca | tacaaacaca | tcaaattgag | atgtagtttc | 540 |
| tcaatcctct | tgattcctct | atctcaaaaa | aacaacccaa | aagaaaaaag | aaaagtatat | 600 |
| gttacattaa | tattacaatg | taattatttt | gtttaatttc | cctacatttt | gtataacttt | 660 |
| aaaacactcc | tttttctctt | ctgattatat | aaaagacaaa | aaatacaatt | taagctacaa | 720 |
| aaaacaacaa | aaaacaacaa | aaaacacgac | aataagatcg | agtaatgatt | atattatgtt | 780 |
| ataatttttg | acctaattta | gaataattat | cgagtgcaaa | ttatgaatca | atcttatttt | 840 |
| aacttactag | gaaacattac | ttggctatgg | atgaactcct | ccctccacaa | agaatggagc | 900 |
| tgtgaactac | tagcacgcaa | tgtgattcct | gcaattgaaa | atgaacaata | tatgctactt | 960 |
| atagataacg | gtattccgat | cgcttattgt | agttgggcag | atttaaacct | tgagactgag | 1020 |
| gtgaaatata | ttaaggatat | taattcgtta | acaccagaag | aatggcagtc | tggtgacaga | 1080 |
| cgctggatta | ttgattgggt | agcaccattc | ggacattctc | aattacttta | taaaaaaatg | 1140 |
| tgtcagaaat | accctgatat | gatcgtcaga | tctatacgct | tttatccaaa | gcagaaagaa | 1200 |
| ttaggcaaaa | ttgcctactt | taaggaggt | aaattagata | aaaaaacagc | aaaaaaacgt | 1260 |
| tttgatacat | atcaagaaga | gctggcaaca | gcacttaaaa | atgaatttaa | ttttattaaa | 1320 |
| aaatagaagg | agacatccct | tatgggaact | agacttacaa | ccctatcaaa | tgggctaaaa | 1380 |
| aacactttaa | cggcaaccaa | aagtggctta | cataaagccg | gtcaatcatt | aacccaagcc | 1440 |
| ggcagttctt | taaaaactgg | ggcaaaaaaa | attatcctct | atattcccca | aaattaccaa | 1500 |
| tatgatactg | aacaaggtaa | tggtttacag | gatttagtca | aagcggccga | agagttgggg | 1560 |
| attgaggtac | aaagagaaga | acgcaataat | attgcaacag | ctcaaaccag | tttaggcacg | 1620 |
| attcaaaccg | ctattggctt | aactgagcgt | ggcattgtgt | tatccgctcc | acaaattgat | 1680 |
| aaattgctac | agaaaactaa | agcaggccaa | gcattaggtt | ctgccgaaag | cattgtacaa | 1740 |

```
aatgcaaata aagccaaaac tgtattatct ggcattcaat ctattttagg ctcagtattg    1800
gctggaatgg atttagatga ggccttacag aataacagca accaacatgc tcttgctaaa    1860
gctggcttgg agctaacaaa ttcattaatt gaaaatattg ctaattcagt aaaaacactt    1920
gacgaatttg tgagcaaat tagtcaattt ggttcaaaac tacaaaatat caaaggctta    1980
gggactttag gagacaaact caaaaatatc ggtggacttg ataaagctgg ccttggttta    2040
gatgttatct cagggctatt atcgggcgca acagctgcac ttgtacttgc agataaaaat    2100
gcttcaacag ctaaaaaagt gggtgcgggt tttgaattgg caaaccaagt tgttggtaat    2160
attaccaaag ccgtttcttc ttacatttta gcccaacgtg ttgcagcagg tttatcttca    2220
actgggcctg tggctgcttt aattgcttct actgtttctc ttgcgattag cccattagca    2280
tttgccggta ttgccgataa atttaatcat gcaaaaagtt tagagagtta tgccgaacgc    2340
tttaaaaaat taggctatga cggagataat ttattagcag aatatcagcg gggaacaggg    2400
actattgatg catcggttac tgcaattaat accgcattgg ccgctattgc tggtggtgtg    2460
tctgctgctg cagccggctc ggttattgct tcaccgattg ccttattagt atctgggatt    2520
accggtgtaa tttctacgat tctgcaatat tctaaacaag caatgtttga gcacgttgca    2580
aataaaattc ataacaaaat tgtagaatgg gaaaaaaata atcacggtaa gaactacttt    2640
gaaaatggtt acgatgcccg ttatcttgcg aatttacaag ataatatgaa attcttactg    2700
aacttaaaca aagagttaca ggcagaacgt gtcatcgcta ttactcagca gcaatgggat    2760
aacaacattg gtgatttagc tggtattagc cgtttaggtg aaaaagtcct tagtggtaaa    2820
gcctatgtgg atgcgtttga agaaggcaaa cacattaaag ccgataaatt agtacagttg    2880
gattcggcaa acggtattat tgatgtgagt aattcgggta aagcgaaaac tcagcatatc    2940
ttattcagaa cgccattatt gacgccggga acagagcatc gtgaacgcgt acaaacaggt    3000
aaatatgaat atattaccaa gctcaatatt aaccgtgtag atagctggaa aattacagat    3060
ggtgcagcaa gttctacctt tgatttaact aacgttgttc agcgtattgg tattgaatta    3120
gacaatgctg gaaatgtaac taaaaccaaa gaaacaaaaa ttattgccaa acttggtgaa    3180
ggtgatgaca acgtatttgt tggttctggt acgacggaaa ttgatggcgg tgaaggttac    3240
gaccgagttc actatagccg tggaaactat ggtgctttaa ctattgatgc aaccaaagag    3300
accgagcaag gtagttatac cgtaaatcgt ttcgtagaaa ccggtaaagc actcacgaa    3360 gtgacttcaa cccataccgc attagtgggc aaccgtgaag aaaaaaataga atatcgtcat    3420 agcaataacc agcaccatgc cggttattac accaaagata ccttgaaagc tgttgaagaa    3480
attatcggta catcacataa cgatatcttt aaaggtagta agttcaatga tgcctttaac    3540
ggtggtgatg tgtcgatac tattgacggt aacgacggca atgaccgctt atttggtggt    3600
aaaggcgatg atattctcga tggtggaaat ggtgatgatt ttatcgatgg cggtaaaggc    3660
aacgacctat tacacggtgg caagggcgat gatattttcg ttcaccgtaa aggcgatggt    3720
aatgatatta ttaccgattc tgacggcaat gataaattat cattctctga ttcgaactta    3780
aaagatttaa catttgaaaa agttaaacat aatcttgtca tcacgaatag caaaaaagag    3840
aaagtgacca ttcaaaactg gttccgagag gctgattttg ctaaagaagt gcctaattat    3900
aaagcaacta aagatgagaa aatcgaagaa atcatcggtc aaaatggcga gcggatcacc    3960
tcaaagcaag ttgatgatct tatcgcaaaa ggtaacggca aaattaccca agatgagcta    4020 tcaaagttg ttgataacta tgaattgctc aaacatagca aaaatgtgac aaacagctta    4080
gataagttaa tctcatctgt aagtgcattt acctcgtcta atgattcgag aaatgtatta    4140
```

```
gtggctccaa cttcaatgtt ggatcaaagt ttatcttctc ttcaatttgc tagagcagct    4200
taatttttaa tgattggcaa ctctatattg tttcacacat tatagagttg ccgttttatt    4260
ttataaaagg agacaatatg aagctaacc atcaaaggaa tgatcttggt ttagttgccc     4320
tcactatgtt ggcacaatac cataatattt cgcttaatcc ggaa                    4364

<210> SEQ ID NO 2
<211> LENGTH: 839
<212> TYPE: DNA
<213> ORGANISM: Artificial Sequence
<220> FEATURE:
<223> OTHER INFORMATION: Delta lktCAV4 down replacement arm

<400> SEQUENCE: 2
ggatccttta acggtggtga tggtgtcgat actattgacg gtaacgacgg caatgaccgc      60
ttatttggtg gtaaaggcga tgatattctc gatggtggaa atggtgatga ttttatcgat     120
ggcggtaaag gcaacgacct attacacggt ggcaagggcg atgatatttt cgttcaccgt     180
aaaggcgatg gtaatgatat tattaccgat tctgacggca atgataaatt atcattctct     240
gattcgaact aaaagatttt aacatttgaa aaagttaaac ataatcttgt catcacgaat     300
agcaaaaaag agaaagtgac cattcaaaac tggttccgag aggctgattt tgctaaagaa     360
gtgcctaatt ataaagcaac taaagatgag aaaatcgaag aaatcatcgg tcaaaatggc     420
gagcggatca cctcaaagca agttgatgat cttatcgcaa aaggtaacgg caaaattacc     480
caagatgagc tatcaaaagt tgttgataac tatgaattgc tcaaacatag caaaaatgtg     540
acaaacagct tagataagtt aatctcatct gtaagtgcat ttacctcgtc taatgattcg     600
agaaatgtat tagtggctcc aacttcaatg ttggatcaaa gtttatcttc tcttcaattt     660
gctagagcag cttaattttt aatgattggc aactctatat tgtttcacac attatagagt     720
tgccgtttta ttttataaaa ggagacaata tggaagctaa ccatcaaagg aatgatcttg     780
gtttagttgc cctcactatg ttggcacaat accataatat ttcgcttaat ccggaattc     839

<210> SEQ ID NO 3
<211> LENGTH: 24
<212> TYPE: DNA
<213> ORGANISM: Artificial Sequence
<220> FEATURE:
<223> OTHER INFORMATION: Down arm forward primer TM56

<400> SEQUENCE: 3
aaaggatcct ttaacggtgg tgat                                              24

<210> SEQ ID NO 4
<211> LENGTH: 37
<212> TYPE: DNA
<213> ORGANISM: Artificial Sequence
<220> FEATURE:
<223> OTHER INFORMATION: Down arm reverse primer TM57

<400> SEQUENCE: 4
aaagaattcc ggattaagcg aaatattatg gtattgt                                37

<210> SEQ ID NO 5
<211> LENGTH: 1076
<212> TYPE: DNA
<213> ORGANISM: Artificial Sequence
<220> FEATURE:
<223> OTHER INFORMATION: DeltalktCAV4 up replacement arm
```

<400> SEQUENCE: 5

```
ggatccgaat tctcttttgc taaatagtgt tggtaagtag tcccattttg cacaccaatc      60
gttttcacct tagcaaaatc tgtatctttt ttcgcaatga aggcagcaga gcttggaaag     120
taaggctcgc taaataatac ttgtttctta cgtggttccg taatacccat acctgaaatt     180
gcagcatcaa attgtttttg ttttaggctt tggattaagc tatcaaaagg ttggctatgg     240
aatgtacaat ttgcattcat ctctttacag atagcatttg caatatccac atcaaaaccg     300
ataatttctc ccttctcttc ggtcatttca aatggaggat agcttggctc catcacaaat     360
ttgatatctt gtgcctgcgc agtaaccaca cacccgaata aagggtcaa aagtgttttt      420
ttcataaaaa gtccctgtgt tttcattata aggattacca ctttaacgca gttactttct     480
taaaaaagt cttcttttca taagtttgt tttatgtcat acaaacacat caaattgaga      540
tgtagtttct caatcctctt gattcctcta tctcaaaaaa acacccaaa agaaaaaga      600
aaagtatatg ttacattaat attacaatgt aattattttg tttaatttcc ctacattttg     660
tataacttta aaacactcct ttttctcttc tgattatata aaagacaaaa aatacaattt     720
aagctacaaa aacaacaaa aaacaacaaa aaacacgaca ataagatcga gtaatgatta     780
tattatgtta aatttttga cctaatttag aataattata ggagacatcc cttatgcaat     840
tggtaattac aaatagcaaa aagaaaaag taacaattca aaattggttt cgtgaagcag    900
atttcgctaa agaagttcca aattataaag caacgaagga tgaaaaaatt gaagaaatta    960
ttggacaaaa tggagaacgt attacaagta acaagtaga tgacttaatc gcaaaggta     1020
acggaaaaat tactcaggat gaattatcga aggtggtaga taactatgaa ggatcc       1076
```

<210> SEQ ID NO 6
<211> LENGTH: 810
<212> TYPE: DNA
<213> ORGANISM: Mannheimia haemolytica

<400> SEQUENCE: 6

```
ttctcttttg ctaaatagtg ttggtaagta gtcccatttt gcacaccaat cgttttcacc      60
ttagcaaaat ctgtatcttt ttcgcaatg aaggcagcag agcttggaaa gtaaggctcg     120
ctaaataata cttgtttctt acgtggttcc gtaatacca tacctgaaat tgcagcatca     180
aattgttttt gttttaggct ttggattaag ctatcaaaag gttggctatg gaatgtacaa     240
tttgcattca tctctttaca gatagcattt gcaatatcca catcaaaacc gataatttct     300
cccttctctt cggtcatttc aaatggagga tagcttggct ccatcacaaa tttgatatct     360
tgtgcctgcg cagtaaccac acacccgaat aaagggtca aagtgttt tttcataaaa      420
agtccctgtg ttttcattat aaggattacc actttaacgc agttactttc ttaaaaaag     480
tcttcttttc ataagtttg ttttatgtca tacaaacaca tcaaattgag atgtagtttc     540
tcaatcctct tgattcctct atctcaaaaa acaacccaa agaaaaaag aaagtatat      600
gttacattaa tattacaatg taattatttt gtttaatttc cctacatttt gtataacttt     660
aaaacactcc ttttctcttc tgattatat aaaagacaaa aatacaatt taagctacaa     720
aaacaacaa aaacaacaa aaacacgac aataagatcg agtaatgatt atattatgtt      780
ataatttttg acctaattta gaataattat                                      810
```

<210> SEQ ID NO 7
<211> LENGTH: 15
<212> TYPE: DNA
<213> ORGANISM: Mannheimia haemolytica

<400> SEQUENCE: 7
aaggagacat ccctt                                                      15

<210> SEQ ID NO 8
<211> LENGTH: 240
<212> TYPE: DNA
<213> ORGANISM: Artificial Sequence
<220> FEATURE:
<223> OTHER INFORMATION: Codon-optimized sequence encoding added
      neutralizing epitope

<400> SEQUENCE: 8
caattggtaa ttacaaatag caaaaaagaa aaagtaacaa ttcaaaattg gtttcgtgaa      60
gcagatttcg ctaaagaagt tccaaattat aaagcaacga aggatgaaaa aattgaagaa     120
attattggac aaaatggaga acgtattaca agtaaacaag tagatgactt aatcgcaaaa     180
ggtaacggaa aaattactca ggatgaatta tcgaaggtgg tagataacta tgaaggatcc     240

<210> SEQ ID NO 9
<211> LENGTH: 80
<212> TYPE: PRT
<213> ORGANISM: Artificial Sequence
<220> FEATURE:
<223> OTHER INFORMATION: translation of SEQ ID NO: 8

<400> SEQUENCE: 9

Gln Leu Val Ile Thr Asn Ser Lys Lys Glu Lys Val Thr Ile Gln Asn
1               5                   10                  15

Trp Phe Arg Glu Ala Asp Phe Ala Lys Glu Val Pro Asn Tyr Lys Ala
            20                  25                  30

Thr Lys Asp Glu Lys Ile Glu Glu Ile Ile Gly Gln Asn Gly Glu Arg
        35                  40                  45

Ile Thr Ser Lys Gln Val Asp Asp Leu Ile Ala Lys Gly Asn Gly Lys
    50                  55                  60

Ile Thr Gln Asp Glu Leu Ser Lys Val Val Asp Asn Tyr Glu Gly Ser
65                  70                  75                  80

<210> SEQ ID NO 10
<211> LENGTH: 832
<212> TYPE: DNA
<213> ORGANISM: Mannheimia haemolytica

<400> SEQUENCE: 10
cctttaacgg tggtgatggt gtcgatacta ttgacggtaa cgacggcaat gaccgcttat      60
ttggtggtaa aggcgatgat attctcgatg gtggaaatgg tgatgatttt atcgatggcg     120
gtaaaggcaa cgacctatta cacggtggca agggcgatga tattttcgtt caccgtaaag     180
gcgatggtaa tgatattatt accgattctg acggcaatga taaattatca ttctctgatt     240
cgaacttaaa agatttaaca tttgaaaaag ttaaacataa tcttgtcatc acgaatagca     300
aaaagagaaa agtgaccatt caaaactggt tccgagaggc tgattttgct aaagaagtgc     360
ctaattataa agcaactaaa gatgagaaaa tcgaagaaat catcggtcaa aatggcgagc     420
ggatcaccct caaagcaagtt gatgatctta tcgcaaaagg taacggcaaa attacccaag     480
atgagctatc aaaagttgtt gataactatg aattgctcaa acatagcaaa aatgtgacaa     540
acagcttaga taagttaatc tcatctgtaa gtgcatttac ctcgtctaat gattcgagaa     600
atgtattagt ggctccaact tcaatgttgg atcaaagttt atcttctctt caatttgcta     660
gagcagctta atttttaatg attggcaact ctatattgtt tcacacatta tagagttgcc     720

```
gttttatttt ataaaaggag acaatatgga agctaaccat caaaggaatg atcttggttt      780
agttgccctc actatgttgg cacaatacca taatatttcg cttaatccgg aa              832
```

<210> SEQ ID NO 11
<211> LENGTH: 282
<212> TYPE: PRT
<213> ORGANISM: Mannheimia haemolytica

<400> SEQUENCE: 11

```
Glu Leu Val Ile Thr Asn Ser Lys Lys Glu Lys Val Thr Ile Gln Asn
1               5                   10                  15

Trp Phe Arg Glu Ala Asp Phe Ala Lys Glu Val Pro Asn Tyr Lys Ala
            20                  25                  30

Thr Lys Asp Glu Lys Ile Glu Glu Ile Ile Gly Gln Asn Gly Glu Arg
        35                  40                  45

Ile Thr Ser Lys Gln Val Asp Asp Leu Ile Ala Lys Gly Asn Gly Lys
    50                  55                  60

Ile Thr Gln Asp Glu Leu Ser Lys Val Val Asp Asn Tyr Glu Gly Ser
65                  70                  75                  80

Phe Asn Gly Gly Asp Gly Val Asp Thr Ile Asp Gly Asn Asp Gly Asn
                85                  90                  95

Asp Arg Leu Phe Gly Gly Lys Gly Asp Asp Ile Leu Asp Gly Gly Asn
            100                 105                 110

Gly Asp Asp Phe Ile Asp Gly Gly Lys Gly Asn Asp Leu Leu His Gly
        115                 120                 125

Gly Lys Gly Asp Asp Ile Phe Val His Arg Lys Gly Asp Val Lys Asp
    130                 135                 140

Leu Thr Phe Glu Lys Val Lys His Asn Leu Val Ile Thr Asn Ser Lys
145                 150                 155                 160

Lys Glu Lys Val Thr Ile Gln Asn Trp Phe Arg Glu Ala Asp Phe Ala
                165                 170                 175

Lys Glu Val Pro Asn Tyr Lys Ala Thr Lys Asp Glu Lys Ile Glu Glu
            180                 185                 190

Ile Ile Gly Gln Asn Gly Glu Arg Ile Thr Ser Lys Gln Val Asp Asp
        195                 200                 205

Leu Ile Ala Lys Gly Asn Gly Lys Ile Thr Gln Asp Glu Leu Ser Lys
    210                 215                 220

Val Val Asp Asn Tyr Glu Leu Leu Lys His Ser Lys Asn Val Thr Asn
225                 230                 235                 240

Ser Leu Asp Lys Leu Ile Ser Ser Val Ser Ala Phe Thr Ser Ser Asn
                245                 250                 255

Asp Ser Arg Asn Val Leu Val Ala Pro Thr Ser Met Leu Asp Gln Ser
            260                 265                 270

Leu Ser Ser Leu Gln Phe Ala Arg Ala Ala
        275                 280
```

<210> SEQ ID NO 12
<211> LENGTH: 1903
<212> TYPE: DNA
<213> ORGANISM: Artificial Sequence
<220> FEATURE:
<223> OTHER INFORMATION: DeltalktCAV4 cassette

<400> SEQUENCE: 12

```
gaattctctt tgctaaaata gtgttggtaa gtagtcccat tttgcacacc aatcgttttc      60
accttagcaa aatctgtatc tttttttcgca atgaaggcag cagagcttgg aaagtaaggc   120
```

```
tcgctaaata atacttgttt cttacgtggt tccgtaatac ccatacctga aattgcagca    180
tcaaattgtt tttgttttag gctttggatt aagctatcaa aaggttggct atggaatgta    240
caatttgcat tcatctcttt acagatagca tttgcaatat ccacatcaaa accgataatt    300
tctcccttct cttcggtcat ttcaaatgga ggatagcttg gctccatcac aaatttgata    360
tcttgtgcct gcgcagtaac cacacacccg aataaaaggg tcaaaagtgt tttttttcata   420 aaaagtccct gtgttttcat tataaggatt accactttaa cgcagttact tcttaaaaa    480 aagtcttctt ttcataaagt ttgttttatg tcatacaaac acatcaaatt gagatgtagt    540
ttctcaatcc tcttgattcc tctatctcaa aaaacaacc caaagaaaaa agaaaagta    600 tatgttacat taatattaca atgtaattat tttgtttaat ttccctacat tttgtataac    660
tttaaaacac tccttttct cttctgatta tataaaagac aaaaaataca atttaagcta    720
caaaaaacaa caaaaaacaa caaaaaacac gacaataaga tcgagtaatg attatattat    780
gttataattt ttgacctaat ttagaataat tataggagac atcccttatg caattggtaa    840
ttacaaatag caaaaaagaa aaagtaacaa ttcaaaattg gtttcgtgaa gcagatttcg    900
ctaaagaagt tccaaattat aaagcaacga aggatgaaaa aattgaagaa attattggac    960
aaaatggaga acgtattaca agtaaacaag tagatgactt aatcgcaaaa ggtaacggaa    1020
aaattactca ggatgaatta tcgaaggtgg tagataacta tgaaggatcc tttaacggtg    1080
gtgatggtgt cgatactatt gacggtaacg acggcaatga ccgcttattt ggtggtaaag    1140
gcgatgatat tctcgatggt ggaaatggtg atgatttat cgatggcggt aaaggcaacg    1200
acctattaca cggtggcaag ggcgatgata ttttcgttca ccgtaaaggc gatggtaatg    1260
atattattac cgattctgac ggcaatgata attatcatt ctctgattcg aacttaaaag    1320
atttaacatt tgaaaaagtt aaacataatc ttgtcatcac gaatagcaaa aaagagaaag    1380
tgaccattca aaactggttc cgagaggctg attttgctaa agaagtgcct aattataaag    1440
caactaaaga tgagaaaatc gaagaaatca tcggtcaaaa tggcgagcgg atcacctcaa    1500
agcaagttga tgatcttatc gcaaaaggta acggcaaaat tacccaagat gagctatcaa    1560
aagttgttga taactatgaa ttgctcaaac atagcaaaaa tgtgacaaac agcttagata    1620
agttaatctc atctgtaagt gcatttacct cgtctaatga ttcgagaaat gtattagtgg    1680
ctccaacttc aatgttggat caaagtttat cttctcttca atttgctaga gcagcttaat    1740 tttaatgat tggcaactct atattgtttc acacattata gagttgccgt tttattttat    1800
aaaaggagac aatatggaag ctaaccatca aaggaatgat cttggtttag ttgccctcac    1860
tatgttggca caataccata atatttcgct taatccggaa ttc                     1903
```

<210> SEQ ID NO 13  
<211> LENGTH: 303  
<212> TYPE: PRT  
<213> ORGANISM: Artificial Sequence  
<220> FEATURE:  
<223> OTHER INFORMATION: (translation of 12)

<400> SEQUENCE: 13

Met Gln Leu Val Ile Thr Asn Ser Lys Lys Glu Lys Val Thr Ile Gln  
1               5                   10                  15

Asn Trp Phe Arg Glu Ala Asp Phe Ala Lys Glu Val Pro Asn Tyr Lys  
            20                  25                  30

Ala Thr Lys Asp Glu Lys Ile Glu Glu Ile Ile Gly Gln Asn Gly Glu  
        35                  40                  45

Arg Ile Thr Ser Lys Gln Val Asp Asp Leu Ile Ala Lys Gly Asn Gly
            50                  55                  60

Lys Ile Thr Gln Asp Glu Leu Ser Lys Val Val Asp Asn Tyr Glu Gly
 65                  70                  75                  80

Ser Phe Asn Gly Gly Asp Gly Val Asp Thr Ile Asp Gly Asn Asp Gly
                85                  90                  95

Asn Asp Arg Leu Phe Gly Gly Lys Gly Asp Asp Ile Leu Asp Gly Gly
            100                 105                 110

Asn Gly Asp Asp Phe Ile Asp Gly Gly Lys Gly Asn Asp Leu Leu His
            115                 120                 125

Gly Gly Lys Gly Asp Asp Ile Phe Val His Arg Lys Gly Asp Gly Asn
    130                 135                 140

Asp Ile Ile Thr Asp Ser Asp Gly Asn Asp Lys Leu Ser Phe Ser Asp
145                 150                 155                 160

Ser Asn Leu Lys Asp Leu Thr Phe Glu Lys Val Lys His Asn Leu Val
                165                 170                 175

Ile Thr Asn Ser Lys Lys Glu Lys Val Thr Ile Gln Asn Trp Phe Arg
            180                 185                 190

Glu Ala Asp Phe Ala Lys Glu Val Pro Asn Tyr Lys Ala Thr Lys Asp
            195                 200                 205

Glu Lys Ile Glu Glu Ile Ile Gly Gln Asn Gly Glu Arg Ile Thr Ser
    210                 215                 220

Lys Gln Val Asp Asp Leu Ile Ala Lys Gly Asn Gly Lys Ile Thr Gln
225                 230                 235                 240

Asp Glu Leu Ser Lys Val Val Asp Asn Tyr Glu Leu Leu Lys His Ser
                245                 250                 255

Lys Asn Val Thr Asn Ser Leu Asp Lys Leu Ile Ser Ser Val Ser Ala
            260                 265                 270

Phe Thr Ser Ser Asn Asp Ser Arg Asn Val Leu Val Ala Pro Thr Ser
            275                 280                 285

Met Leu Asp Gln Ser Leu Ser Ser Leu Gln Phe Ala Arg Ala Ala
    290                 295                 300

<210> SEQ ID NO 14
<211> LENGTH: 606
<212> TYPE: DNA
<213> ORGANISM: Artificial Sequence
<220> FEATURE:
<223> OTHER INFORMATION: codon-optimized sequence encoding M. bovis EFTu

<400> SEQUENCE: 14
atgaacgcgg tcgatacatg gattgagaca cctgttaaag atttcgagaa accgttctta      60
atggcggtag aagacgtgtt tacaatttca ggtcgtggca ccgttgcaac aggtcgtgta     120
gaacgtggac gcttaagttt aaatgaggaa gtggagattg taggtttaaa gcccactaaa     180
aaaacagtcg ttacaggtat cgaaatgttt cgcaaaaact aaaagaagc ccaagcagga     240 gataacgcag gtttattatt acgtggagtt gaacgcagtg ccattgaacg tggtcaagta     300
ttagcaaaac cagggagtat cgttcctcat gccgaatttg aagccgccat ttatgcattg     360
acaaaagaag aaggcggacg tcatactccg tttttcgtaa actataaacc tcaatttttat     420 ttccgtacaa cagatgtgac tggtggcctt gagtttgaga aggacgtga atttgtacaa     480 ccgggagaaa atgtcaactt gaaagtaaaa ttaattgcac caatcgccgt agaggaagga     540
acaaaattca gtattcgtga aggtgggcgc acagtaggt atggtagtgt aactaaaatt     600
ttaaag                                                                606

<210> SEQ ID NO 15
<211> LENGTH: 202
<212> TYPE: PRT
<213> ORGANISM: Artificial Sequence
<220> FEATURE:
<223> OTHER INFORMATION: (translation of SEQ ID NO: 14)

<400> SEQUENCE: 15

```
Met Asn Ala Val Asp Thr Trp Ile Glu Thr Pro Val Lys Asp Phe Glu
1               5                   10                  15

Lys Pro Phe Leu Met Ala Val Glu Asp Val Phe Thr Ile Ser Gly Arg
            20                  25                  30

Gly Thr Val Ala Thr Gly Arg Val Glu Arg Gly Arg Leu Ser Leu Asn
        35                  40                  45

Glu Glu Val Glu Ile Val Gly Leu Lys Pro Thr Lys Lys Thr Val Val
    50                  55                  60

Thr Gly Ile Glu Met Phe Arg Lys Asn Leu Lys Glu Ala Gln Ala Gly
65                  70                  75                  80

Asp Asn Ala Gly Leu Leu Leu Arg Gly Val Glu Arg Ser Ala Ile Glu
                85                  90                  95

Arg Gly Gln Val Leu Ala Lys Pro Gly Ser Ile Val Pro His Ala Glu
            100                 105                 110

Phe Glu Ala Ala Ile Tyr Ala Leu Thr Lys Glu Glu Gly Gly Arg His
        115                 120                 125

Thr Pro Phe Phe Val Asn Tyr Lys Pro Gln Phe Tyr Phe Arg Thr Thr
    130                 135                 140

Asp Val Thr Gly Gly Leu Glu Phe Glu Lys Gly Arg Glu Phe Val Gln
145                 150                 155                 160

Pro Gly Glu Asn Val Asn Leu Lys Val Lys Leu Ile Ala Pro Ile Ala
                165                 170                 175

Val Glu Glu Gly Thr Lys Phe Ser Ile Arg Glu Gly Gly Arg Thr Val
            180                 185                 190

Gly Tyr Gly Ser Val Thr Lys Ile Leu Lys
        195                 200
```

<210> SEQ ID NO 16
<211> LENGTH: 683
<212> TYPE: DNA
<213> ORGANISM: Artificial Sequence
<220> FEATURE:
<223> OTHER INFORMATION: Codon-optimized sequence encoding M. bovis DnaK

<400> SEQUENCE: 16

```
ttagtcgatg taaccccttt aactttaggt attgaaacag caggcggcat tgcaacccct      60
ttaatcccac gtaacactcg tattcccatt acaaagtcag aagttttac  aacgtttgaa     120
gataaccaaa gtgaagtaac aattcgtatc gtgcaaggtg aacgtccatt agcgtctgaa     180
aataaattat taggacaatt taacttaggt ggaatccgta tcgcaccccg tggagtacct     240
caaatcgaag tcagtttcaa aatcgatgca aacggcatta cgacagtatt agcaaaagat     300
aaagatacca caaagaaaca atctattaca attaaaaaca gctctaaatt aagtgacgca     360
gaaatcgaag aaatgatcaa agatgcagaa aaaaccgtg  aagcagatgc caaacgtgcc     420
gaagaaatta gtacaattat tcaagcagaa aacttagtaa actcattaga aaaagaaatg     480
aacgaaggta acattgtaat tccagaagaa gaaaaaacta aatcgccga  atatattaaa     540
gaagtaaaag agttaatcaa caataaagat gtagaacaat taaaaagaa  aattgatgaa     600
```

```
ttaaacgcag catataatat ggccaaatca gcagcagcct cagcaaataa agatgatagt    660
agtaattcgg atgaagaaac ttc                                           683
```

<210> SEQ ID NO 17
<211> LENGTH: 228
<212> TYPE: PRT
<213> ORGANISM: Artificial Sequence
<220> FEATURE:
<223> OTHER INFORMATION: (Translation of SEQ ID NO: 16)

<400> SEQUENCE: 17

```
Leu Val Asp Val Thr Pro Leu Thr Leu Gly Ile Glu Thr Ala Gly Gly
1               5                   10                  15

Ile Ala Thr Pro Leu Ile Pro Arg Asn Thr Arg Ile Pro Ile Thr Lys
            20                  25                  30

Ser Glu Val Phe Thr Thr Phe Glu Asp Asn Gln Ser Glu Val Thr Ile
        35                  40                  45

Arg Ile Val Gln Gly Glu Arg Pro Leu Ala Ser Glu Asn Lys Leu Leu
    50                  55                  60

Gly Gln Phe Asn Leu Gly Gly Ile Arg Ile Ala Pro Arg Gly Val Pro
65                  70                  75                  80

Gln Ile Glu Val Ser Phe Lys Ile Asp Ala Asn Gly Ile Thr Thr Val
                85                  90                  95

Leu Ala Lys Asp Lys Asp Thr Asn Lys Glu Gln Ser Ile Thr Ile Lys
            100                 105                 110

Asn Ser Ser Lys Leu Ser Asp Ala Glu Ile Glu Glu Met Ile Lys Asp
        115                 120                 125

Ala Glu Lys Asn Arg Glu Ala Asp Ala Lys Arg Ala Glu Glu Ile Ser
    130                 135                 140

Thr Ile Ile Gln Ala Glu Asn Leu Val Asn Ser Leu Glu Lys Glu Met
145                 150                 155                 160

Asn Glu Gly Asn Ile Val Ile Pro Glu Glu Glu Lys Thr Lys Ile Ala
                165                 170                 175

Glu Tyr Ile Lys Glu Val Lys Glu Leu Ile Asn Asn Lys Asp Val Glu
            180                 185                 190

Gln Leu Lys Lys Lys Ile Asp Glu Leu Asn Ala Ala Tyr Asn Met Ala
        195                 200                 205

Lys Ser Ala Ala Ala Ser Ala Asn Lys Asp Asp Ser Ser Asn Ser Asp
    210                 215                 220

Glu Glu Thr Phe
225
```

<210> SEQ ID NO 18
<211> LENGTH: 1302
<212> TYPE: DNA
<213> ORGANISM: Artificial Sequence
<220> FEATURE:
<223> OTHER INFORMATION: Codon-optimized sequence encoding M. bovis
    EFTu/DnaK chimera

<400> SEQUENCE: 18

```
caattgatga acgcggtcga tacatggatt gagacacctg ttaaagattt cgagaaaccg    60
ttcttaatgg cggtagaaga cgtgtttaca atttcaggtc gtggcaccgt tgcaacaggt    120
cgtgtagaac gtggacgctt aagttttaat gaggaagtgg agattgtagg tttaaagccc    180
actaaaaaaa cagtcgttac aggtatcgaa atgtttcgca aaaacttaaa agaagcccaa    240
gcaggagata acgcaggttt attattacgt ggagttgaac gcagtgccat tgaacgtggt    300
```

```
caagtattag caaaaccagg gagtatcgtt cctcatgccg aatttgaagc cgccatttat    360
gcattgacaa agaagaagg cggacgtcat actccgtttt tcgtaaacta taaacctcaa    420
ttttatttcc gtacaacaga tgtgactggt ggccttgagt ttgagaaagg acgtgaattt    480
gtacaaccgg gagaaaatgt caacttgaaa gtaaaattaa ttgcaccaat cgccgtagag    540
gaaggaacaa aattcagtat tcgtgaaggt gggcgcacag tagggtatgg tagtgtaact    600
aaaattttaa agttagtcga tgtaaccccct ttaactttag gtattgaaac agcaggcggc    660
attgcaaccc ctttaatccc acgtaacact cgtattccca ttacaaagtc agaagttttt    720
acaacgtttg aagataacca aagtgaagta acaattcgta tcgtgcaagg tgaacgtcca    780
ttagcgtctg aaaataaatt attaggacaa tttaacttag gtggaatccg tatcgcaccc    840
cgtggagtac ctcaaatcga agtcagtttc aaaatcgatg caaacggcat tacgacagta    900
ttagcaaaag ataaagatac caacaaagaa caatctatta caattaaaaa cagctctaaa    960
ttaagtgacg cagaaatcga agaaatgatc aaagatgcag aaaaaaaccg tgaagcagat    1020
gccaaacgtg ccgaagaaat tagtacaatt attcaagcag aaaacttagt aaactcatta    1080
gaaaagaaa tgaacgaagg taacattgta attccagaag aagaaaaaac taaaatcgcc    1140
gaatatatta agaagtaaa agagttaatc aacaataaag atgtagaaca attaaaaaag    1200
aaaattgatg aattaaacgc agcatataat atggccaaat cagcagcagc ctcagcaaat    1260
aaagatgata gtagtaattc ggatgaagaa actttcgaat tc                       1302
```

<210> SEQ ID NO 19
<211> LENGTH: 434
<212> TYPE: PRT
<213> ORGANISM: Artificial Sequence
<220> FEATURE:
<223> OTHER INFORMATION: (Translation of SEQ ID NO: 18)

<400> SEQUENCE: 19

```
Gln Leu Met Asn Ala Val Asp Thr Trp Ile Glu Thr Pro Val Lys Asp
1               5                   10                  15

Phe Glu Lys Pro Phe Leu Met Ala Val Glu Asp Val Phe Thr Ile Ser
            20                  25                  30

Gly Arg Gly Thr Val Ala Thr Gly Arg Val Glu Arg Gly Arg Leu Ser
        35                  40                  45

Leu Asn Glu Glu Val Glu Ile Val Gly Leu Lys Pro Thr Lys Lys Thr
    50                  55                  60

Val Val Thr Gly Ile Glu Met Phe Arg Lys Asn Leu Lys Glu Ala Gln
65                  70                  75                  80

Ala Gly Asp Asn Ala Gly Leu Leu Leu Arg Gly Val Glu Arg Ser Ala
                85                  90                  95

Ile Glu Arg Gly Gln Val Leu Ala Lys Pro Gly Ser Ile Val Pro His
            100                 105                 110

Ala Glu Phe Glu Ala Ala Ile Tyr Ala Leu Thr Lys Glu Glu Gly Gly
        115                 120                 125

Arg His Thr Pro Phe Phe Val Asn Tyr Lys Pro Gln Phe Tyr Phe Arg
    130                 135                 140

Thr Thr Asp Val Thr Gly Gly Leu Glu Phe Glu Lys Gly Arg Glu Phe
145                 150                 155                 160

Val Gln Pro Gly Glu Asn Val Asn Leu Lys Val Lys Leu Ile Ala Pro
                165                 170                 175

Ile Ala Val Glu Glu Gly Thr Lys Phe Ser Ile Arg Glu Gly Gly Arg
            180                 185                 190
```

```
Thr Val Gly Tyr Gly Ser Val Thr Lys Ile Leu Lys Leu Val Asp Val
        195                 200                 205

Thr Pro Leu Thr Leu Gly Ile Glu Thr Ala Gly Gly Ile Ala Thr Pro
    210                 215                 220

Leu Ile Pro Arg Asn Thr Arg Ile Pro Ile Thr Lys Ser Glu Val Phe
225                 230                 235                 240

Thr Thr Phe Glu Asp Asn Gln Ser Glu Val Thr Ile Arg Ile Val Gln
                245                 250                 255

Gly Glu Arg Pro Leu Ala Ser Glu Asn Lys Leu Leu Gly Gln Phe Asn
            260                 265                 270

Leu Gly Gly Ile Arg Ile Ala Pro Arg Gly Val Pro Gln Ile Glu Val
        275                 280                 285

Ser Phe Lys Ile Asp Ala Asn Gly Ile Thr Thr Val Leu Ala Lys Asp
    290                 295                 300

Lys Asp Thr Asn Lys Glu Gln Ser Ile Thr Ile Lys Asn Ser Ser Lys
305                 310                 315                 320

Leu Ser Asp Ala Glu Ile Glu Glu Met Ile Lys Asp Ala Glu Lys Asn
                325                 330                 335

Arg Glu Ala Asp Ala Lys Arg Ala Glu Glu Ile Ser Thr Ile Ile Gln
            340                 345                 350

Ala Glu Asn Leu Val Asn Ser Leu Glu Lys Glu Met Asn Glu Gly Asn
        355                 360                 365

Ile Val Ile Pro Glu Glu Glu Lys Thr Lys Ile Ala Glu Tyr Ile Lys
    370                 375                 380

Glu Val Lys Glu Leu Ile Asn Asn Lys Asp Val Glu Gln Leu Lys Lys
385                 390                 395                 400

Lys Ile Asp Glu Leu Asn Ala Ala Tyr Asn Met Ala Lys Ser Ala Ala
                405                 410                 415

Ala Ser Ala Asn Lys Asp Asp Ser Ser Asn Ser Asp Glu Glu Thr Phe
            420                 425                 430

Glu Phe
```

<210> SEQ ID NO 20
<211> LENGTH: 3205
<212> TYPE: DNA
<213> ORGANISM: Artificial Sequence
<220> FEATURE:
<223> OTHER INFORMATION: DeltalktCAV4Mbovis cassette

<400> SEQUENCE: 20

```
ggatccgaat tctcttttgc taaatagtgt tggtaagtag tcccattttg cacaccaatc     60
gttttcacct tagcaaaatc tgtatctttt ttcgcaatga aggcagcaga gcttggaaag    120
taaggctcgc taaataatac ttgtttctta cgtggttccg taatacccat acctgaaatt    180
gcagcatcaa attgtttttg ttttaggctt tggattaagc tatcaaaagg ttggctatgg    240
aatgtacaat ttgcattcat ctctttacag atagcatttg caatatccac atcaaaaccg    300
ataatttctc ccttctcttc ggtcatttca aatggaggat agcttggctc catcacaaat    360
ttgatatctt gtgcctgcgc agtaaccaca cacccgaata aaagggtcaa aagtgttttt    420
ttcataaaaa gtccctgtgt tttcattata aggattacca ctttaacgca gttactttct    480
taaaaaaagt cttcttttca taaagtttgt tttatgtcat acaaacacat caaattgaga    540
tgtagtttct caatcctctt gattcctcta tctcaaaaaa acaacccaaa agaaaaaaga    600
aaagtatatg ttacattaat attacaatgt aattattttg tttaatttcc ctacattttg    660
```

```
tataacttta aaacactcct ttttctcttc tgattatata aaagacaaaa aatacaattt    720
aagctacaaa aaacaacaaa aaacaacaaa aaacacgaca ataagatcga gtaatgatta    780
tattatgtta aattttttga cctaatttag aataattata ggagacatcc cttatgcaat    840
tgatgaacgc ggtcgataca tggattgaga ccctgttaa  agatttcgag aaaccgttct    900
taatggcggt agaagacgtg tttacaattt caggtcgtgg caccgttgca acaggtcgtg    960
tagaacgtgg acgcttaagt ttaaatgagg aagtggagat tgtaggttta aagcccacta   1020
aaaaaacagt cgttacaggt atcgaaatgt ttcgcaaaaa cttaaaagaa gcccaagcag   1080
gagataacgc aggtttatta ttacgtggag ttgaacgcag tgccattgaa cgtggtcaag   1140
tattagcaaa accagggagt atcgttcctc atgccgaatt tgaagccgcc atttatgcat   1200
tgacaaaaga agaaggcgga cgtcatactc cgttttccgt aaactataaa cctcaatttt   1260
atttccgtac aacagatgtg actggtggcc ttgagtttga gaaaggacgt gaatttgtac   1320
aaccgggaga aaatgtcaac ttgaaagtaa aattaattgc accaatcgcc gtagaggaag   1380
gaacaaaatt cagtattcgt gaaggtgggc gcacagtagg gtatggtagt gtaactaaaa   1440
ttttaaagtt agtcgatgta accccttttaa ctttaggtat tgaaacagca ggcggcattg   1500
caacccettt aatcccacgt aacactcgta ttcccattac aaagtcagaa gttttttacaa   1560
cgtttgaaga taaccaaagt gaagtaacaa ttcgtatcgt gcaaggtgaa cgtccattag   1620
cgtctgaaaa taaattatta ggacaattta acttaggtgg aatccgtatc gcaccccgtg   1680
gagtacctca aatcgaagtc agtttcaaaa tcgatgcaaa cggcattacg acagtattag   1740
caaaagataa agataccaac aaagaacaat ctattacaat taaaaacagc tctaaattaa   1800
gtgacgcaga aatcgaagaa atgatcaaag atgcagaaaa aaaccgtgaa gcagatgcca   1860
aacgtgccga gaaaattagt acaattattc aagcagaaaa cttagtaaac tcattagaaa   1920
aagaaatgaa cgaaggtaac attgtaattc cagaagaaga aaaaactaaa atcgccgaat   1980
atattaaaga agtaaaagag ttaatcaaca ataaagatgt agaacaatta aaaaagaaaa   2040
ttgatgaatt aaacgcagca tataatatgg ccaaatcagc agcagcctca gcaaataaag   2100
atgatagtag taattcggat gaagaaactt tcgaattggt aattacaaat agcaaaaaag   2160
aaaaagtaac aattcaaaat tggtttcgtg aagcagattt cgctaaagaa gttccaaatt   2220
ataaagcaac gaaggatgaa aaaattgaag aaattattgg acaaaatgga gaacgtatta   2280
caagtaaaca agtagatgac ttaatcgcaa aaggtaacgg aaaaattact caggatgaat   2340
tatcgaaggt ggtagataac tatgaaggat cctttaacgg tggtgatggt gtcgatacta   2400
ttgacggtaa cgacggcaat gaccgcttat ttggtggtaa aggcgatgat attctcgatg   2460
gtggaaatgg tgatgatttt atcgatggcg gtaaaggcaa cgacctatta cacggtggca   2520
agggcgatga tattttcgtt caccgtaaag gcgatggtaa tgatattatt accgattctg   2580
acggcaatga taaattatca ttctctgatt cgaacttaaa agatttaaca tttgaaaaag   2640
ttaaacataa tcttgtcatc acgaatagca aaaaagagaa agtgaccatt caaaactggt   2700
tccgagaggc tgattttgct aaagaagtgc ctaattataa agcaactaaa gatgagaaaa   2760
tcgaagaaat catcggtcaa aatggcgagc ggatcacctc aaagcaagtt gatgatctta   2820
tcgcaaaagg taacggcaaa attacccaag atgagctatc aaaagttgtt gataactatg   2880
aattgctcaa acatagcaaa aatgtgacaa acagcttaga taagttaatc tcatctgtaa   2940
gtgcatttac ctcgtctaat gattcgagaa atgtattagt ggctccaact tcaatgttgg   3000
atcaaagttt atcttctctt caatttgcta gagcagctta atttttaatg attggcaact   3060
```

```
ctatattgtt tcacacatta tagagttgcc gttttatttt ataaaaggag acaatatgga    3120
agctaaccat caaaggaatg atcttggttt agttgccctc actatgttgg cacaatacca    3180
taatatttcg cttaatccgg aattc                                          3205
```

<210> SEQ ID NO 21
<211> LENGTH: 735
<212> TYPE: PRT
<213> ORGANISM: Artificial Sequence
<220> FEATURE:
<223> OTHER INFORMATION: (Translation of SEQ ID NO: 20)

<400> SEQUENCE: 21

```
Met Gln Leu Met Asn Ala Val Asp Thr Trp Ile Glu Thr Pro Val Lys
1               5                   10                  15

Asp Phe Glu Lys Pro Phe Leu Met Ala Val Glu Asp Val Phe Thr Ile
            20                  25                  30

Ser Gly Arg Gly Thr Val Ala Thr Gly Arg Val Glu Arg Gly Arg Leu
        35                  40                  45

Ser Leu Asn Glu Glu Val Glu Ile Val Gly Leu Lys Pro Thr Lys Lys
    50                  55                  60

Thr Val Val Thr Gly Ile Glu Met Phe Arg Lys Asn Leu Lys Glu Ala
65                  70                  75                  80

Gln Ala Gly Asp Asn Ala Gly Leu Leu Leu Arg Gly Val Glu Arg Ser
                85                  90                  95

Ala Ile Glu Arg Gly Gln Val Leu Ala Lys Pro Gly Ser Ile Val Pro
            100                 105                 110

His Ala Glu Phe Glu Ala Ala Ile Tyr Ala Leu Thr Lys Glu Glu Gly
        115                 120                 125

Gly Arg His Thr Pro Phe Phe Val Asn Tyr Lys Pro Gln Phe Tyr Phe
    130                 135                 140

Arg Thr Thr Asp Val Thr Gly Leu Glu Phe Glu Lys Gly Arg Glu
145                 150                 155                 160

Phe Val Gln Pro Gly Glu Asn Val Asn Leu Lys Val Lys Leu Ile Ala
                165                 170                 175

Pro Ile Ala Val Glu Glu Gly Thr Lys Phe Ser Ile Arg Glu Gly Gly
            180                 185                 190

Arg Thr Val Gly Tyr Gly Ser Val Thr Lys Ile Leu Lys Leu Val Asp
        195                 200                 205

Val Thr Pro Leu Thr Leu Gly Ile Glu Thr Ala Gly Gly Ile Ala Thr
    210                 215                 220

Pro Leu Ile Pro Arg Asn Thr Arg Ile Pro Ile Thr Lys Ser Glu Val
225                 230                 235                 240

Phe Thr Thr Phe Glu Asp Asn Gln Ser Glu Val Thr Ile Arg Ile Val
                245                 250                 255

Gln Gly Glu Arg Pro Leu Ala Ser Glu Asn Lys Leu Leu Gly Gln Phe
            260                 265                 270

Asn Leu Gly Gly Ile Arg Ile Ala Pro Arg Gly Val Pro Gln Ile Glu
        275                 280                 285

Val Ser Phe Lys Ile Asp Ala Asn Gly Ile Thr Thr Val Leu Ala Lys
    290                 295                 300

Asp Lys Asp Thr Asn Lys Glu Gln Ser Ile Thr Ile Lys Asn Ser Ser
305                 310                 315                 320

Lys Leu Ser Asp Ala Glu Ile Glu Glu Met Ile Lys Asp Ala Glu Lys
                325                 330                 335
```

```
Asn Arg Glu Ala Asp Ala Lys Arg Ala Glu Ile Ser Thr Ile Ile
            340                 345                 350

Gln Ala Glu Asn Leu Val Asn Ser Leu Glu Lys Glu Met Asn Glu Gly
            355                 360                 365

Asn Ile Val Ile Pro Glu Glu Lys Thr Lys Ile Ala Glu Tyr Ile
            370                 375                 380

Lys Glu Val Lys Glu Leu Ile Asn Asn Lys Asp Val Glu Gln Leu Lys
385                 390                 395                 400

Lys Lys Ile Asp Glu Leu Asn Ala Ala Tyr Asn Met Ala Lys Ser Ala
                405                 410                 415

Ala Ala Ser Ala Asn Lys Asp Asp Ser Asn Ser Asp Glu Glu Thr
            420                 425                 430

Phe Glu Leu Val Ile Thr Asn Ser Lys Lys Glu Lys Val Thr Ile Gln
            435                 440                 445

Asn Trp Phe Arg Glu Ala Asp Phe Ala Lys Glu Val Pro Asn Tyr Lys
    450                 455                 460

Ala Thr Lys Asp Glu Lys Ile Glu Glu Ile Ile Gly Gln Asn Gly Glu
465                 470                 475                 480

Arg Ile Thr Ser Lys Gln Val Asp Asp Leu Ile Ala Lys Gly Asn Gly
                485                 490                 495

Lys Ile Thr Gln Asp Glu Leu Ser Lys Val Val Asp Asn Tyr Glu Gly
                500                 505                 510

Ser Phe Asn Gly Gly Asp Gly Val Asp Thr Ile Asp Gly Asn Asp Gly
            515                 520                 525

Asn Asp Arg Leu Phe Gly Gly Lys Gly Asp Asp Ile Leu Asp Gly Gly
            530                 535                 540

Asn Gly Asp Asp Phe Ile Asp Gly Gly Lys Gly Asn Asp Leu Leu His
545                 550                 555                 560

Gly Gly Lys Gly Asp Asp Ile Phe Val His Arg Lys Gly Asp Gly Asn
                565                 570                 575

Asp Ile Ile Thr Asp Ser Asp Gly Asn Asp Lys Leu Ser Phe Ser Asp
            580                 585                 590

Ser Asn Leu Lys Asp Leu Thr Phe Glu Lys Val Lys His Asn Leu Val
    595                 600                 605

Ile Thr Asn Ser Lys Lys Glu Lys Val Thr Ile Gln Asn Trp Phe Arg
    610                 615                 620

Glu Ala Asp Phe Ala Lys Glu Val Pro Asn Tyr Lys Ala Thr Lys Asp
625                 630                 635                 640

Glu Lys Ile Glu Glu Ile Ile Gly Gln Asn Gly Glu Arg Ile Thr Ser
                645                 650                 655

Lys Gln Val Asp Asp Leu Ile Ala Lys Gly Asn Gly Lys Ile Thr Gln
                660                 665                 670

Asp Glu Leu Ser Lys Val Val Asp Asn Tyr Glu Leu Leu Lys His Ser
            675                 680                 685

Lys Asn Val Thr Asn Ser Leu Asp Lys Leu Ile Ser Ser Val Ser Ala
            690                 695                 700

Phe Thr Ser Ser Asn Asp Ser Arg Asn Val Leu Val Ala Pro Thr Ser
705                 710                 715                 720

Met Leu Asp Gln Ser Leu Ser Ser Leu Gln Phe Ala Arg Ala Ala
            725                 730                 735
```

```
<210> SEQ ID NO 22
<211> LENGTH: 23
<212> TYPE: DNA
<213> ORGANISM: Artificial Sequence
<220> FEATURE:
<223> OTHER INFORMATION: Primer DeltalktCAV4diagF

<400> SEQUENCE: 22
gttctcaatc ctcttgattc ctc                                              23

<210> SEQ ID NO 23
<211> LENGTH: 24
<212> TYPE: DNA
<213> ORGANISM: Artificial Sequence
<220> FEATURE:
<223> OTHER INFORMATION: Primer DeltalktCAV4diagR

<400> SEQUENCE: 23
gttaccgtca atagtatcga cacc                                             24

<210> SEQ ID NO 24
<211> LENGTH: 24
<212> TYPE: DNA
<213> ORGANISM: Artificial Sequence
<220> FEATURE:
<223> OTHER INFORMATION: Primer MbovispolyF

<400> SEQUENCE: 24
ggagaaaatg tcaacttgaa agta                                             24

<210> SEQ ID NO 25
<211> LENGTH: 23
<212> TYPE: DNA
<213> ORGANISM: Artificial Sequence
<220> FEATURE:
<223> OTHER INFORMATION: Primer MbovispolyR

<400> SEQUENCE: 25
ggattccacc taagttaaat tgt                                              23

<210> SEQ ID NO 26
<211> LENGTH: 20
<212> TYPE: DNA
<213> ORGANISM: Artificial Sequence
<220> FEATURE:
<223> OTHER INFORMATION: Primer MhSt1F

<400> SEQUENCE: 26
acaccaaagc aacagactgc                                                  20

<210> SEQ ID NO 27
<211> LENGTH: 20
<212> TYPE: DNA
<213> ORGANISM: Artificial Sequence
<220> FEATURE:
<223> OTHER INFORMATION: Primer MhSt1R

<400> SEQUENCE: 27
cctgtaaagg catctgccca                                                  20

<210> SEQ ID NO 28
<211> LENGTH: 20
<212> TYPE: DNA
<213> ORGANISM: Artificial Sequence
<220> FEATURE:
<223> OTHER INFORMATION: Primer MhSt6F
```

```
<400> SEQUENCE: 28
ttggtgcttg ggagtatgcc                                               20

<210> SEQ ID NO 29
<211> LENGTH: 20
<212> TYPE: DNA
<213> ORGANISM: Artificial Sequence
<220> FEATURE:
<223> OTHER INFORMATION: Primer MhSt6R

<400> SEQUENCE: 29
atcggaaacg gtttgctgga                                               20
```

MYCOPLASMA BOVIS VACCINE PRODUCT

CROSS-REFERENCE TO RELATED APPLICATIONS

This application claims priority to U.S. Provisional Patent Application No. 62/984,700, filed Mar. 3, 2020. The content of this provisional patent application is hereby expressly incorporated by reference in its entirety.

FIELD OF THE INVENTION

The invention relates to modified *Mannheimia haemolytica* (*M. haemolytica*) lktCA gene cluster cassettes comprising an insertion of a polynucleotide encoding an additional *M. haemolytica* leukotoxin neutralizing epitope. Encompassed by the invention are also modified *M. haemolytica* lktCA gene cluster cassettes expressing a *Mycoplasma bovis* (*M. bovis*) antigen. The invention also concerns Compositions, vectors, and bacterial or fungal strains comprising such modified *M. haemolytica* lktCA gene cluster cassettes. Included in the invention are kits comprising such cassettes, compositions, vectors, and bacterial or fungal strains; and methods of vaccination using such cassettes, compositions, vectors, and bacterial or fungal strains.

SEQUENCE LISTING

The instant application contains a Sequence Listing which has been submitted via EFS-Web as ASCII compliant text file format (.txt), and is hereby incorporated by reference in its entirety. The ASCII file was created on Mar. 2, 2021, is named SequenceListing, and has 44 kilobytes. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

*Mycoplasma bovis* (*M. bovis*) is an important pathogen associated with a relatively broad range of disease manifestations. Prominently due to *M. bovis*, pneumonia, otitis media, polyarthritis, and mastitis result in considerable economic losses to dairy, beef, and bison producers in the United States and abroad. *M. bovis* disease treatment with antimicrobials is often unrewarding, requiring early diagnosis and early drug delivery for efficacy. Yet symptoms of disease are often mild and slowly-progressing, resulting in considerable difficulty in diagnosis, and in treatment delays.

Management practices, including biosecurity, sanitation, and husbandry practices to reduce stress, appear to result in reduced disease losses. Vaccination with experimental or commercial vaccines to prevent *M. bovis*-associated disease has yielded mixed results. Some published trials have shown disease reduction among vaccinated animals, while others have shown no statistical protection. Anecdotally, vaccination with commercial products may result in meaningful reductions of polyarthritis and otitis media. Two *M. bovis* vaccine products, both bacterins (inactivated bacteria), are commercially available in the United States. No commercial *M. bovis* vaccine product appears to be currently available in the European Union.

Use of bacterial vectors as vehicles to deliver recombinant antigens emerged in the late 1990s. Bacteria-based antigen delivery vectors exhibit multiple advantages, such as the possibility to control its intrinsic infectious power, its non-integrative properties, ability to regulate the amount and in vivo localization of the antigen, a potential for multiple vaccine delivery routes, potent stimulation of the innate and adaptive immune systems, and relatively low manufacturing costs. Bacterial vectors most frequently used as vaccine vectors are *Listeria* and *Salmonella*.

U.S. Pat. No. 9,370,561, issued Jun. 21, 2016, discloses the modification of the *M. haemolytica* strain A1 lktCA gene cluster by an in-frame deletion of the nucleotides encoding amino acid 4 of lktC to the nucleotides encoding amino acid 707 of lktA, and replacement of the lktC ribosome binding site (rbs) with an *E. coli* consensus rbs. Electrocompetent *M. haemolytica* cells were transformed with the modified lktCA gene cluster resulting in attenuated bacterium. U.S. Pat. No. 9,370,561 claims a vaccine comprising live, attenuated *M. haemolytica* A1 and A6 strains containing nucleic acid deletions in their respective lktA genes, that provide protective immune response against disease caused by *M. haemolytica* strains A1 and A6.

U.S. Pat. No. 6,331,303, issued Dec. 18, 2001, discloses *P. haemolytica* bacterium which expresses no biologically active leukotoxin, expresses a leukotoxin molecule lacking amino acids 34 to 378, and contains no foreign DNA. In 1999, *P. haemolytica* was renamed as *Mannheimia haemolytica*.

Thus, new methods of controlling *M. bovis* disease are needed. Use of a modified *M. haemolytica* lktCA gene cluster cassette may expedite preparation of *M. bovis* vaccines for such control.

SUMMARY OF THE INVENTION

Provided herein is a modified *M. haemolytica* lktCA gene cluster cassette comprising a polynucleotide fragment encoding an additional leukotoxin neutralizing epitope. This modified *M. haemolytica* lktCA gene cluster cassette encodes two leukotoxin neutralizing epitopes, and is useful for the expression of bacterial or viral antigens. Provided herein is also an *M. bovis* antigen and a modified *M. haemolytica* lktCA gene cluster cassette comprising a polynucleotide fragment encoding an additional leukotoxin neutralizing epitope expressing an *M. bovis* antigen.

In an embodiment, the invention relates to a modified *M. haemolytica* lktCA gene cluster cassette comprising a polynucleotide encoding an additional leukotoxin neutralizing epitope inserted downstream of the native leukotoxin A start codon. In some embodiments of the invention, the modified *M. haemolytica* lktCA gene cluster cassette lacks the leukotoxin C ribosome binding site and coding region. In some embodiments of the invention, the modified *M. haemolytica* lktCA gene cluster cassette lacks leukotoxin A nucleotides encoding amino acids 2 to at least 710.

In some embodiments of the invention, the modified *M. haemolytica* lktCA gene cluster cassette comprises a native leukotoxin promotor polynucleotide fragment; a native leukotoxin A ribosome binding site and start codon polynucleotide fragment; the polynucleotide encoding the added leukotoxin neutralizing epitope; and a polynucleotide encoding at least leukotoxin A amino acids 732 to 953. In some embodiments of the invention, the modified *M. haemolytica* lktCA gene cluster cassette comprises a leukotoxin promotor polynucleotide; a leukotoxin A ribosome binding site and start codon polynucleotide; a polynucleotide encoding at least leukotoxin A amino acids 732 to 953; and a polynucleotide encoding the added leukotoxin neutralizing epitope. In some embodiments of the invention, the leukotoxin promotor polynucleotide; the leukotoxin A ribosome binding site and start codon polynucleotide; the polynucleotide encoding at least leukotoxin A amino acids 732 to 953; and the polynucleotide encoding the added leukotoxin neutralizing epitope are from *M. haemolytica* strain A1 or *M. haemolytica* strain A6 bacteria.

In some embodiments of the invention, in the modified *M. haemolytica* lktCA gene cluster cassette of the invention, the leukotoxin promotor has the nucleotide sequence set forth in SEQ ID NO: 6; the leukotoxin A ribosome binding site and start codon have the nucleotide sequence set forth in SEQ ID NO: 7; the added leukotoxin neutralizing epitope has the amino acid sequence set forth in SEQ ID NO: 9; the leukotoxin A amino acids 732 to 953 have the amino acid sequence set forth in SEQ ID NO: 11. In some embodiments of the invention, the polynucleotide encoding lktA amino acids 732 to 953 in the modified *M. haemolytica* lktCA gene cluster cassette has the nucleotide sequence set forth in SEQ ID NO: 10. In some embodiments of the invention, the modified *M. haemolytica* lktCA gene cluster cassette encodes an amino acid sequence as set forth in SEQ ID NO: 13.

In an embodiment, the invention relates to a composition comprising a modified *M. haemolytica* lktCA gene cluster cassette comprising a polynucleotide encoding an additional leukotoxin neutralizing epitope inserted downstream of the native leukotoxin A start codon, where the composition is a polynucleotide, a plasmid, an expression vector, a host cell, a vaccine, or an immunogenic composition. In some embodiments of the invention, the composition comprising the modified *M. haemolytica* lktCA gene cluster cassette is a replacement plasmid, an attenuated *M. haemolytica* strain A1 bacterium, or an attenuated *M. haemolytica* strain A6 bacterium. In some embodiments, the invention relates to a vaccine or immunogenic composition comprising the modified *M. haemolytica* lktCA gene cluster cassette as disclosed herein, and optionally an adjuvant.

In an embodiment, the invention relates to a modified *M. haemolytica* lktCA gene cluster cassette as disclosed herein further comprising a polynucleotide encoding at least one heterologous antigen. In some embodiments of the invention, the polynucleotide encoding at least one heterologous antigen is inserted upstream of the polynucleotide encoding the added leukotoxin neutralizing epitope. In some embodiments, the invention relates to a composition comprising the modified *M. haemolytica* lktCA gene cluster cassette as disclosed herein and further comprising a polynucleotide encoding at least one heterologous antigen. In some embodiments of the invention, the composition is a polynucleotide, a plasmid, an expression vector, a host cell, a vaccine, or an immunogenic composition. In some embodiments of the invention, the composition comprising the modified *M. haemolytica* lktCA gene cluster cassette as disclosed herein and encoding at least one heterologous antigen is a replacement plasmid, an attenuated *M. haemolytica* strain A1 bacterium, or an attenuated *M. haemolytica* strain A6 bacterium. In some embodiments, the invention relates to a vaccine or immunogenic composition comprising a composition comprising a modified *M. haemolytica* lktCA gene cluster cassette encoding at least one heterologous antigen, and optionally an adjuvant.

In an embodiment, the invention relates to an *M. bovis* antigen. In some embodiments of the invention, the *M. bovis* antigen is elongation factor thermo unstable protein (EF-Tu) or heat shock protein DnaK. In some embodiments of the invention, the *M. bovis* antigen comprises EF-Tu and DnaK. In some embodiments of the invention, the *M. bovis* antigen is a chimeric *M. bovis* antigen. In some embodiments of the invention, the chimeric *M. bovis* antigen comprises EF-Tu and DnaK. In some embodiments of the invention, the chimeric *M. bovis* antigen has the amino acid sequence set forth in SEQ ID NO: 19. In some embodiments, the invention relates to a composition comprising at least one *M. bovis* antigen. In some embodiments of the invention, the composition comprising at least one *M. bovis* antigen is a polynucleotide, a plasmid, an expression vector, a host cell, a vaccine, or an immunogenic composition. In some embodiments of the invention, the composition comprising at least one *M. bovis* antigen is a replacement plasmid, an attenuated *M. haemolytica* strain A1 bacterium, or an attenuated *M. haemolytica* strain A6 bacterium. In some embodiments of the invention, the composition comprising at least one *M. bovis* antigen further comprises an adjuvant. In some embodiments, the invention relates to a vaccine or immunogenic composition comprising at least one *M. bovis* antigen, and optionally an adjuvant.

In an embodiment, the invention relates to a modified *M. haemolytica* lktCA gene cluster cassette as disclosed herein, and further comprising a polynucleotide encoding at least one *M. bovis* antigen. In some embodiments of the invention, the polynucleotide encoding at least one *M. bovis* antigen inserted in the modified *M. haemolytica* lktCA gene cluster cassette encodes EF-Tu or DnaK. In some embodiments of the invention, the polynucleotide encoding at least one *M. bovis* antigen inserted in the modified *M. haemolytica* lktCA gene cluster cassette encodes EF-Tu and DnaK. In some embodiments of the invention, the polynucleotide encoding at least one *M. bovis* antigen inserted in the modified *M. haemolytica* lktCA gene cluster cassette is a polynucleotide encoding a chimeric *M. bovis* antigen. In some embodiments of the invention, the polynucleotide encoding a chimeric *M. bovis* antigen inserted in the modified *M. haemolytica* lktCA gene cluster cassette comprises polynucleotide segments encoding EF-Tu and DnaK. In some embodiments of the invention, the chimeric *M. bovis* antigen has the amino acid sequence set forth in SEQ ID NO: 19. In some embodiments, the invention relates to a composition comprising a modified *M. haemolytica* lktCA gene cluster cassette as disclosed herein, and encoding at least one an *M. bovis* antigen. In some embodiments of the invention, the composition comprising a modified *M. haemolytica* lktCA gene cluster cassette as disclosed herein, and encoding at least one an *M. bovis* antigen is a polynucleotide, a plasmid, an expression vector, a host cell, a vaccine, or an immunogenic composition. In some embodiments of the invention, the composition comprising a modified *M. haemolytica* lktCA gene cluster cassette as disclosed herein and encoding at least one an *M. bovis* antigen is a replacement plasmid, an attenuated *M. haemolytica* strain A1 bacterium, or an attenuated *M. haemolytica* strain A6 bacterium. In some embodiments, the invention relates to a vaccine or immunogenic composition comprising a modified *M. haemolytica* lktCA gene cluster cassette as disclosed herein, and encoding at least one an *M. bovis* antigen, and optionally an adjuvant.

In an embodiment, the invention relates to a method for provoking an immune response in an animal, the method comprising administering to the animal at least one effective dose of a composition comprising a modified *M. haemolytica* lktCA gene cluster cassette comprising a polynucleotide encoding an additional leukotoxin neutralizing epitope. In an embodiment, the invention relates to a method for provoking an immune response in an animal, the method comprising administering to the animal at least one effective dose of a composition comprising a modified *M. haemolytica* lktCA gene cluster cassette comprising a polynucleotide encoding an additional leukotoxin neutralizing epitope, and further comprising at least one polynucleotide encoding a heterologous antigen. In an embodiment, the invention relates to a method for provoking an immune response in an animal, the method comprising administering to the animal at least one effective dose of a composition comprising a modified *M. haemolytica* lktCA gene cluster cassette comprising a polynucleotide encoding an additional leukotoxin neutralizing epitope, and further comprising at least one polynucleotide encoding a heterologous antigen, where the heterologous antigen is an *M. bovis* antigen. In an embodiment, the invention relates to a method for provoking an immune response in an animal, the method comprising administering to the animal at least one effective dose of a composition comprising an *M. bovis* antigen.

In some embodiments of the invention, the animal in the method for provoking an immune response in an animal is a mammal. In some embodiments of the invention, the mammal in the method for provoking an immune response in an animal is a cow, a bull, a steer, a heifer, a sheep, a goat, a pig, a bison, an elk, a camel, a dog, or a deer. In some embodiments of the invention, the composition to provoke an immune response in an animal is administered orally, nasally, enterally, parenterally, intramuscularly, intravenously, subcutaneously, intradermally, rectally, vaginally, topically, ocularly, pulmonarily, or by contact application.

In an embodiment, the invention relates to a kit comprising a modified *M. haemolytica* lktCA gene cluster cassette comprising a polynucleotide encoding an additional leukotoxin neutralizing epitope. In an embodiment, the invention relates to a kit comprising a modified *M. haemolytica* lktCA gene cluster cassette comprising a polynucleotide encoding an additional leukotoxin neutralizing epitope, and further comprising a polynucleotide encoding a heterologous antigen. In an embodiment, the invention relates to a kit comprising a modified *M. haemolytica* lktCA gene cluster cassette comprising a polynucleotide encoding an additional leukotoxin neutralizing epitope, and further comprising a polynucleotide encoding at least one *M. bovis* antigen. In an embodiment, the invention relates to a kit comprising an *M. bovis* antigen.

BRIEF DESCRIPTION OF THE SEQUENCE LISTING

Figure 1:
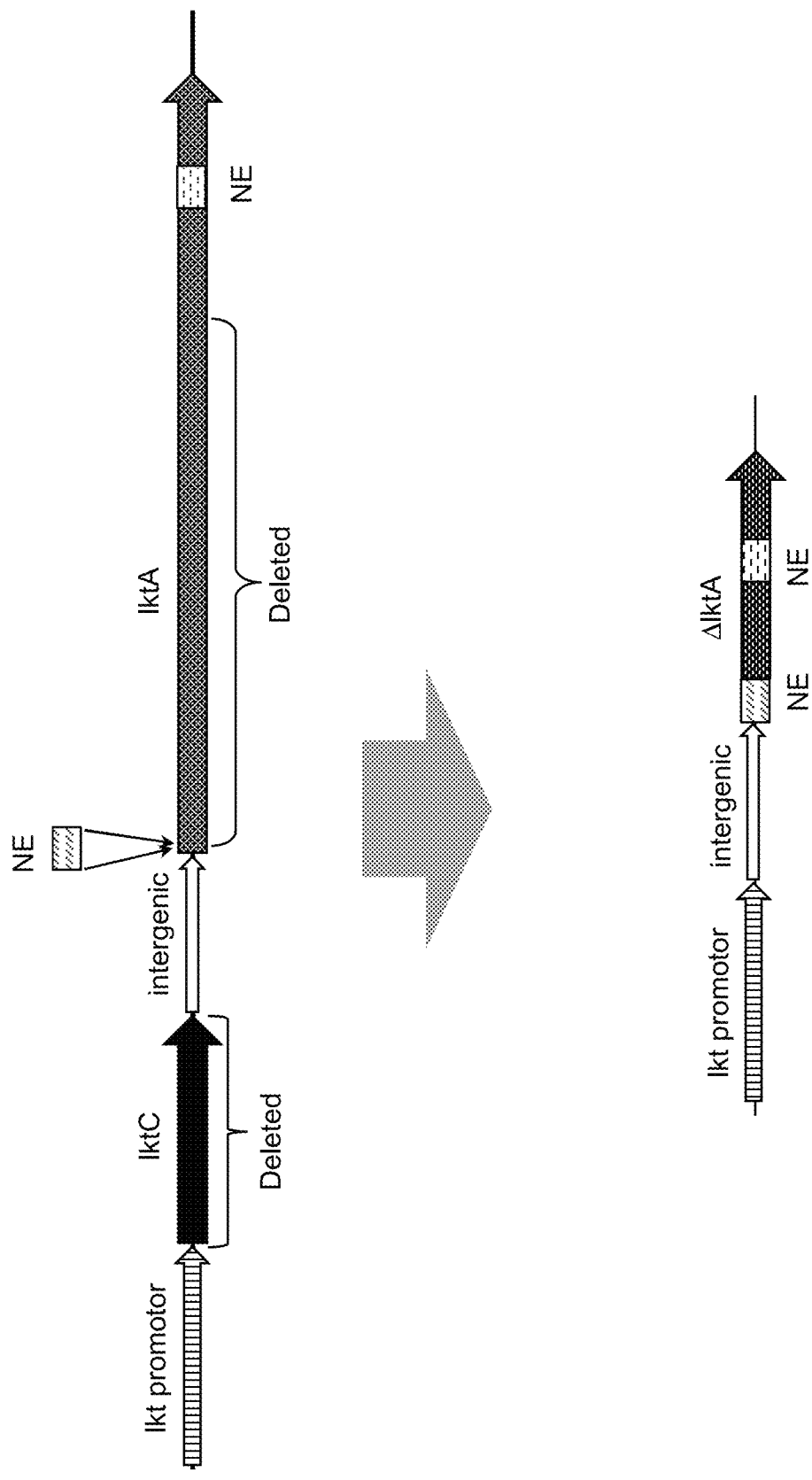
FIG. 1 depicts a schematic of the generation of *M. haemolytica* ΔlktCAV4 cassette. The leukotoxin lktCA gene cluster and the polynucleotide encoding the leukotoxin neutralizing epitope added after the lktA start site are depicted on the upper portion of the figure. Portions of the lktCA gene cluster to be deleted to generate the ΔlktCAV4 cassette are shown bracketed. The *M. haemolytica* ΔlktCAV4 cassette is depicted on the lower portion of the figure. The leukotoxin promotor is shown by a light gray arrow; the leukotoxin C gene is shown by a black arrow; the lktC-lktA intergenic region (leukotoxin A ribosome binding site and start codon) is shown by a white arrow; the leukotoxin A gene is shown by a dotted arrow with the polynucleotide encoding the leukotoxin neutralizing epitope (NE) shown by alternating dashes; and the polynucleotide encoding the added NE is shown by stripes of back dashes.

The nucleotide and amino acid sequences disclosed in the specification are listed in Table 1, below.

TABLE 1

| Identifier | Type | Description |
|---|---|---|
| SEQ ID NO: 1 | nucleotide | M. haemolytica lktCA gene cluster |
| SEQ ID NO: 2 | nucleotide | ΔlktCAV4 down replacement arm |
| SEQ ID NO: 3 | nucleotide | Down arm forward primer TM56 |
| SEQ ID NO: 4 | nucleotide | Down arm reverse primer TM57 |
| SEQ ID NO: 5 | nucleotide | ΔlktCAV4 up replacement arm |
| SEQ ID NO: 6 | nucleotide | native leukotoxin promotor |
| SEQ ID NO: 7 | nucleotide | lktC-lktA intergenic region |
| SEQ ID NO: 8 | nucleotide | Codon-optimized sequence encoding SEQ ID NO: 9 |
| SEQ ID NO: 9 | amino acid | Added leukotoxin neutralizing epitope |
| SEQ ID NO: 10 | nucleotide | leukotoxin A nucleotides 2192 to 3022 |
| SEQ ID NO: 11 | amino acid | translation of SEQ ID NO: 10 |
| SEQ ID NO: 12 | nucleotide | ΔlktCAV4 cassette |
| SEQ ID NO: 13 | amino acid | ΔlktCAV4 cassette (translation of SEQ ID NO: 12) |
| SEQ ID NO: 14 | nucleotide | Codon-optimized sequence encoding M. bovis EF-Tu |
| SEQ ID NO: 15 | amino acid | M. bovis EF-Tu (translation of SEQ ID NO: 14) |
| SEQ ID NO: 16 | nucleotide | Codon-optimized sequence encoding M. bovis DnaK |
| SEQ ID NO: 17 | amino acid | M. bovis DnaK (translation of SEQ ID NO: 16) |
| SEQ ID NO: 18 | nucleotide | Codon-optimized sequence encoding SEQ ID NO: 19 |
| SEQ ID NO: 19 | amino acid | M. bovis EF-Tu/DnaK chimera (translation of SEQ ID NO: 18) |
| SEQ ID NO: 20 | nucleotide | ΔlktCAV4Mbovis cassette |
| SEQ ID NO: 21 | amino acid | ΔlktCAV4Mbovis cassette |
| SEQ ID NO: 22 | nucleotide | Primer ΔlktCAV4diagF |
| SEQ ID NO: 23 | nucleotide | Primer ΔlktCAV4diagR |
| SEQ ID NO: 24 | nucleotide | Primer MbovispolyF |
| SEQ ID NO: 25 | nucleotide | Primer MbovispolyR |
| SEQ ID NO: 26 | nucleotide | Primer MhSt1F |
| SEQ ID NO: 27 | nucleotide | Primer MhSt1R |
| SEQ ID NO: 28 | nucleotide | Primer MhSt6F |
| SEQ ID NO: 29 | nucleotide | Primer MhSt6R |

DETAILED DESCRIPTION

The inventors have created a modified M. haemolytica lktCA gene cluster cassette comprising a polynucleotide encoding an added leukotoxin neutralizing epitope that may be used as a vector, or as a vaccine. This modified M. haemolytica lktCA gene cluster cassette was effective in protecting calves against virulent M. haemolytica challenge. The inventors have assembled a chimeric M. bovis antigen effective in protecting calves against virulent M. bovis. The inventors have inserted a polynucleotide encoding the chimeric M. bovis antigen into the modified M. haemolytica lktCA gene cluster cassette. This modified M. haemolytica lktCA gene cluster cassette expressing the chimeric M. bovis antigen was effective in protecting calves against virulent M. bovis challenge.

M. haemolytica is a gram-negative bacterium which is part of the normal nasal-pharyngeal flora of cattle, sheep, and goats. Under stress and/or concurrent respiratory infection, M. haemolytica can gain access to the lungs and cause fibrinous pneumonia. When compared to the wild-type parent, M. haemolytica possessing inactive leukotoxin are attenuated and elicit greatly reduced lung damage following experimental pulmonary challenge. Yet such modified strains retain the capacity to colonize the upper respiratory tract of cattle (Tatum F M et al., 1998, "Construction of an isogenic leukotoxin deletion modified of Pasteurella haemolytica serotype 1: characterization and virulence," Microb. Pathog. 24: 37-46). Moreover, cattle vaccinated mucosally with such defined M. haemolytica modified strains expressing and secreting inactive, yet immunogenic, leukotoxin (leuko-toxoid) are capable of generating neutralizing antibodies to leukotoxin that afford them resistant to virulent challenge (Briggs R E et al., 2012, "Mucosal and parenteral vaccination against pneumonic pasteurellosis in cattle with a modified-live in frame lktA deletion modified of Mannheimia haemolytica," Microb. Pathog. 52: 302-309).

The leukotoxin (lkt) operon of M. haemolytica codes for four proteins: an internal acyltransferase encoded by lktC; the structural toxin encoded by lktA; an inner membrane protein encoded by lktB; and a membrane fusion protein encoded by lktD. The genes for these four proteins are physically adjacent on the chromosome and are transcribed as lktCA or lktCABD messages.

U.S. Pat. No. 6,331,303, issued Dec. 18, 2001, discloses P. haemolytica bacterium which expresses no biologically active leukotoxin, expresses a leukotoxin molecule lacking amino acids 34 to 378, and contains no foreign DNA. In 1999, P. haemolytica was renamed as Mannheimia haemolytica.

US Patent Publication No. 2014/0170190 discloses a modified M. haemolytica strain A1 lktCA gene cluster with a deletion of a polynucleotide fragment consisting of the nucleotides encoding amino acid 4 of leukotoxin C to amino acid 707 of leukotoxin A, and replacement of the native leukotoxin C ribosome binding site (rbs) with an E. coli consensus rbs to generate D153ΔlktCA4-707rbs. The mutated lktCA gene cluster was introduced into wild-type M. haemolytica strains A1 and A6, resulting in attenuated bacteria. The attenuated M. haemolytica A1 and A6 strains were lyophilized, resuspended, and administered intranasally to calves aged 5 to 6 weeks. When administered intranasally, the mixture of attenuated M. haemolytica A1 and A6 strains containing D153ΔlktCA4-707rbs afforded protection to M. haemolytica challenge. When challenged with M. haemolytica A1 strain, nasal administration of M. haemolytica A1 and A6 strains containing D153ΔlktCA4-707rbs afforded an average reduction in lung lesion of 62.0% and 76.7% when compared to sham-inoculated cattle. When challenged with M. haemolytica A6 strain, nasal administration of M. haemolytica A1 and A6 strains containing D153ΔlktCA4-707rbs afforded an average reduction in lung lesion of 85.04% and 14.7% when compared to sham-inoculated cattle. U.S. Pat. No. 9,370,561, issued Jun. 21, 2016 from US Patent Publication No. 2014/0170190, and claims a vaccine comprising live, attenuated M. haemolytica A1 and A6 strains containing nucleic acid deletions in their respective leukotoxin A genes, that provide protective immune response against disease caused by M. haemolytica strains A1 and A6.

US Patent Application Publication 2019/0381161 discloses an oral vaccine against ruminant respiratory disease, comprising live attenuated M. haemolytica bacteria, sucrose, and a Polyvinylpyrrolidone (PVP). The disclosed method allowed reduced dosage of the modified-live vaccine product with retained efficacy when the vaccine was delivered by an oral route via drink.

In an embodiment, in a 5' to 3' orientation, the modified M. haemolytica lktCA gene cluster cassette of the invention comprises a leukotoxin promotor, a leukotoxin A ribosome binding site and start codon, a polynucleotide encoding an added leukotoxin neutralizing epitope; and a polynucleotide encoding at least leukotoxin A amino acids 732 to 953. A schematic of the preparation of the modified M. haemolytica lktCA gene cluster cassette of the invention is depicted on FIG. 1. The modified M. haemolytica lktCA gene cluster cassette of the invention lacks the lktC ribosome binding site, all the nucleotides encoding leukotoxin C, and nucleotides encoding leukotoxin A amino acids 2 to at least 710. In some embodiments of the invention, the modified *M. haemolytica* lktCA gene cluster cassette of the invention lacks nucleotides encoding leukotoxin A amino acids 2 to 731.

Use of bacterial vectors as vehicles to deliver recombinant antigens emerged in the late 1990s. Bacteria-based antigen delivery vectors exhibit multiple advantages, such as the possibility to control its intrinsic infectious power, its non-integrative properties, ability to regulate the amount and in vivo localization of the antigen, a potential for multiple vaccine delivery routes, potent stimulation of the innate and adaptive immune systems, and relatively low manufacturing costs. Bacterial vectors most frequently used as vaccine vectors are *Listeria* and *Salmonella*. Other attenuated bacteria used to express heterologous antigens, are *Pseudomonas aeruginosa*, *Mycobacterium bovis* (*Bacillus* Calmette-Guerin), *Vibrio anguillarum*, and *Vibrio V. cholera* (see review by Ding, C. al., "*Live Bacterial Vaccine Vector and Delivery Strategies of Heterologous Antigen: A Review,*" 2018, Immunology Letters 197: 70-77).

The instant disclosure relates to a modified *M. haemolytica* lktCA gene cluster cassette comprising a polynucleotide encoding an added leukotoxin neutralizing epitope. The polynucleotide encoding the added leukotoxin neutralizing epitope may be inserted downstream of the leukotoxin A ribosome binding site and start codon. Prior to the present disclosure, the effect of the insertion of nucleotides encoding an additional leukotoxin neutralizing epitope to the *M. haemolytica* lktCA gene cluster was not known. Prior to the instant application, it was not known if a modified *M. haemolytica* lktCA gene cluster cassette with an polynucleotide encoding an additional leukotoxin neutralizing epitope would be useful for the expression of heterologous antigens, and/or for the preparation of compositions, vaccines, or immunogenic compositions for administration to animals. In the instant disclosure, a gene replacement plasmid comprising the modified *M. haemolytica* lktCA gene cluster cassette was designed which recombined with wild-type *M. haemolytica* A1 and A6 serotypes to generate attenuated *M. haemolytica* strain A1 and strain A6 bacteria. Prior to the instant disclosure, it was not known whether administration of a vaccine comprising a modified *M. haemolytica* lktCA gene cluster cassette comprising a polynucleotide encoding an added neutralizing would elicit an immune response in an animal.

Disclosed herein are modified lktCA gene cluster cassettes derived from D153 ltkCA gene cluster. The wild type lktCA gene cluster has the nucleotide sequence set forth in SEQ ID NO: 1.

The inventors prepared an *M. haemolytica* replacement plasmid comprising the modified *M. haemolytica* lktCA gene cluster cassette. The modified *M. haemolytica* lktCA gene cluster cassette contains an inserted polynucleotide encoding an added leukotoxin neutralizing epitope. The polynucleotide encoding the added leukotoxin neutralizing epitope may be inserted downstream of the lktA ribosome binding site and start codon. The modified *M. haemolytica* lktCA gene cluster cassette contains a deletion of lktC gene nucleotides −12 to 504, and an in-frame deletion of the lktA gene nucleotides 4 to 2191, and an insertion of nucleotides encoding an additional leukotoxin neutralizing epitope downstream of the lktA ribosome binding site and start codon, and upstream of the lktA nucleotide 2192. The inventors utilized the replacement plasmid, designated herein pΔlktCAV4, to modify *M. haemolytica* strains D153 and D174, virulent lung isolates of *M. haemolytica* serotypes 1 and 6 respectively. The resultant *M. haemolytica* modified products retain the native lkt promoter, and the native lktC/lktA intervening region (including the lktA ribosome binding site, rbs). In the instant application modified *M. haemolytica* strains comprising the ΔlktCAV4 cassette are designated as D153ΔlktCAV4 and D174ΔlktCAV4. Prior to the present disclosure, the effect of the deletion of lktC nucleotides −12 to 504, the in-frame deletion of lktA gene nucleotides 4 to 2191, and the addition of a polynucleotide encoding an additional leukotoxin neutralizing epitope in modified *M. haemolytica* strains D153 and D174M was not known. Prior to the instant application, it was not known if a modified lktCA gene cluster cassette comprising a deletion of lktC nucleotides −12 to 504, and replacement of the lktA nucleotides 4 to 2191 for a polynucleotide encoding an additional leukotoxin neutralizing epitope would generate a cassette useful for the expression of heterologous antigens and/or the preparation of vaccines or immunogenic compositions for administration to animals. Prior to the instant disclosure, it was not known whether administration of a vaccine comprising attenuated *M. haemolytica* bacteria comprising D153ΔlktCAV4 and/or D174ΔlktCAV4 would elicit an immune response in mammals.

The engineered insertions and deletions into the lktCA gene cluster cassette result in novel polynucleotides which are useful for the expression of heterologous antigens. The heterologous antigen may be added directly to the ΔlktCAV4 cassette, to a plasmid containing the ΔlktCAV4 cassette, or to a bacteria comprising the ΔlktCAV4 cassette. For example, polynucleotides encoding heterologous antigens may be expressed in a ΔlktCAV4 cassette, a plasmid containing such cassette, or *M. haemolytica* containing such cassette (such as D153ΔlktCAV4 and D174ΔlktCAV4). In an embodiment, the invention is directed to at least one modified *M. haemolytica* lktCA gene cluster cassette comprising a polynucleotide encoding an additional leukotoxin neutralizing epitope and encoding a heterologous antigen. In some embodiments of the invention, the modified *M. haemolytica* lktCA gene cluster cassette comprises the native leukotoxin promoter, the native lktC-lktA intergenic region, added nucleotides encoding an additional leukotoxin neutralizing epitope, and native nucleotides encoding lktA amino acids 732 to 953 (set forth in SEQ ID NO: 11). In some embodiments of the invention, the modified *M. haemolytica* lktCA gene cluster cassette comprises lktA nucleotides 2192 to 3022 of SEQ ID NO: 1 (ΔlktCAV4 cassette).

In an embodiment, the invention relates to a modified *M. haemolytica* lktCA gene cluster cassette comprising a leukotoxin promoter, a leukotoxin A ribosome binding site and start codon, a polynucleotide encoding an added leukotoxin neutralizing epitope, and a polynucleotide encoding leukotoxin A amino acids 732 to 953. In some embodiments of the invention, the leukotoxin promotor, the lktA ribosome binding site and start codon, the polynucleotide encoding an added leukotoxin neutralizing epitope, and the polynucleotide encoding at least leukotoxin A amino acids 732 to 953 are from *M. haemolytica* strain A1 or *M. haemolytica* strain A6. In some embodiments of the invention, the modified *M. haemolytica* lktCA gene cluster cassette comprises a leukotoxin promotor polynucleotide fragment with the nucleotide sequence set forth in SEQ ID NO: 6; an lktA ribosome binding site and start codon with the nucleotide sequence set forth in SEQ ID NO: 7; an added leukotoxin neutralizing epitope with the amino acid sequence QLVITNSKKEKV-TIQNWFREADFAKEVPNYKATKDEKIEEIIGQNGER-ITS KQVDDLIAKGNGKITQDELSKVVDNYEGS, set forth in SEQ ID NO: 9. In some embodiments of the invention, leukotoxin A amino acids 732 to 953 have the amino acid sequence set forth in SEQ ID NO: 11. In some embodiments of the invention, the polynucleotide fragment encoding the added leukotoxin neutralizing epitope has the nucleotide sequence set forth in SEQ ID NO: 8. In some embodiments of the invention, the modified *M. haemolytica* lktCA gene cluster cassette encodes an amino acid sequence set forth in SEQ ID NO: 13.

In an embodiment, the invention relates to a composition comprising a modified *M. haemolytica* lktCA gene cluster cassette comprising a polynucleotide encoding an added leukotoxin neutralizing epitope. In some embodiments of the invention, the composition is a polynucleotide, a plasmid, an expression vector, a host cell, a vaccine, or an immunogenic composition. In some embodiments of the invention, the composition comprising a modified *M. haemolytica* lktCA gene cluster cassette comprising a polynucleotide encoding an added leukotoxin neutralizing epitope is a replacement plasmid, an attenuated *M. haemolytica* strain A1 bacteria, or an attenuated *M. haemolytica* strain A6 bacteria. In some embodiments of the invention, the composition comprising a modified *M. haemolytica* lktCA gene cluster cassette comprising a polynucleotide encoding an added leukotoxin neutralizing epitope is a vaccine or immunogenic composition, and optionally an adjuvant. In some embodiments, the invention relates to at least one plasmid comprising the ΔlktCAV4 cassette. In some embodiments of the invention, the at least one plasmid is a replacement plasmid. In some embodiments, the invention relates to at least one bacteria comprising the ΔlktCAV4 cassette.

Deletion of lktC gene nucleotides −12 to 504 deletes the lktC ribosome binding site and the entire lktC coding region. Deletion of lktA gene nucleotides 4 through 2191 retains the lktC-lktA intergenic region including the lktA ribosome binding site and start codon, as well as lktA gene nucleotides 2192 to 2862, which include the polynucleotides encoding the leukotoxin glycine rich region and the leukotoxin neutralizing epitope. In some embodiments of the invention the modified lktCA gene cluster cassette contains added nucleotides corresponding to restriction endonuclease recognition sites. In some embodiments of the invention, the modified *M. haemolytica* lktCA gene cluster cassette of the invention contains added nucleotides corresponding to at least one EcoRI restriction endonuclease recognition site (nucleotides 1 to 6 of SEQ ID NO: 5). In some embodiments of the invention, the modified *M. haemolytica* lktCA gene cluster cassette contains nucleotides corresponding to at least one MfeI restriction endonuclease recognition site (nucleotides 1 to 6 of SEQ ID NO: 18). In some embodiments of the invention, the modified *M. haemolytica* lktCA gene cluster cassette contains nucleotides corresponding to at least one BamHI restriction endonuclease recognition site (nucleotides 234 to 240 of SEQ ID NO: 8). At least one EcoRI, BamHI, or MfeI restriction endonuclease recognition site may be used to facilitate preparation of the modified *M. haemolytica* lktCA gene cluster cassette, its insertion into plasmids or vectors, or insertion of polynucleotides encoding heterologous antigens into the modified *M. haemolytica* lktCA gene cluster cassette.

In some embodiments of the invention, the lkt promotor in the modified *M. haemolytica* lktCA gene cluster cassette has the nucleotide sequence set forth in SEQ ID NO: 6. In some embodiments of the invention, the leukotoxin neutralizing epitope encoded by the added polynucleotide inserted downstream of the lktC-lktA intergenic region in the modified *M. haemolytica* lktCA gene cluster cassette has the amino acid sequence set forth in SEQ ID NO: 9. In some embodiments of the invention, the codon-optimized nucleotide sequence encoding the added leukotoxin neutralizing epitope in the modified *M. haemolytica* lktCA gene cluster cassette is set forth in SEQ ID NO: 8. In some embodiments of the invention, the lktC-lktA intergenic region in the modified *M. haemolytica* lktCA gene cluster cassette has the nucleotide sequence set forth in SEQ ID NO: 7. In some embodiments of the invention, the LktA amino acids 732 to 953 in the modified *M. haemolytica* lktCA gene cluster cassette have the amino acid sequence set forth in SEQ ID NO: 11. In some embodiments of the invention, the LktA amino acids 732 to 953 in the modified *M. haemolytica* lktCA gene cluster cassette are encoded by the nucleotide sequence set forth in SEQ ID NO: 10. In some embodiments of the invention, the modified *M. haemolytica* lktCA gene cluster cassette ΔlktCAV4 encodes a polypeptide with the amino acid sequence set forth in SEQ ID NO: 13. In some embodiments of the invention, the modified *M. haemolytica* lktCA gene cluster cassette comprises the nucleotide sequence set forth in SEQ ID NO: 12.

In an embodiment, the invention relates to a modified *M. haemolytica* lktCA gene cluster cassette comprising a polynucleotide encoding an additional leukotoxin neutralizing epitope, further comprising a polynucleotide encoding at least one heterologous antigen. In some embodiments of the invention, the polynucleotide encoding the at least one heterologous antigen is inserted upstream of the polynucleotide encoding the added leukotoxin neutralizing epitope. In some embodiments of the invention, the polynucleotide encoding the at least one heterologous antigen inserted in the modified *M. haemolytica* lktCA gene cluster cassette may be from *Achromobacter anitratum*; *Actinobacillus lignieresi*; *Actinomyces bovis*; *Alcaligenes faecalis*; *Bacillus anthracis*; *Brucella abortus*; *Clostridium chauvoei*; *Clostridium hemolyticum*; *Clostridium novyi*; *Clostridium perfringens*; *Clostridium perfringens* Type C; *Clostridium septicum*; *Corynebacterium pyogenes*; *Corynebacterium renale*; *Diplococcus pneumoniae*; *Enterobacter aerogenes*; *Erysipelothrix insidiosa*; *Escherichia coli*; *Hemophilus bovis*; *Klebsiella pneumoniae*; *Leptospira canicola*; *Leptospira hyos*; *Leptospira icterohaemorrhagica*; *Leptospira pomona*; *Leptospira sejroc phosa*; *Listeria monocytogenes*; *Moraxella bovis*; *Mycobacterium tuberculosis*; *Mycoplasma bovis*; *Mycoplasma mycoides*; *Nocardia asteroids*; *Pasteurella haemolytica*; *Pasteurella multocida*; *Proteus mirabilis*; *Pseudomonas aeruginosa*; *Salmonella anatum*; *Salmonella arizona*; *Salmonella dublin*; *Salmonella newport*; *Salmonella typhimurium*; *Sphaerophorus necrophorus*; *Staphylococcus aureus*; *Streptococcus agalactiae*; *Streptococcus dysgalactiae*; *Streptococcus pyogenes*; *Streptococcus uberus*; *Vibrio fetus*; and *Yersinia pseudotuberculosis*.

*Mycoplasma bovis* (*M. bovis*) is a member of the class Mollicutes, a wall-less group of bacteria that comprise a diverse group of organisms possessing the smallest genomes of self-replicating organisms. *M. bovis* was first recognized in 1961 when the bacterium was isolated from a cow with severe mastitis. *M. bovis* can cause a variety of other disorders including of pneumonia, arthritis, keratoconjunctivitis, mastitis, and otitis media. *M. bovis* is able to colonize and persist on mucosal surfaces, and form biofilms. *M. bovis* adhesin molecules, such as variable surface proteins (VSP), can undergo rapid size change which presents an ever changing target and contributes to immune evasion (Lysnyansky I, et al., "Phenotypic Switching of Variable Surface Lipoproteins in Mycoplasma bovis Involves High-Frequency Chromosomal Rearrangements," 1996, J. Bacteriol. 178: 5395 to 5401; Beier T, et al., "Intraspecies Polymorphism of vsp Genes and Expression Profiles of Variable Surface Protein Antigens (Vsps) in Field Isolates of Mycoplasma bovis," 1998 Vet. Microbiol. 63:189 to 203). Both, in vitro and in vivo, evidence suggests M. bovis can survive intracellularly and cause apoptosis. The economic cost attributed to M. bovis in the United States alone is estimated at one billion U.S. dollars annually.

The role of M. bovis in the multi-factorial bovine respiratory disease (BRD) is complex. In naturally-infected cattle, M. bovis is often detected in association with other microorganisms leading to the hypothesis that synergism of pathogens contributes to the severe lung lesions observed in cattle afflicted with pneumonia (Maunsell F. P., et al., 2011, "Mycoplasma bovis Infections in Cattle," J. Vet. Intern. Med. 25(4): 722-783; Caswell J. L. and Archambult M., 2008, "Mycoplasma bovis pneumonia in cattle," Anim. Health Res. Rev. 8(2): 161-186; and Nicholas R. A. J. and Ayling R. D., 2003, "Mycoplasma bovis: disease, diagnosis, and control," Res. Vet. Sci. 74: 105-112). The most common identified microorganisms co-isolated with M. bovis are Pasteurella multocida, Mannheimia haemolytica, Histophilus somni, bovine respiratory syncytial virus (BRSV), bovine herpes virus 1 (BHV-1), bovine viral diarrhea virus (BVDV), and parainfluenza virus type 3. A recent study investigating a large number of mortalities in North America bovine feedlots showed Mannheimia haemolytica to be most frequently isolated (91%), followed by Mycoplasma bovis (63%), Histophilus somnus (57%), and Pasteurella multocida (13%) (Klima C. L., et al., "Pathogens of Bovine Respiratory Disease in North American Feedlots Conferring Multidrug Resistance Via Integrative Conjugative Elements," 2014, J. Clin. Microbiol. 52: 438-448).

Improved vaccines against M. bovis which are safe and effective against all of its disease manifestations are urgently needed. Research on the development of protective vaccines against M. bovis has been active for many years. Although there has been some bacterin-based vaccines, the wide antigenic variation shown by M. bovis suggests that such a vaccine produced from a single isolate may not confer broad protection against this phenotypically adaptive bacterium. Because of M. bovis' extreme variability, selecting conserved M. bovis proteins as the underpinning for a M. bovis vaccine is an alternative approach towards creating a widely effective vaccine.

Heat shock proteins are a family of proteins that are produced by cells in response to exposure to stressful conditions. They were first described in relation to heat shock, but are now known to also be expressed during other stresses including exposure to cold, UV light, and during wound healing or tissue remodeling. Mycobacterial heat shock proteins serve as molecular chaperones for other proteins during stress conditions and help to recycle damaged proteins. Heat shock proteins DnaK and GroEL are molecular chaperones that assist in correct folding and assembly of proteins. DnaK and GroEL are conserved in both prokaryotes and eukaryotes. Polynucleotides encoding DnaK have been used with mixed results to protect mice against Chlamydophila abortus infection (Héchard C. et al., "Protection evaluation against Chlamydophila abortus challenge by DNA vaccination with a dnaK-encoding plasmid in pregnant and non-pregnant mice," 2002, Vet. Res. 33(3): 313-326; Héchard C. et al., "Proteic boost enhances humoral response induced by DNA vaccination with the dnaK gene of Chlamydophila abortus but fails to protect pregnant mice against a virulence challenge," Vet. Res. 34(1): 119-125). A subunit vaccine comprising Francisella tularensis (FT) DnaK and surface lipoprotein Tul4 protected mice against lethal respiratory infection with FT (Ashtekar A. R. et al., "A Mucosal Subunit Vaccine Protects against Lethal Respiratory Infection with Francisella tularensis LVS," 2012, PLoS ONE 7(11): e50460). A mutated human papillomavirus (HPV) E6 fused to polynucleotides encoding HSP70 was used as a DNA vaccine in a Phase I clinical trial, and found to generate HPV-specific T-cell responses in patients (Trimble C. et al., "A Phase I Trial of a Human Papillomavirus DNA Vaccine for HPV16+ Cervical Intraepithelial Neoplasia 2/3," 2009, Clin. Cancer Res. 15(1):), and mycobacterial HSP70 has been shown to induce protective immunity by DNA vaccination in mice (Sachdeva R., et al., "Immunogenicity and Efficacy of Single Antigen Gp63, Polytope and PolytopeHSP70 DNA Vaccines against Visceral Leishmaniasis in Experimental Mouse Model," 2009, PLoS ONE e7880).

The elongation factor thermo unstable protein (EF-Tu) is a prokaryotic elongation factor responsible for catalyzing the binding of an aminoacyl-tRNA (aa-tRNA) to the ribosome. The EF-Tu protein facilitates the selection and binding of an aa-tRNA to the A-site of the ribosome. EF-Tu is one of the most abundant and highly conserved proteins in prokaryotes. EF-Tu has been found on the surface of a wide range of prokaryotes, and in membrane vesicles in several bacteria. In M. bovis, EF-Tu stimulates a humoral immune response and interacts with host immune regulators, as well as binding to innate immune effectors (Harvey K. L. et al., 2019, "The Diverse Functional Roles of Elongation Factor Tu (EF-Tu) in Microbial" Front. Microbiol. 24 Oct. 2019).

In an embodiment, the invention relates to an M. bovis antigen comprising EF-Tu or DnaK. In some embodiments of the invention, the M. bovis antigen comprises EF-Tu and DnaK. In some embodiments of the invention, the M. bovis antigen comprises a chimera. In some embodiments of the invention, the M. bovis antigen comprises an EF-Tu and DnaK chimera. In some embodiments, the invention relates to a composition comprising the M. bovis antigen of the invention. In some embodiments of the invention, the composition comprising an M. bovis antigen is a polynucleotide, a plasmid, an expression vector, a host cell, a vaccine, or an immunogenic composition. In some embodiments of the invention, the composition comprising the M. bovis antigen is a replacement plasmid, an attenuated M. haemolytica strain A1 bacterium, or an attenuated M. haemolytica strain A6 bacterium. In some embodiments, the invention relates to a vaccine or immunogenic composition comprising the M. bovis antigen as disclosed herein, and optionally an adjuvant.

Figure 2:
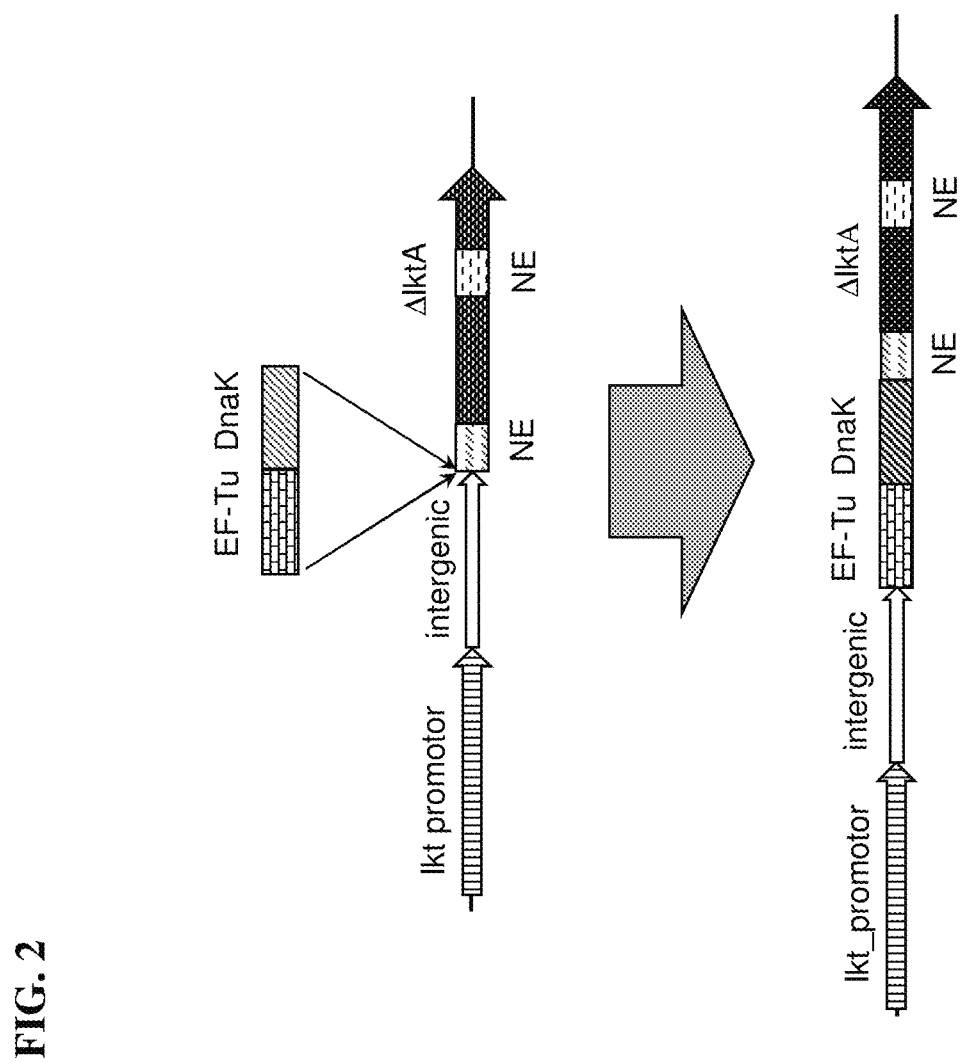
FIG. 2 depicts a schematic of the generation of the *M. haemolytica* ΔlktCAV4Mbovis cassette from the *M. haemolytica* ΔlktCAV4 cassette. The *M. haemolytica* ΔlktCAV4 cassette and the polynucleotide encoding the added *M. bovis* EF-Tu/DnaK chimera are depicted on the upper portion of the figure. The *M. haemolytica* ΔlktCAV4Mbovis cassette is depicted on the lower portion of the figure. The leukotoxin promotor is shown by a light gray arrow; the lktC-lktA intergenic region is shown by a white arrow; the polynucleotide encoding the added NE is shown by stripes of back dashes; the leukotoxin A gene portions present are shown by a dotted arrow; the polynucleotide encoding leukotoxin A NE is shown by alternating dashes; the polynucleotide encoding *M. bovis* EF-Tu is shown by horizontal bricks; and the polynucleotide encoding *M. bovis* DnaK is shown by diagonal stripes.

Live M. haemolytica leuko-toxoid modified strains have been proven safe and effective cattle vaccines when administered mucosally. The co-expression of potentially protective M. bovis antigens coupled to leuko-toxoid could serve as platform affording two-way protection against these two important pathogens causing BRD. To realize such a product, a polynucleotide encoding antigenic portions of the conserved M. bovis proteins Elongation factor Tu (EF-Tu) and Hsp70 (DnaK) was custom synthesized and inserted in-frame into a temperature-sensitive replacement plasmid containing the ΔlktCAV4 leuko-toxoid sequence ("Construction of In-Frame aroA Deletion Modifieds of Mannheimia haemolytica, Pasteurella multocida, and Haemophilus somnus by Using a New Temperature-Sensitive Plasmid," 2005, Appl. Environ. Microbiol. 71(11): 7196-7202). The resulting chimeric sequence was called ΔlktCAV4Mbovis. FIG. 2 depicts a schematic of the construction of the ΔlktCAV4Mbovis cassette from the ΔlktCAV4 cassette. The same replacement plasmid was used to generate chromosomal modified strains of *M. haemolytica* serotype 1 and serotype 6 that expressed and secreted *M. bovis* EF-Tu-Hsp70 antigenic peptides coupled to leukotoxoid.

Vaccine strains comprising the ΔlktCAV4Mbovis cassette were produced for *M. haemolytica* serotypes A1 and A6 because cattle develop resistance to further mucosal colonization, in serotype-specific manner (Frank G. H., 1985, "Serotype-specific resistance to nasal colonization by *Pasteurella haemolytica* in cattle," Am. J. Vet. Res. 46(11): 2245-2248). Thus, to increase the probability that colonization would occur, *M. haemolytica* serotypes 1 and 6 comprising the ΔlktCAV4Mbovis cassette were administered as vaccine in this study. The modified *M. haemolytica* comprising the ΔlktCAV4Mbovis cassette can colonize the nasal-pharyngeal mucosa of cattle upon either nasal or oral delivery. When established in the upper respiratory tract these modified *M. haemolytica* will secrete recombinant immunogenic fusion peptide consisting of leuko-toxoid and *M. bovis* EF-Tu-Hsp70 antigens directly onto the mucosal surface of the host to stimulate targeted immune responses at the site where both *M. bovis* and *M. haemolytica* initiate colonization. The two *M. haemolytica* vaccine strains described here significantly decreased middle ear infection ($P<0.05$) and greatly reduced the *M. bovis* lung burden of ($P<3.4E-07$) after experimental challenge.

Figure 3:
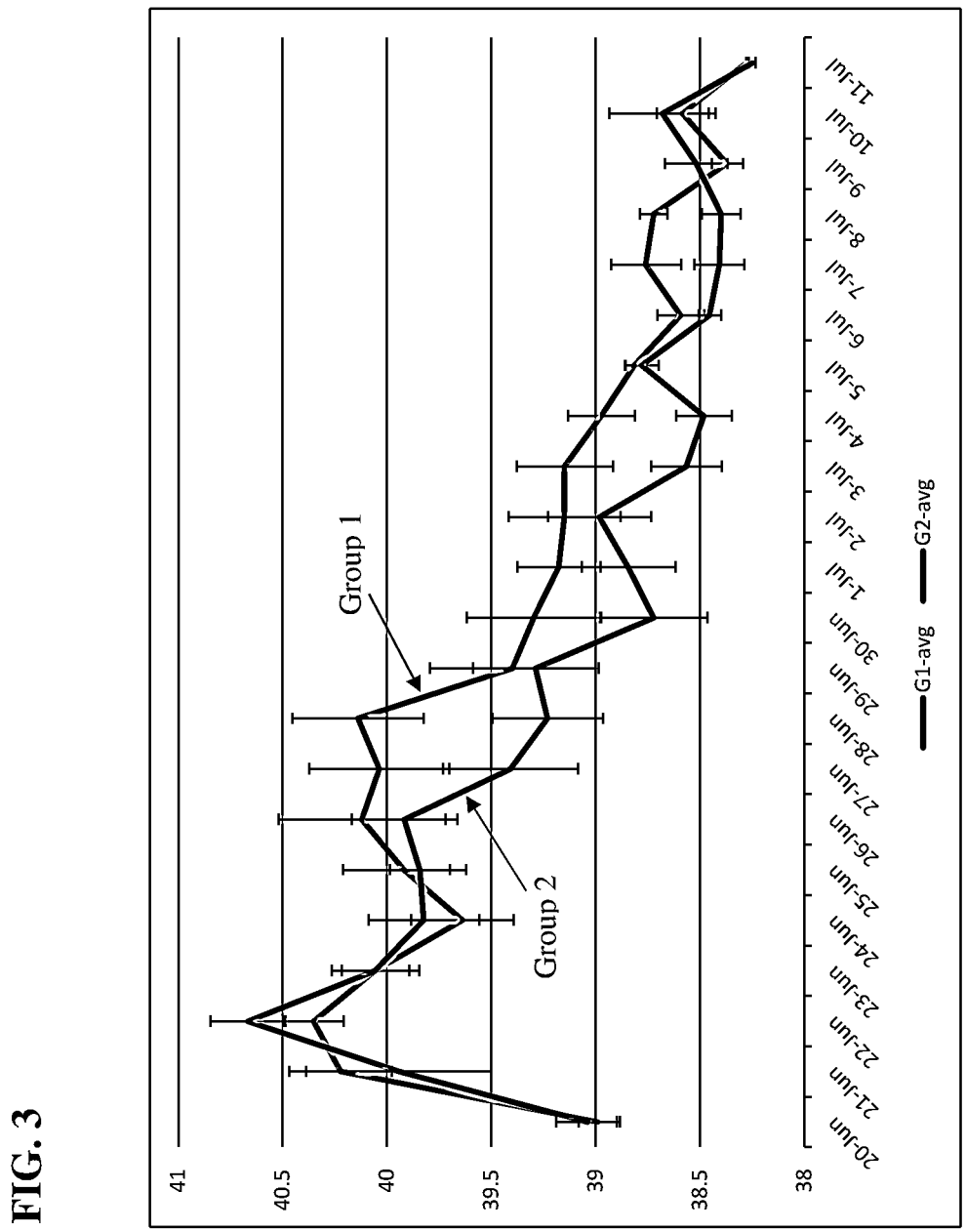
FIG. 3 depicts a graph of the mean rectal temperature of calves challenged with BHV-1, and four days later challenged with *M. bovis*. Group 1, calves were vaccinated with *M. haemolytica* ΔlktCAV4 vaccine product; Group 2, calves vaccinated with ΔlktCAV4Mbovis vaccine product. Error bars represent the standard error of the mean (SEM). The Y axis presents the temperature in degrees Celsius; the X axis presents dates of treatment.
Figure 4:
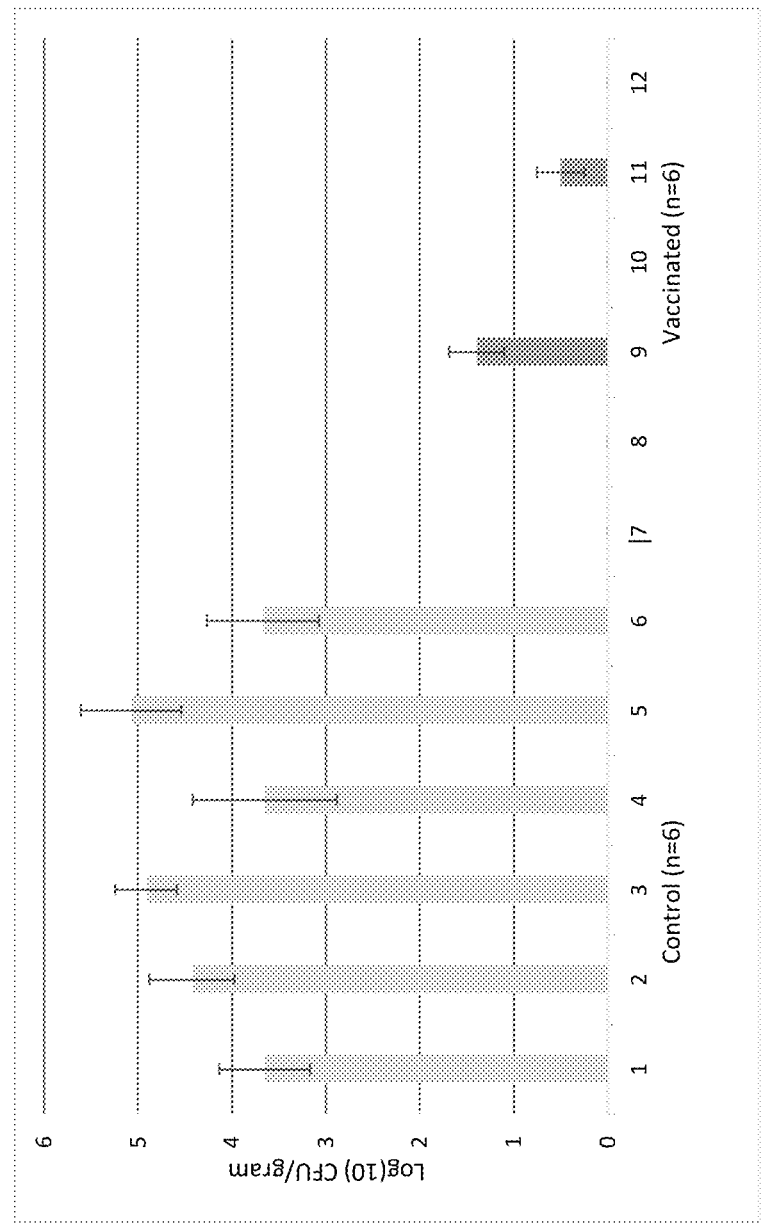
FIG. 4 depicts a graph of the geometric mean quantitative recovery of *M. bovis* from lung specimens. Error bars represent SEM. The Y axis presents the Log(10) cell forming units per gram (Log (10) CFU/gram); the X axis presents the different calves, bars 1 to 6, data from calves vaccinated with *M. haemolytica* ΔlktCAV4; bars 7 to 12, calves vaccinated with ΔlktCAV4Mbovis vaccine product.

In the instant application, a novel delivery system was used where a polynucleotide encoding *M. bovis* antigens was inserted in a modified *M. haemolytica* lktCA gene cluster cassette. A polynucleotide encoding an *M. bovis* chimeric antigen was introduced into the ΔlktCAV4 modified *M. haemolytica* lktCA gene cluster cassette in a replacement plasmid to generate pΔlktCAV4Mbovis replacement plasmid. Attenuated *M. haemolytica* serotype A1 and serotype A6 were obtained following transformation of the wild type *M. haemolytica* serotypes with the pΔlktCAV4Mbovis replacement plasmid. The attenuated bacterial products were named D153ΔlktCAV4Mbovis and D174ΔlktCAV4Mbovis. The attenuated bacterial products were used as vaccine product. A graph of the mean rectal temperature of calves vaccinated with ΔlktCAV4MBovis vaccine product or ΔlktCAV4 vaccine product, challenged with BHV-1, and four days later challenged with *M. bovis* is depicted on FIG. 3. As seen in this graph, the temperatures of the calves in the group vaccinated with ΔlktCAV4 vaccine product (Group 1), and the calves vaccinated with ΔlktCAV4Mbovis vaccine product (Group 2) decreased after a short spike. FIG. 4 shows that *M. bovis* was recovered from the lungs of all the control calves, while only two of the vaccinated calves had low levels of *M. bovis*, and the remaining had no detectable levels of *M. bovis*.

Figure 5:
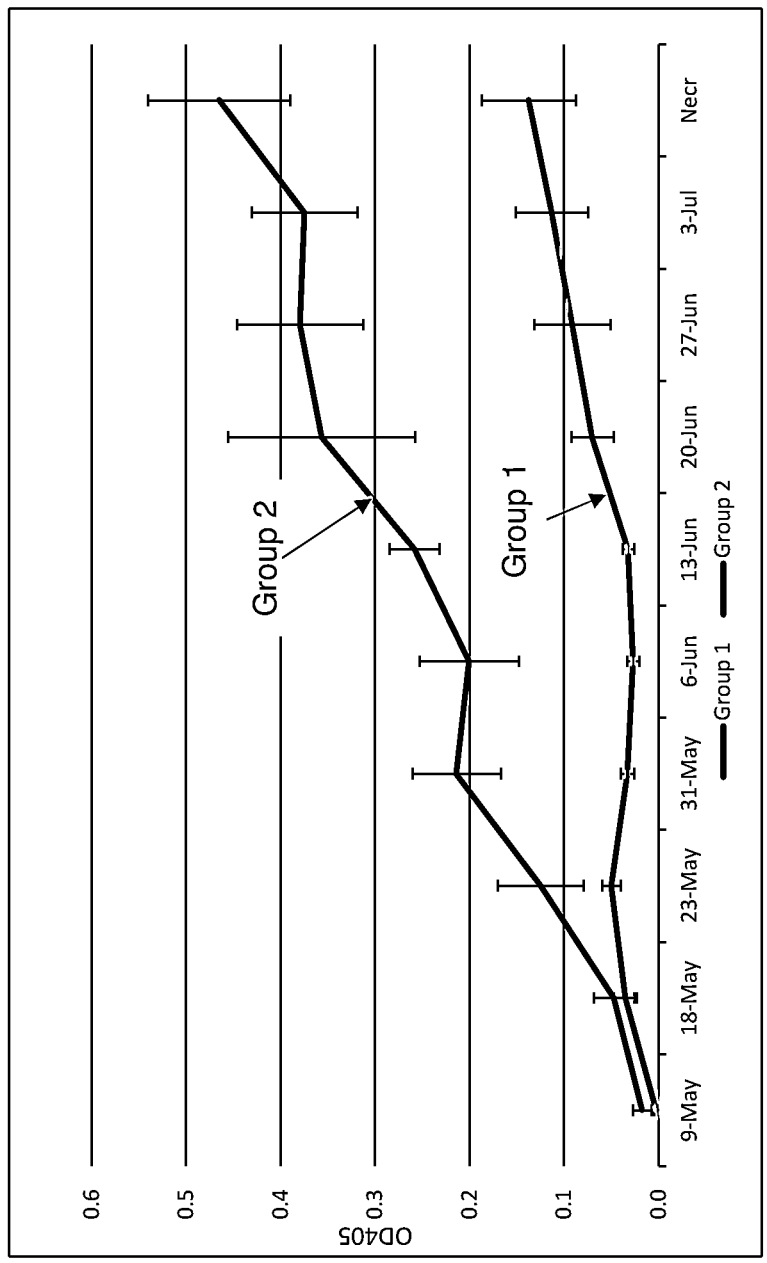
FIG. 5 depicts a graph of the anti-DnaK antibody levels in serum post-vaccination and challenge. Y axis presents the optical density measurements at 405 nm (OD405); X axis presents dates of measurement. Group 1 (ΔlktCAV4 vaccine, no *M. bovis* payload); Group 2 (ΔlktCAV4Mbovis vaccine, with *M. bovis* payload).

As shown in FIG. 5, the DNA K antibody titers of calves vaccinated with ΔlktCAV4 vaccine product and challenged with *M. bovis* were lower than the DNA K antibody titers in calves vaccinated with ΔlktCAV4Mbovis vaccine product and challenged with *M. bovis*. The DNA K antibody titers of these calves trended upwards throughout the trial.

In an embodiment, the invention provides vaccines and immunogenic compositions that, when administered to a subject, elicit an immune response to *M. haemolytica* and/or *M. bovis* in the subject, e.g., a protective immune response. Methods of using the immunogenic compositions/vaccines to prevent or attenuate the spread of *M. haemolytica* and/or *M. bovis* infection in susceptible individuals and/or groups of susceptible individuals are also provided.

Figure 6:
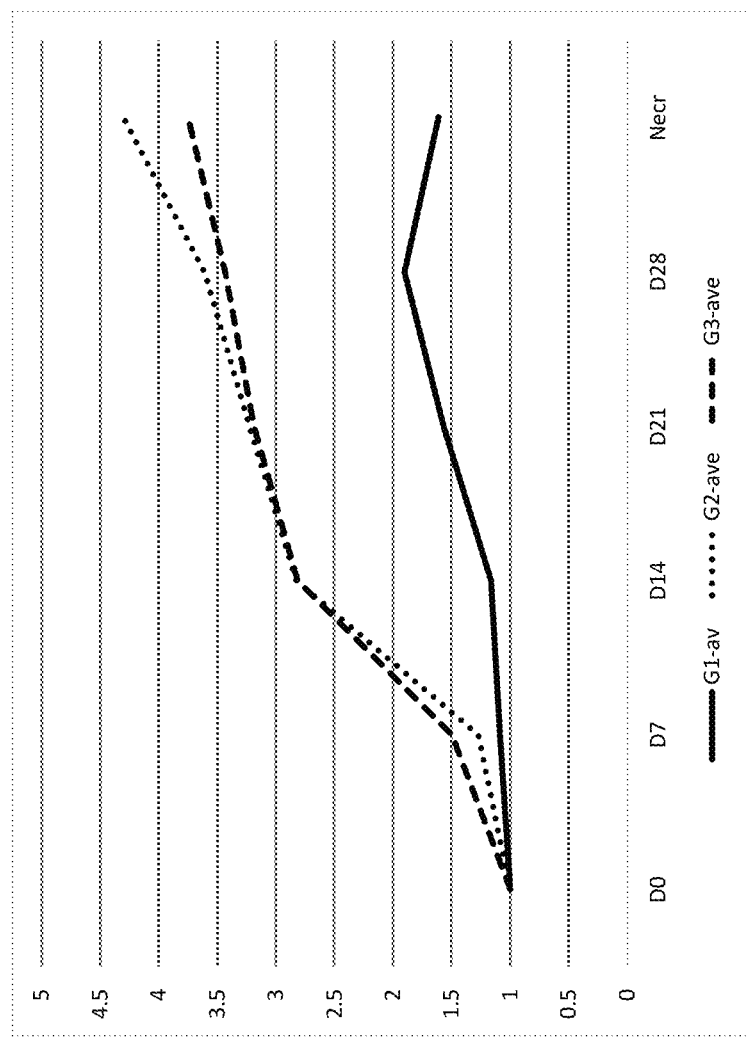
FIG. 6 depicts a graph of the serum IgG1 *Mannheimia* titers in calves challenged with *Mannheimia*. Y axis presents the IgG1 titers; X axis presents the days after treatment. Solid line, averages of Group 1 calves (G1-ave; unvaccinated calves); dotted line, averages of Group 2 calves (G2-ave; calves vaccinated with ΔlktCAV4); dashed line, averages of Group 3 calves (G3-ave; calves vaccinated with ΔlktCAV4Mbovis).
Figure 7:
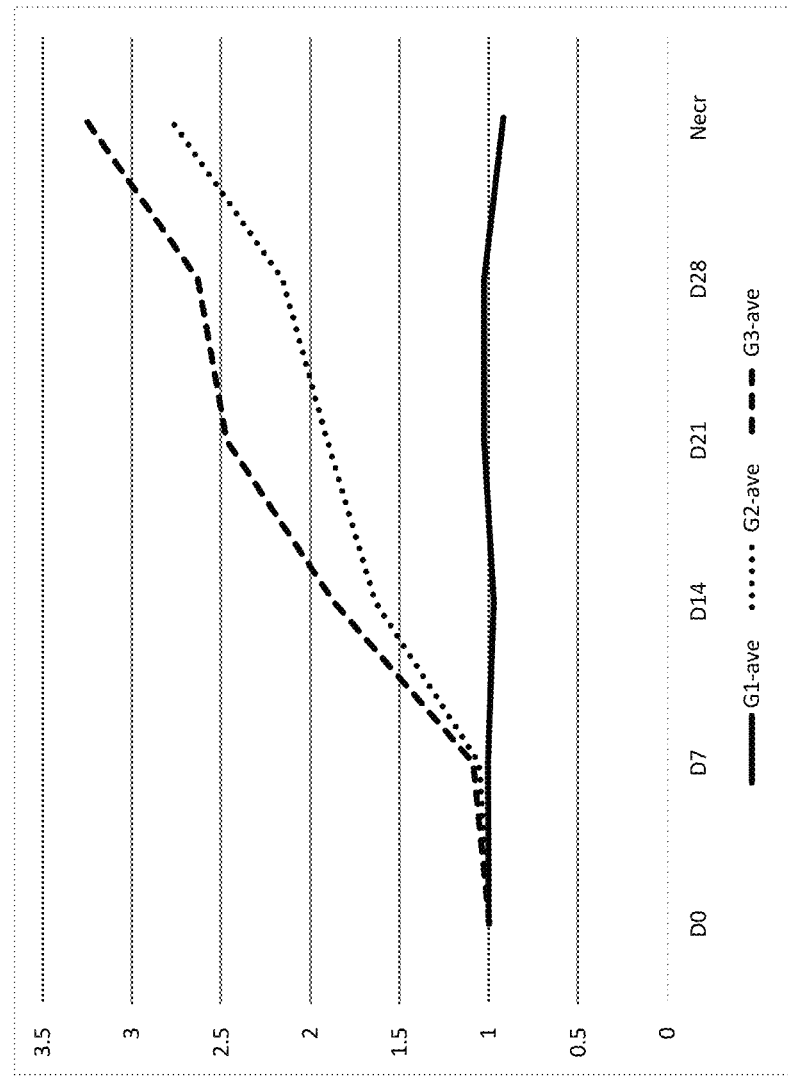
FIG. 7 depicts a graph of the serum IgG2 *Mannheimia* titers in calves challenged with *Mannheimia*. Y axis presents the IgG2 titers; X axis presents the days after treatment. Solid line, averages of Group 1 calves (G1-ave; unvaccinated calves); dotted line, averages of Group 2 calves (G2-ave; calves vaccinated with ΔlktCAV4); dashed line, averages of Group 3 calves (G3-ave; calves vaccinated with ΔlktCAV4Mbovis).
Figure 8:
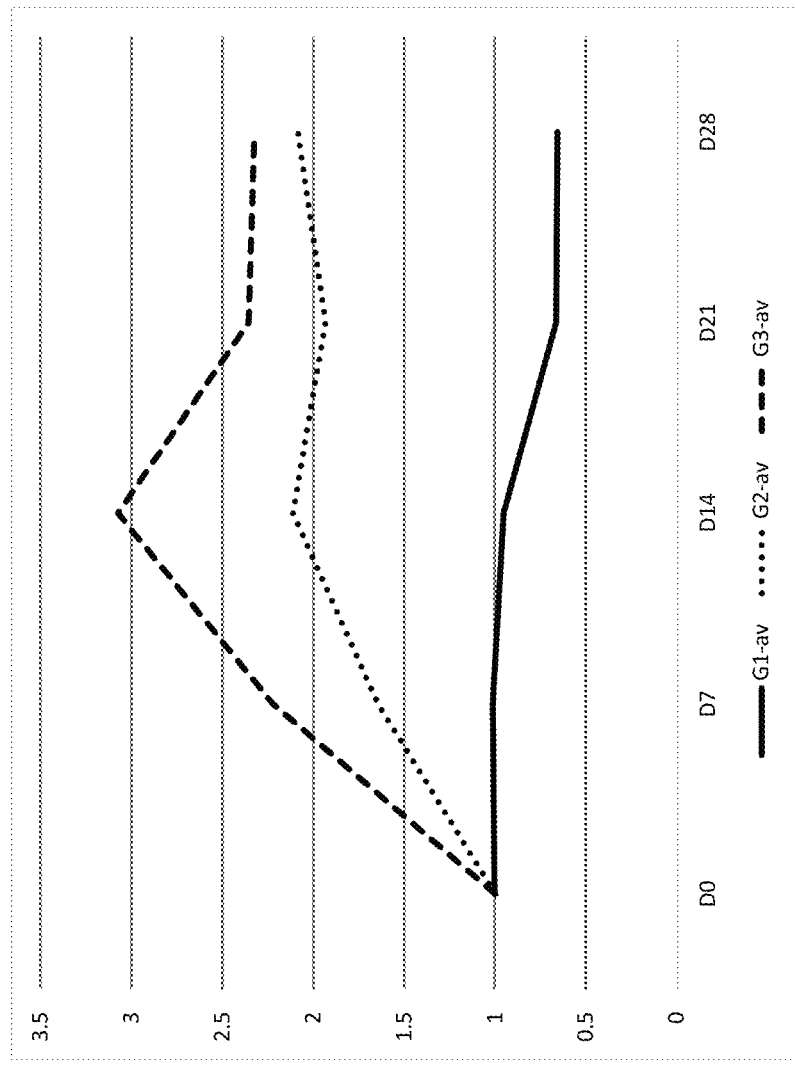
FIG. 8 depicts a graph of the IgG *Mannheimia* titers in tear secretions of calves challenged with *Mannheimia*. Y axis presents the IgG titers; X axis presents the days after treatment. Solid line, averages of Group 1 calves (G1-av; unvaccinated calves); dotted line, averages of Group 2 calves (G2-av; calves vaccinated with ΔlktCAV4); dashed line, averages of Group 3 calves (G3-av; calves vaccinated with ΔlktCAV4Mbovis).
Figure 9:
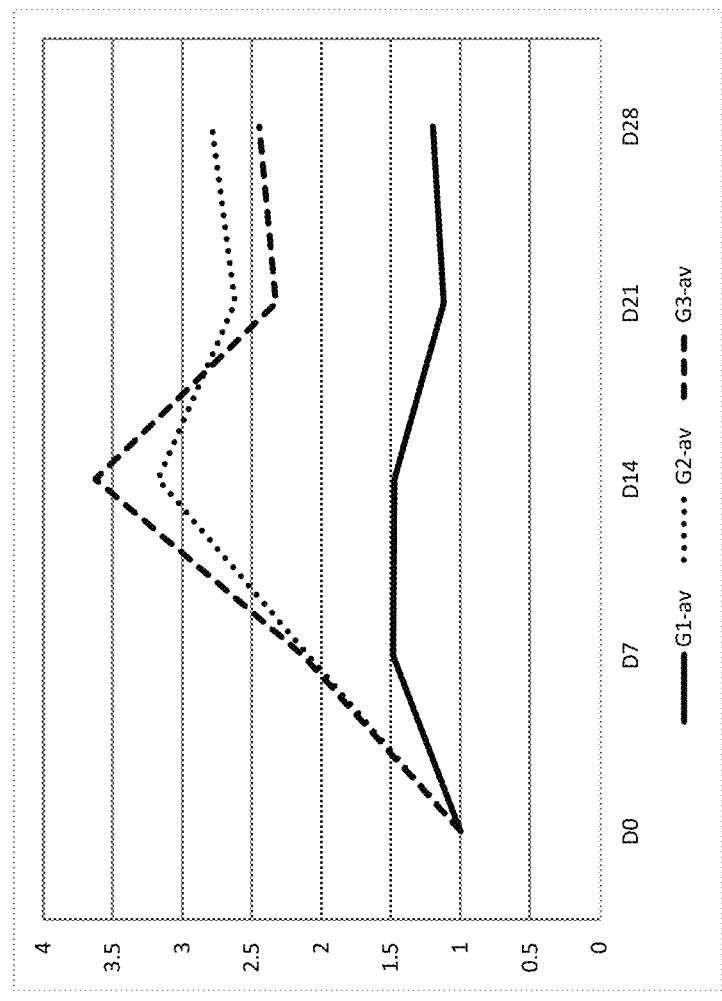
FIG. 9 depicts a graph of the IgA *Mannheimia* titers in tear secretions of calves challenged with *Mannheimia*. Y axis presents the IgG titers; X axis presents the days after treatment. Solid line, averages of Group 1 calves (G1-av; unvaccinated calves); dotted line, averages of Group 2 calves (G2-av; calves vaccinated with ΔlktCAV4); dashed line, averages of Group 3 calves (G3-av; calves vaccinated with ΔlktCAV4Mbovis).

As seen in FIG. 6 and FIG. 7, after *Mannheimia* challenge, the IgG1 and IgG2 *Mannheimia* titers in serum of calves vaccinated with ΔlktCAV4, or ΔlktCAV4Mbovis increased at a higher rate than in unvaccinated calves. Similarly, as seen in FIG. 8 and FIG. 9, after *Mannheimia* challenge, the levels of *Mannheimia* IgG and IgA titers in tear secretions of calves vaccinated with ΔlktCAV4, or ΔlktCAV4Mbovis increased at a higher rate than in unvaccinated calves. Thus, the ΔlktCAV4, or ΔlktCAV4Mbovis may be used to vaccinate cattle against *M. haemolytica*.

The vaccines or immunogenic compositions provided herein can be in the form of modified *M. haemolytica* lktCA gene cluster cassettes involved in evoking an immune response to *M. haemolytica*, or modified *M. haemolytica* lktCA gene cluster cassettes comprising an *M. bovis* antigen, as plasmids or vectors expressing such cassettes, or bacteria expressing such cassettes. In some embodiments of the invention, the cassettes involved in evoking an immune response to *M. bovis* encode at least a fragment of *M. bovis* EF-Tu. In some embodiments of the invention, the cassettes involved in evoking an immune response to *M. bovis* encode at least a fragment of *M. bovis* DnaK. The immunogenic compositions/vaccines provided herein can be used to immunize or treat any mammal, including, but not limited to, cattle, sheep, goats, pigs, bison, elk, camels, dogs, and deer.

In an embodiment, the invention is directed at a vaccine to control *M. bovis* disease, particularly in bison, beef, and dairy cattle. The vaccine may be used for injectable, intranasal, or oral delivery to the recipient animal, and may be combined with other vaccine components such as *Pasteurella multocida*, *Histophilus somni*, and/or viral components such as Bovine herpes virus 1 (BHV-1), parainfluenza virus type 3 (PI3V), and bovine respiratory syncytial virus (BRSV). Depending upon the selected delivery method, protection against *M. haemolytica* may be an intrinsic property of an *M. bovis* vaccine taught here.

In an embodiment, the invention relates to immunogenic compositions/vaccines that can be used to induce an immune response against *M. bovis*. In an embodiment, the invention relates to methods of administering a vaccine as described herein. The methods involve administering an effective amount of a vaccine sufficient to prevent or lessen the extent of development of symptoms of a *M. bovis* in a subject, when the subject is later exposed to the *M. bovis* bacterium, or contacts an *M. bovis* bacterial infection. In some embodiments of the invention the immunogenic composition used to induce response against *M. bovis* is a chimeric Ef-Tu DnaK antigen.

In an embodiment, the invention relates to a vaccine to control *M. bovis*, where the vaccine consists essentially of a modified *M. haemolytica* lktCA gene cluster cassette encoding *M. haemolytica* leuko-toxoid and an *M. bovis* EF-Tu and DnaK chimera. In some embodiments of the invention, the vaccine to control *M. bovis* comprises a modified *M. haemolytica* lktCA gene cluster cassette of the invention with an inserted recombinant polynucleotide encoding *M. bovis* EF-Tu and DnaK. In some embodiments of the invention, the *M. bovis* EF-Tu and DnaK antigen of the invention has the amino acid sequence set forth in SEQ ID NO: 19. In some embodiments of the invention, the *M. bovis* EF-Tu and DnaK antigen is encoded by a polynucleotide having the nucleotide sequence set forth in SEQ ID NO: 18. In some embodiments of the invention, the vaccine to control *M. bovis* encodes a polypeptide having the amino acid sequence set forth in SEQ ID NO: 21. In some embodiments of the invention, the vaccine to control *M. bovis* comprises bacteria with a modified *M. haemolytica* lktCA gene cluster cassette of the invention, comprising the recombinant polynucleotide of SEQ ID NO: 20.

In an embodiment, the invention provides methods for preparing a vaccine to control *M. bovis*. In some embodiments of the invention, such methods include using a modified *M. haemolytica* lktCA gene cluster cassette comprising a recombinant polynucleotide encoding *M. bovis* EF-Tu and *M. bovis* DnaK. In some embodiments of the invention, such methods include transforming bacteria with a nucleic acid comprising a modified *M. haemolytica* lktCA gene cluster cassette encoding *M. bovis* EF-Tu and *M. bovis* DnaK. Transformation can be achieved by any method known in the art, including, for example, electroporation or chemical transformation. A vaccine can be produced using an isolated nucleic acid to transform a bacterial culture. For example, a transformed bacterial culture can overexpress antigens to produce an immune response. In some embodiments, the vaccine to control *M. bovis* is prepared by inserting a recombinant polynucleotide encoding *M. bovis* EF-Tu and DnaK in a modified *M. haemolytica* lktCA gene cluster cassette of the invention.

In some embodiments, a vaccine provided herein can include a marker of delivery and expression. For example, a polynucleotide encoding *M. bovis* EF-Tu and DnaK may include a nucleic acid that encodes a fluorescent polypeptide (e.g., a green fluorescent protein, GFP). The fluorescent polypeptide will serve as a marker of expression and delivery of the vaccine to an animal. For example, a marker of delivery and expression can be detected e.g. as antibodies to the marker. For example, GFP antibodies may be detected in sera from immunized animals.

It is contemplated that virtually any nucleic acid sequence coding for the amino acid sequence that is or includes *M. bovis* EF-Tu and/or *M. bovis* DnaK may be used as described herein. This includes a nucleic acid sequence encoding the amino acid sequence of the full-length EF-Tu and/or DnaK proteins as well as any sequence of, for example from about 5 to about 50 (or less than 5 or more than 50) amino acids at the beginning (amino terminus) or at the end (carboxy terminus) of the amino acid sequence of the EF-TU/DnaK recombinant polypeptide. The amino acid sequences as described herein may also be shortened on either the amino or carboxy terminus (or both) by one, two, or more amino acids to produce fragments within the context of the invention wherein the fragments produce the same or a similar protective effect. Alternatively, the recombinant EF-Tu/DnaK polypeptide may be a chimera or fusion protein which comprises flanking amino acids sequences which are not adjacent to the native sequence in nature. For example, the adjacent sequences may be corresponding amino acids which are from different but related species; or amino acids which are from different species (e.g. from other bacteria or eukaryotes of interest, e.g. from infectious agents); or from a synthetic sequence, e.g. various tags such as histidine or glutathione S-transferase (GST) tags, linkers, spacers, targeting sequences, etc.).

Any effective route of administration may be utilized to deliver the vaccines of the invention, such as, for example, orally, nasally, enterally, parenterally, intramuscularly or intravenously, subcutaneously, intradermally, rectally, vaginally, topically, ocularly, pulmonarily, or by contact application. From a practical standpoint, oral, (intra)nasal, parenteral (IM, SubQ, and perhaps intradermal) and ocular may be preferred. In some embodiments, vaccine compositions of the invention may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes. The vaccines provided herein can be administered using any appropriate method. Administration can be, for example, topical (e.g. transdermal, ophthalmic or intranasal); pulmonary (e.g., by inhalation or insufflation or powders or aerosols); oral, or parenteral (e.g. by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, the mode of administration is intraperitoneal. For application in livestock, the preferred mode of administration is oral.

Vaccine compositions are administered in such amounts and for such time as is necessary to achieve a desired result. As used herein, an "immunogenic" amount of the vaccine composition is an amount which is suitable to elicit an immune response. Thus, the amount effective to treat, attenuate, or prevent disease, as used herein, refers to a nontoxic but sufficient amount of the vaccine composition to treat, attenuate, or prevent disease in any subject. For example, the "therapeutically effective amount" can be an amount to treat, attenuate, or prevent infection (e.g., bacterial infection, *M. bovis* infection), etc. The exact amount required to achieve an "immunogenic amount" may vary, depending on the particular component (e.g., polysaccharide, conjugate), and from subject to subject, depending on the species, age, and general condition of the subject, the stage of the disease, the particular pharmaceutical mixture, its mode of administration, and the like.

The amount of *M. bovis* antigen or modified *M. haemolytica* lktCA gene cluster cassette carrying the *M. bovis* antigen in each vaccine dose is selected to allow the vaccine, when administered as described herein, to induce an appropriate immunoprotective response without significant, adverse side effects. An "immuno-protective" or "protective immune" response as used herein is an immune response sufficient to protect an immunized subject from productive infection by a particular pathogen or pathogens to which a vaccine is directed (e.g., *M. bovis* infection). Optimal amounts of components for a particular vaccine can be ascertained by standard studies involving observation of appropriate immune responses in subjects. Following an initial vaccination, subjects can receive one or several booster immunizations adequately spaced in time. Such amounts may vary depending upon which antigen or antigens are expressed by the modified *M. haemolytica* lktCA gene cluster cassette and/or preparations thereof, and may be formulated in a unit dosage form for ease of administration and uniformity of dosage. The expression "unit dosage form," as used herein, refers to a physically discrete unit of vaccine composition appropriate for the patient to be treated. The specific therapeutically effective dose for any particular patient or organism may depend upon a variety of factors including the severity or degree of risk of infection; the activity of the specific vaccine or vaccine composition employed; other characteristics of the specific vaccine or vaccine composition employed; the age, body weight, general health, sex of the subject, the diet of the subject, the pharmacokinetic condition of the subject, the time of administration (e.g., with regard to other activities of the subject such as eating, sleeping, receiving other medicines including other vaccine doses, etc.), the route of administration, the rate of excretion of the specific vaccine or vaccine composition employed; vaccines used in combination or coincidental with the vaccine composition employed; and like factors well known in the veterinary arts.

M. bovis vaccines for use in accordance with the present invention may be formulated according to known techniques. An immunogenic amount of a vaccine product can be formulated together with one or more pharmaceutically acceptable carrier materials (organic, inorganic, liquid, or solid). In general, pharmaceutically acceptable carriers include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (see also Remington's Pharmaceutical Sciences, Fifteenth Edition, E. W. martin (Mack Publishing Co., Easton Pa., 1975).

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont., USA), alum, mineral gels such as aluminum hydroxide gel, oil-in-water emulsions, water-in-oil emulsions such as, e.g., Freund's complete and incomplete adjuvants, Block copolymer (CytRx, Atlanta, Ga., USA), QS-21 (Cambridge Biotech Inc., Cambridge Mass., USA), SAF-M (Chiron, Emeryville Calif., USA), AMPHIGEN, proprietary oil in water adjuvant (Zoetis, Parsippany, N.J., USA), saponin, Quil A (Brenntag Biosector A/S, Ballerup, Denmark), or other saponin fraction, monophosphoryl lipid A, and Avridine lipid-amine adjuvant. Other immunomodulatory agents that can be included in the vaccine of the invention, comprise, e.g., one or more interleukins, interferons, or other known cytokines.

In some embodiments, at least one booster vaccine, is administered after the initial administration of the vaccine of the invention. The booster vaccine may be identical to the vaccine that is initially used to vaccinate the subject. The booster vaccine may be administered as early as four weeks after initial vaccination. In some embodiments, the booster vaccine may be administered at least one year after initial vaccination.

The immunogenic response from the initial or booster vaccine may protect a naive subject from subsequent full-blown M. bovis infection when exposed to the bacterium. Alternatively, administration of the initial or booster vaccine is used to provide treatment for an existing M. bovis infection. The protective response either wholly or partially prevents or arrests the development of symptoms related to M. bovis disease or bacterial infection, in comparison to a non-vaccinated control organism, in which disease progression is not prevented.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

An effective amount of any of the vaccines described herein can be determined by conventional means, starting with a low dose of chimeric EF-Tu/DnaK polypeptide, M. haemolytica replacement plasmid comprising such chimera, or M. haemolytica bacteria expressing such chimera, and then increasing the dosage while monitoring the effects. An effective amount may be obtained after a single administration of a vaccine or after multiple administrations of a vaccine. Known factors can be taken into consideration when determining an optimal dose per animal. These include the presence of other drugs in the animal, the species, size, age, and general condition of the animal, and the like.

One method of detecting whether an adequate immune response has been achieved is to determine seroconversion and antibody titer in the animal after vaccination. The timing of vaccination and the number of boosters, if any, will preferably be determined by a veterinarian based on analysis of all relevant factors, some of which are described above.

Suitable doses for vaccines according to the practice of the present invention range generally from about $1 \times 10^7$ to about $1.6 \times 10^{10}$ CFU per dose, as may be determined by standard methods. In dairy operations there is an interest in vaccinating cattle as early as 1 day of age. At this very young age, a mucosal delivery route may be preferred. It is also of interest to target the beef segment where 6-8 month old calves are typical recipients of the vaccine.

The effective dose amount of virus, infectious RNA molecule, plasmid, or viral vector, of the present invention can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals.

The present invention further provides methods for preparing a vaccine or immunogenic composition comprising a polynucleotide encoding a chimeric M. bovis EF-Tu/DnaK polypeptide, or a chimeric M. bovis EF-Tu/DnaK polypeptide, or a ΔlktCAV4Mbovis cassette comprising a polynucleotide encoding a chimeric M. bovis EF-Tu/DnaK polypeptide, or a replacement plasmid comprising such a cassette, or bacterial strains comprising such a cassette, or vaccines or immunogenic compositions comprising such a cassette.

The method for preparing such a vaccine may comprise combining an effective amount of a chimeric M. bovis EF-Tu/DnaK polypeptide, an M. hemolytica replacement plasmid comprising a chimeric *M. bovis* EF-Tu/DnaK insert, or bacterial strains described herein, with a carrier acceptable for pharmaceutical or veterinary use.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples. Numerous modifications and variations of the present invention are possible in light of the above teachings and, therefore, are within the scope of the invention.

The invention is directed at a vaccine to control *M. bovis*, particularly in beef, dairy cattle, and bison. The vaccine is intended for injectable, intra-nasal, or oral delivery to the recipient animal and may be combined with other vaccine components such as *Pasteurella multocida, Histophilus somni*, and/or viral components such as BHV-1, PI-3V, and BRSV. Depending upon the selected delivery method, protection against *M. haemolytica* may be an intrinsic property of a vaccine comprising the *M. haemolytica* replacement vector taught here.

The vaccine may be delivered as a modified-live vectored product via an attenuated *M. haemolytica* vaccine strain as tested here, or as a killed vaccine strain, or as a subunit vaccine product, or as a DNA vaccine. The *M. haemolytica* replacement vector utilized here consists of a gene-knockout modified which targeted the leukotoxin operon. *M. haemolytica* which does not express an active leukotoxin is dramatically attenuated in lung tissue, but remains capable of colonizing the nasopharynx where it can elicit an immune response. Because leukotoxin itself is an important immunogen, the vaccine strain is designed to express an inactive but immunogenic form of the protein—a genetic toxoid. Within the modified leukotoxin operon was placed an MfeI restriction site specifically for cloning of DNA, allowing heterologous DNA (preferably encoding protective immunogenic epitopes) to be cloned and expressed as a fusion product with the leuko-toxoid. In this case, DNA encoding fragments of *M. bovis* EF-Tu and DnaK (HsP70) were cloned in-frame into the MfeI restriction site.

Nucleotide sequences encoding *M. bovis* EF-Tu and DnaK were codon-optimized. DNA encoding the chimeric protein was synthesized by Blue Heron Biotech (Bothell, Wash., USA). The 5' end was designed with nucleotides corresponding to an Mfe1 restriction endonuclease recognition site, and the 3' end was designed with nucleotides corresponding to an EcoR1 restriction endonuclease recognition site to allow cloning into a replacement plasmid containing Mfe1 at the cloning site. After cloning, the resultant plasmid was utilized to generate modified *Mannheimia haemolytica* serotype 1 and serotype 6.

In some embodiments of the invention, a vaccine provided herein can be delivered as a prophylactic vaccine to reduce the risk of developing *M. bovis* disease, should a *Mycoplasma bovis* infection occur. In some instances, a vaccine provided herein can reduce the risk of developing infection by *M. bovis* bacteria. A vaccine provided herein can also be delivered as a prophylactic vaccine to reduce the risk of developing *M. bovis* disease should an *M. bovis* infection occur.

Although mucosal vaccination and leukotoxin deficient *M. haemolytica* are known, inventors are aware of no *M. haemolytica* vectors successfully combining the concepts disclosed herein.

EF-Tu is a prokaryotic elongation factor responsible for catalyzing the binding of an aminoacyl-tRNA to the ribosome. It is a G-protein, and facilitates the selection and binding of an aa-tRNA to the A-site of the ribosome.

All living organisms respond to environmental stresses such as high temperature by synthesizing a set of proteins which have been called heat shock proteins (Hsps). Some of them are highly conserved in the course of evolution, especially the proteins encoded by the groEL(hsp60 or cpn60) and the dnaK(hsp70) genes.

Molecular chaperones are a diverse family of proteins that function to protect proteins in the intracellular milieu from irreversible aggregation during synthesis and in times of cellular stress. The bacterial molecular chaperone DnaK is an enzyme that couples cycles of ATP binding, hydrolysis, and ADP release by an N-terminal ATP-hydrolysing domain to cycles of sequestration and release of unfolded proteins by a C-terminal substrate binding domain. In prokaryotes, the grpE protein is a co-chaperone for DnaK, and acts as a nucleotide exchange factor, stimulating the rate of ADP release 5000-fold.

The majority of *Mannheimia* strains isolated from pulmonary infection in cattle belongs to *M. haemolytica* serotype A1/A6. These strains are sub-dominant to other *M. haemolytica* serotypes in the nasopharynx of healthy cattle, but dominate when the host defenses are at least partly compromised. In the immunocompromised host, they have an increased capacity for proliferation and can achieve relatively high total numbers in the nasopharynx, where they are likely to be transmitted to the nasopharynx of new hosts or to spill over or otherwise enter the lungs. However, pulmonary infection caused by *M. haemolytica* serotype A1 is considered to be non-communicable (i.e. no direct transmission between the lungs) and the continuous circulation of these bacteria in bovine populations seems to depend on their capacity for asymptomatic transmission to the nasopharynx, and not the lungs, of new hosts.

As used herein, "modified *M. haemolytica* lktCA gene cluster vector" and "replacement *M. haemolytica* plasmid" are used interchangeably and refer to a mutated *M. haemolytica* lktCA gene cluster comprising a polynucleotide encoding an added neutralizing epitope inserted downstream of the lktC-lktA intergenic region, and upstream of lktA gene nucleotide 2192. In some embodiments, the modified *M. haemolytica* lktCA gene cluster vector comprises a leukotoxin promotor, an lktC/lktA intergenic region, a polynucleotide encoding an added neutralizing epitope inserted downstream of the lktC-lktA intergenic region, and upstream of lktA gene nucleotide 2192, and lktA nucleotides 2192 to 2862.

In an embodiment, the invention relates to a method for vaccinating an animal. The method comprises administering to an animal an effective amount of a composition comprising a modified *M. haemolytica* lktCA gene cluster cassette comprising a polynucleotide encoding an additional leukotoxin neutralizing epitope. In some embodiments of the invention, the vaccine comprises a cassette of the invention and pharmaceutically acceptable carrier, excipient, or vehicle. In some embodiments of the invention, the animal is an even toed ungulate ruminant. In some embodiments of the invention, the vaccinated animal may be a cattle, a sheep, a goat, a deer, a giraffe, an elk, or a bison.

In an embodiment, the invention relates to a kit for performing methods of eliciting or inducing an immunogenic or protective response against a bacterial antigen. In some embodiments of the invention, the kit comprises a modified *M. haemolytica* lktCA gene cluster vector comprising a polynucleotide encoding an added neutralizing epitope. In some embodiments of the invention the added neutralizing epitope is inserted downstream of the lktC-lktA intergenic region, and upstream of lktA gene nucleotide 2192. In some embodiments of the invention, the kit comprises a polynucleotide encoding a polypeptide with the amino acid sequence set forth in SEQ ID NO: 13. In some embodiments of the invention, the kit comprises a polynucleotide with the nucleotide sequence set forth in SEQ ID NO: 12.

In an embodiment, the invention relates to a kit comprising a modified *M. haemolytica* lktCA gene cluster cassette comprising a polynucleotide encoding an added neutralizing epitope. In some embodiments, the modified *M. haemolytica* lktCA gene cluster cassette comprises a polynucleotide encoding at least one heterologous antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and comprises a polynucleotide encoding at least one heterologous antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding a heterologous antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding a heterologous antigen.

In an embodiment, the invention relates to a kit comprising a modified *M. haemolytica* lktCA gene cluster cassette comprising a polynucleotide encoding an added neutralizing epitope and comprises a polynucleotide encoding at least one *M. bovis* antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding an *M. bovis* chimeric antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding *M. bovis* DnaK and *M. bovis* EF-Tu. In some embodiments of the invention, the kit comprises a polynucleotide encoding the amino acid sequence set forth in SEQ ID NO: 21. In some embodiments of the invention, the kit comprises a polynucleotide with the sequence set forth in SEQ ID NO: 20.

The terms "antigen," "antigenic region," and "immunogen," may be used interchangeably herein. As used herein, an antigen or immunogen, or epitope is generally a portion of a protein (e.g. a peptide or polypeptide). Antigen is a term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

As used herein, an "antigen" or "immunogen" is a substance that induces a specific immune response in a host animal. The antigen may comprise a whole organism either killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

An "immunological response" to a composition or vaccine is the development in the host of a cellular and/or antibody-mediated immune response to a composition or vaccine of interest. Usually, an "immunological response" includes, but is not limited to, one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of cattle, sheep, goats, pigs, bison, elk, camels, dogs, and deer. The term "animal" also includes an individual animal in all stages of development, including newborn, embryonic and fetal stages.

As used herein, the term "about" is defined as plus or minus ten percent of a recited value. For example, about 1.0 g means 0.9 g to 1.1 g.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual

EXAMPLES

Having now generally described this invention, the same will be better understood by reference to certain specific examples, which are included herein only to further illustrate the invention and are not intended to limit the scope of the invention as defined by the claims.

Example 1

Construction Modified *M. haemolytica* lktCA Gene Cluster Cassette

A modified *M. haemolytica* lktCA gene cluster cassette with an insertion of a polynucleotide encoding an additional *M. haemolytica* leukotoxin neutralizing epitope was prepared.

The polynucleotide cassette was designed to delete parent chromosomal nucleotides from the beginning of the lktC ribosome binding site to the beginning of the lktA ribosome binding site, thereby removing the entire lktC coding region. A second deletion was designed in-frame with the lktA coding region to remove the nucleotides encoding amino acids 2 to 731. A synthetic codon-optimized polynucleotide encoding the leukotoxin neutralizing epitope, flanked upstream by a synthetic MfeI site and downstream by a synthetic BamH1 site, was inserted in-frame with the second deletion, thereby duplicating the neutralizing epitope in the encoded leukotoxoid product. A schematic of the preparation of the modified *M. haemolytica* lktCA gene cluster cassette is depicted on FIG. 1.

The nucleotide sequence of the wild-type *M. haemolytica* D153 lktCA gene cluster is

```
ttctcttttgctaaatagtgttggtaagtagtcccattttgcacaccaatcgttttcaccttagcaaaatctgtatctttttcgcaatgaaggcagc agagcttggaaagtaaggctcgctaaataatacttgtttcttacgtggttccgtaatacccatacctgaaattgcagcatcaaattgtttttgtttta ggctttggattaagctatcaaaaggttggctatggaatgtacaatttgcattcatctctttacagatagcatttgcaatatccacatcaaaaccgata atttctcccttctcttcggtcatttcaaatggaggatagcttggctccatcacaaatttgatatcttgtgcctgcgcagtaaccacacacccgaata aaagggtcaaaagtgttttttcataaaaagtccctgtgttttcattataaggattaccactttaacgcagttactttcttaaaaaagtcttcttt cataaagtttgttttatgtcatacaaacacatcaaattgagatgtagtttctcaatcctcttgattcctctatctcaaaaaaacaacccaaaagaaa aagaaaagtatatgttacattaatattacaatgtaattattttgtttaatttccctacatttgtataactttaaaacactccttttctcttctgat tatataaaagacaaaaaatacaattaagctacaaaaaacaacaaaaaacaacaaaaaacacgacaataagatcgagtaatgattatattatgttata atttttgacctaatttagaataattatcgagtgcaaattATGaatcaatcttattttaacttactaggaaacattacttggctatggatgaactcctc cctccacaaagaatggagctgtgaactactagcacgcaatgtgattcctgcaattgaaaatgaacaatatatgctacttatagataacggtattccga tcgcttattgtagttgggcagatttaaaccttgagactgaggtgaaatatattaaggatattaattcgttaacaccagaagaatggcagtctggtg acagacgctggattattgattgggtagcaccattcggacattctcaattactttataaaaaaatgtgtcagaaataccctgatatgatcgtcagat ctatacgcttttatccaaagcagaaagaattaggcaaaattgcctactttaaaggaggtaaattagataaaaaaacagcaaaaaaacgttttga tacatatcaagaagagctggcaacagcacttaaaaatgaatttaatttttattaaaaaatagaaggagacatcccttATGggaactagacttac aaccctatcaaatgggctaaaaaacactttaacggcaaccaaaagtggcttacataaagccggtcaatcattaacccaagccggcagttcttt aaaaactggggcaaaaaaattatcctctatattccccaaaattaccaatatgatactgaacaaggtaatggtttacaggatttagtcaaagcg gccgaagagttggggattgaggtacaaagagaagaacgcaataatattgcaacagctcaaaccagtttaggcacgattcaaaccgctattg gcttaactgagcgtggcattgtgttatccgctccacaaattgataaattgctacagaaaactaaagcaggccaagcattaggttctgccgaaa gcattgtacaaaatgcaaataaagccaaaactgtattatctggcattcaatctattttaggctcagtattggctggaatggatttagatgaggcct tacagaataacagcaaccaacatgctcttgctaaagctggcttggagctaacaaattcattaattgaaatattgctaattcagtaaaaacactt gacgaatttggtgagcaaattagtcaatttggttcaaaactacaaaatatcaaaggcttagggactttaggagacaaactcaaaaatatcggtg gacttgataaagctggccttggtttagatgttatctcagggctattcgggcgcaacagctgcacttgtacttgcagataaaaatgcttcaaca gctaaaaaagtgggtgcgggttttgaattggcaaaccaagttgttggtaatattaccaaagccgtttcttcttacattttagcccaacgtgttgca gcaggtttatcttcaactgggcctgtggctgctttaattgcttctactgtttctcttgcgattagcccattagcatttgccggtattgccgataaatt taatcatgcaaaaagtttagagagttatgccgaacgctttaaaaaattaggctatgacggagataatttattagcagaatatcagcggggaaca gggactattgatgcatcggttactgcaattaataccgcattggccgctattgctggtggtgtgtctgctgctgcagccggctcggttattgcttc accgattgccttattagtatctgggattaccggtgtaatttctacgattctgcaatattctaaacaagcaatgtttgagcacgttgcaaataaattc ataacaaaattgtagaatgggaaaaaaataatcacggtaagaactactttgaaaatggttacgatgcccgttatcttgcgaatttacaagataat atgaaattcttactgaacttaaacaaagagttacaggcagaacgtgtcatcgctattactcagcagcaatgggataacaacattggtgatttag
```

-continued ctggtattagccgtttaggtgaaaaagtccttagtggtaaagcctatgtggatgcgtttgaagaaggcaaacacattaaagccgataaattagt acagttggattcggcaaacggtattattgatgtgagtaattcgggtaaagcgaaaactcagcatatcttattcagaacgccattattgacgccg ggaacagagcatcgtgaacgcgtacaaacaggtaaatatgaatatattaccaagctcaatattaaccgtgtagatagctggaaaattacagat ggtgcagcaagttctacctttgatttaactaacgttgttcagcgtattggtattgaattagacaatgctggaaatgtaactaaaaccaaagaaac aaaaattattgccaaacttggtgaaggtgatgacaacgtatttgttggttctggtacgacggaaattgatggcggtgaaggttacgaccgagtt cactatagccgtggaaactatggtgctttaactattgatgcaaccaaagagaccgagcaaggtagttataccgtaaatcgtttcgtagaaacc ggtaaagcactacacgaagtgacttcaacccataccgcattagtgggcaaccgtgaagaaaaaatagaatatcgtcatagcaataaccagc accatgccggttattacaccaaagatacctttgaaagctgttgaagaaattatcggtacatcacataacgatatctttaaaggtagtaagttcaat gatgcctttaacggtggtgatggtgtcgatactattgacggtaacgacggcaatgaccgcttatttggtggtaaaggcgatgatattctcgatg gtggaaatggtgatgatttatcgatggcggtaaaggcaacgacctattacacggtggcaagggcgatgatattttcgttcaccgtaaaggcg atggtaatgatattattaccgattctgacggcaatgataaattatcattctctgattcgaacttaaaagatttaacatttgaaaaagttaaacataat cttgtcatcacgaatagcaaaaagagaaagtgaccattcaaaactggttccgagaggctgattttgctaaagaagtgcctaattataaagca actaaagatgagaaaatcgaagaaatcatcggtcaaaatggcgagcggatcacctcaaagcaagttgatgatcttatcgcaaaaggtaacg gcaaaattacccaagatgagctatcaaaagttgttgataactatgaattgctcaaacatagcaaaaatgtgacaaacagcttagataagttaat ctcatctgtaagtgcatttacctcgtctaatgattcgagaaatgtattagtggctccaacttcaatgttggatcaaagtttatcttctcttcaatttg ctagagcagcttaattttttaatgattggcaactctatattgtttcacacattatagagttgccgttttattttataaaaggagacaatatggaagcta accatcaaaggaatgatcttggtttagttgccctcactatgttggcacaataccataatatttcgcttaatccggaa, and is set forth in SEQ ID NO: 1.

A Down-Replacement arm and an Up-Replacement arm were created to introduce the changes in the *M. haemolytica* lktCA gene cluster. The Down-Replacement arm was generated by amplifying a portion of the *M. haemolytica* D153 lktCA gene cluster using polymerase chain reaction (PCR). The nucleotide sequence of the Down-arm Forward primer TM56 is AAAGGATCCTTTAACGGTGGTGAT; and is set forth in SEQ ID NO: 3. This Down-arm Forward primer TM56 added nucleotides corresponding to a BamHI restriction endonuclease recognition site at the 5' end of the Down-replacement arm. The nucleotide sequence of the Down-arm Reverse primer TM57 is AAAGAATTCCGGATTAAGCGAAATATTATGGTA TTGT; and is set forth in SEQ ID NO: 4. This Down-arm Reverse primer TM57 added nucleotides corresponding to an EcoRI restriction endonuclease recognition site at the 3' end of the Down-replacement arm. Thus, in a 5' to 3' orientation, the Down-Replacement arm contained nucleotides corresponding to a BamHI restriction endonuclease recognition site, followed by nucleotides 3530 to 4360 of the *M. haemolytica* D153 lktCA gene cluster of SEQ ID NO: 1, followed by nucleotides corresponding to an EcoRI restriction endonuclease recognition site. The nucleotide sequence of the amplified Down-replacement arm is

GGATCCTTTAACGGTGGTGATGGTGTCGATACTATTGACGGTAACGACG

GCAATGACCGCTTATTTGGTGGTAAAGGCGATGATATTCTCGATGGTGG

AAATGGTGATGATTTTATCGATGGCGGTAAAGGCAACGACCTATTACAC

GGTGGCAAGGGCGATGATATTTTCGTTCACCGTAAAGGCGATGGTAATG

ATATTATTACCGATTCTGACGGCAATGATAAATTATCATTCTCTGATTC

GAACTTAAAAGATTTAACATTTGAAAAGTTAAACATAATCTTGTCATC

ACGAATAGCAAAAAGAGAAAGTGACCATTCAAAACTGGTTCCGAGAGG

CTGATTTTGCTAAAGAAGTGCCTAATTATAAAGCAACTAAAGATGAGAA

AATCGAAGAAATCATCGGTCAAAATGGCGAGCGGATCACCTCAAAGCAA

GTTGATGATCTTATCGCAAAAGGTAACGGCAAAATTACCCAAGATGAGC

TATCAAAAGTTGTTGATAACTATGAATTGCTCAAACATAGCAAAAATGT

GACAAACAGCTTAGATAAGTTAATCTCATCTGTAAGTGCATTTACCTCG

TCTAATGATTCGAGAAATGTATTAGTGGCTCCAACTTCAATGTTGGATC

AAAGTTTATCTTCTCTTCAATTTGCTAGAGCAGCTTAATTTTTAATGAT

TGGCAACTCTATATTGTTTCACACATTATAGAGTTGCCGTTTTATTTTA

TAAAAGGAGACAATATGGAAGCTAACCATCAAAGGAATGATCTTGGTTT

AGTTGCCCTCACTATGTTGGCACAATACCATAATATTTCGCTTAATCCG

GAATTC, and is set forth in SEQ ID NO: 2.

Plasmid PBCSKlktDown was generated by subjecting the amplified Down-replacement arm PCR product to digestion with restriction endonuclease enzymes EcoRI and BamHI. After purification of the digested product, it was inserted into the corresponding sites of the pBC SK(−) cloning vector (Stratagene California; La Jolla, Calif., USA).

The Up-Replacement arm was synthesized by Blue Heron Biotech (Bothell, Wash., USA). In a 5' to 3' orientation, the synthesized Up-Replacement arm contained nucleotides corresponding to a BamHI restriction endonuclease recognition site, followed by nucleotides 1 to 807 and 1325 to 1341 of the *M. haemolytica* D153 lktCA gene cluster nucleotide sequence set forth in SEQ ID NO: 1, followed by nucleotides corresponding to an MfeI restriction endonuclease recognition site, followed by a codon-optimized sequence encoding the added leukotoxin neutralizing epitope, followed by nucleotides corresponding to a BamHI restriction endonuclease recognition site. The nucleotide sequence of the synthesized Up-Replacement arm is GGATCCGAATTCTCTTTTGCTAAATAGTGTTGGTAAGTAGTCCCATTTT
GCACACCAATCGTTTTCACCTTAGCAAAATCTGTATCTTTTTTCGCAAT
GAAGGCAGCAGAGCTTGGAAAGTAAGGCTCGCTAAATAATACTTGTTTC
TTACGTGGTTCCGTAATACCCATACCTGAAATTGCAGCATCAAATTGTT
TTTGTTTTAGGCTTTGGATTAAGCTATCAAAAGGTTGGCTATGGAATGT
ACAATTTGCATTCATCTCTTTACAGATAGCATTTGCAATATCCACATCA
AAACCGATAATTTCTCCCTTCTCTTCGGTCATTTCAAATGGAGGATAGC
TTGGCTCCATCACAAATTTGATATCTTGTGCCTGCGCAGTAACCACACA
CCCGAATAAAAGGGTCAAAAGTGTTTTTTTCATAAAAAGTCCCTGTGTT
TTCATTATAAGGATTACCACTTTAACGCAGTTACTTTCTTAAAAAAAGT
CTTCTTTTCATAAAGTTTGTTTTATGTCATACAAACACATCAAATTGAG
ATGTAGTTTCTCAATCCTCTTGATTCCTCTATCTCAAAAAAACAACCCA
AAAGAAAAAGAAAAGTATATGTTACATTAATATTACAATGTAATTATT
TTGTTTAATTTCCCTACATTTTGTATAACTTTAAAACACTCCTTTTTCT
CTTCTGATTATATAAAAGACAAAAAATACAATTTAAGCTACAAAAAACA
ACAAAAAACAACAAAAAACACGACAATAAGATCGAGTAATGATTATATT
ATGTTATAATTTTTGACCTAATTTAGAATAATTATAGGAGACATCCCTT
ATGCAATTGGTAATTACAAATAGCAAAAAAGAAAAAGTAACAATTCAAA
ATTGGTTTCGTGAAGCAGATTTCGCTAAAGAAGTTCCAAATTATAAAGC
AACGAAGGATGAAAAAATTGAAGAAATTATTGGACAAAATGGAGAACGT
ATTACAAGTAAACAAGTAGATGACTTAATCGCAAAAGGTAACGGAAAAA
TTACTCAGGATGAATTATCGAAGGTGGTAGATAACTATGAAGGATCC, and is set forthin SEQ ID NO: 5.

Plasmid pBCSKlktUp-Down was generated by inserting the synthetic Up-Replacement arm into BamH1-digested pBCSKlktDown. The correct orientation of the Up-Replacement arm was determined using standard Sanger DNA sequencing (performed at the Iowa State University DNA facilities in Ames, Iowa, USA). The resulting pBCSKlktUp-Down plasmid contains the ΔlktCAV4 cassette.

A depiction of the modified lktCA gene cluster cassette is shown in FIG. 1. The top portion of the figure depicts the *M. haemolytica* leukotoxin lktCA gene cluster, which contains the lkt promotor region (grey arrow); the lktC gene open reading frame (black arrow); the lktC-lktA intergenic region (white arrow); the lktA gene open reading frame (dotted arrow); the added lkt neutralizing epitope (NE, striped slashes), and brackets showing the sections of the lktCA gene cluster to be deleted. The lktA open reading frame includes nucleotides encoding the LktA glycine rich region (GRR, diagonal bricks) and the NE (alternating horizontal dashes). The bottom portion of the figure depicts the *M. haemolytica* ΔlktCAV4 cassette, which contains the lkt promotor region (grey arrow), having the nucleotide sequence TTCTCTTTTGCTAAATAGTGTTGGTAAGTAGTCCCATTTTGCACACCAA
TCGTTTTCACCTTAGCAAAATCTGTATCTTTTTTCGCAATGAAGGCAGC
AGAGCTTGGAAAGTAAGGCTCGCTAAATAATACTTGTTTCTTACGTGGT
TCCGTAATACCCATACCTGAAATTGCAGCATCAAATTGTTTTTGTTTTA
GGCTTTGGATTAAGCTATCAAAAGGTTGGCTATGGAATGTACAATTTGC
ATTCATCTCTTTACAGATAGCATTTGCAATATCCACATCAAAACCGATA
ATTTCTCCCTTCTCTTCGGTCATTTCAAATGGAGGATAGCTTGGCTCCA
TCACAAATTTGATATCTTGTGCCTGCGCAGTAACCACACACCCGAATAA
AAGGGTCAAAAGTGTTTTTTTCATAAAAAGTCCCTGTGTTTTCATTATA
AGGATTACCACTTTAACGCAGTTACTTTCTTAAAAAAAGTCTTCTTTTC
ATAAAGTTTGTTTTATGTCATACAAACACATCAAATTGAGATGTAGTTT
CTCAATCCTCTTGATTCCTCTATCTCAAAAAAACAACCCAAAAGAAAAA
AGAAAAGTATATGTTACATTAATATTACAATGTAATTATTTTGTTTAAT
TTCCCTACATTTTGTATAACTTTAAAACACTCCTTTTTCTCTTCTGATT
ATATAAAGACAAAAAATACAATTTAAGCTACAAAAAACAACAAAAAAC
AACAAAAAACACGACAATAAGATCGAGTAATGATTATATTATGTTATAA
TTTTTGACCTAATTTAGAATAATTAT, which is set forth in SEQ ID NO: 6;

the lktC-lktA intergenic region (white arrow), having the nucleotide sequence AAGGAGACATCCCTT, set forth in SEQ ID NO: 7; the added codon-optimized lkt NE (striped slashes) having the nucleotide sequence CAATTGGTAATTACAAATAGCAAAAAAGAAAAAGTAACAATTCAAAATT
GGTTTCGTGAAGCAGATTTCGCTAAAGAAGTTCCAAATTATAAAGCAAC
GAAGGATGAAAAAATTGAAGAAATTATTGGACAAAATGGAGAACGTATT
ACAAGTAAACAAGTAGATGACTTAATCGCAAAAGGTAACGGAAAAA
TTACTCAGGATGAATTATCGAAGGTGGTAGATAACTATGAAGGATCC, set forth in SEQ ID NO: 8;

and leukotoxin A nucleotides 2192 to 3022

CCTTTAACGGTGGTGATGGTGTCGATACTATTGACGGTAACGACGGCAA
TGACCGCTTATTTGGTGGTAAAGGCGATGATATTCTCGATGGTGGAAAT
GGTGATGATTTTATCGATGGCGGTAAAGGCAACGACCTATTACACGGTG
GCAAGGGCGATGATATTTTCGTTCACCGTAAAGGCGATGGTAATGATAT
TATTACCGATTCTGACGGCAATGATAAATTATCATTCTCTGATTCGAAC
TTAAAAGATTTAACATTTGAAAAAGTTAAACATAATCTTGTCATCACGA
ATAGCAAAAAAGAGAAAGTGACCATTCAAAACTGGTTCCGAGAGGCTGA
TTTTGCTAAAGAAGTGCCTAATTATAAAGCAACTAAAGATGAGAAAATC
GAAGAAATCATCGGTCAAAATGGCGAGCGGATCACCTCAAAGCAAGTTG
ATGATCTTATCGCAAAAGGTAACGGCAAAATTACCCAAGATGAGCTATC
AAAAGTTGTTGATAACTATGAATTGCTCAAACATAGCAAAAATGTGACA

```
AACAGCTTAGATAAGTTAATCTCATCTGTAAGTGCATTTACCTCGTCTA
ATGATTCGAGAAATGTATTAGTGGCTCCAACTTCAATGTTGGATCAAAG
TTTATCTTCTCTTCAATTTGCTAGAGCAGCTTAATTTTTAATGATTGGC
AACTCTATATTGTTTCACACATTATAGAGTTGCCGTTTTATTTTATAAA
AGGAGACAATATGGAAGCTAACCATCAAAGGAATGATCTTGGTTTAGTT
GCCCTCACTATGTTGGCACAATACCATAATATTTCGCTTAATCCGGAA,
set forth in SEQ ID NO: 10,
``` encoding LktA amino acids 731 to 953 (ΔlktA, dotted arrow)

```
ELVITNSKKEKVTIQNWFREADFAKEVPNYKATKDEKIEEIIGQNGERI
TSKQVDDLIAKGNGKITQDELSKVVDNYEGSFNGGDGVDTIDGNDGNDR
LFGGKGDDILDGGNGDDFIDGGKGNDLLHGGKGDDIFVHRKGDVKDLTF
EKVKHNLVITNSKKEKVTIQNWFREADFAKEVPNYKATKDEKIEEIIGQ
NGERITSKQVDDLIAKGNGKITQDELSKVVDNYELLKHSKNVTNSLDKL
ISSVSAFTSSNDSRNVLVAPTSMLDQSLSSLQFARAA*, set forth
in SEQ ID NO: 11.
```

ΔLktA comprises nucleotides encoding the LktA GRR (diagonal bricks) and NE (alternating horizontal dashes).

The *M. haemolytica* ΔlktCAV4 cassette has the nucleotide sequence

```
GAATTCTCTTTTGCTAAATAGTGTTGGTAAGTAGTCCCATTTTGCACAC
CAATCGTTTTCACCTTAGCAAAATCTGTATCTTTTTTCGCAATGAAGGC
AGCAGAGCTTGGAAAGTAAGGCTCGCTAAATAATACTTGTTTCTTACGT
GGTTCCGTAATACCCATACCTGAAATTGCAGCATCAAATTGTTTTTGTT
TTAGGCTTTGGATTAAGCTATCAAAAGGTTGGCTATGGAATGTACAATT
TGCATTCATCTCTTTACAGATAGCATTTGCAATATCCACATCAAAACCG
ATAATTTCTCCCTTCTCTTCGGTCATTTCAAATGGAGGATAGCTTGGCT
CCATCACAAATTTGATATCTTGTGCCTGCGCAGTAACCACACACCCGAA
TAAAAGGGTCAAAAGTGTTTTTTTCATAAAAAGTCCCTGTGTTTTCATT
ATAAGGATTACCACTTTAACGCAGTTACTTTCTTAAAAAAAGTCTTCTT
TTCATAAAGTTTGTTTTATGTCATACAAACACATCAAATTGAGATGTAG
TTTCTCAATCCTCTTGATTCCTCTATCTCAAAAAAACAACCCAAAAGAA
AAAAGAAAAGTATATGTTACATTAATATTACAATGTAATTATTTTGTTT
AATTTCCCTACATTTTGTATAACTTTAAAACACTCCTTTTTCTCTTCTG
ATTATATAAAAGACAAAAAATACAATTTAAGCTACAAAAAACAACAAAA
AACAACAAAAAACACGACAATAAGATCGAGTAATGATTATATTATGTTA
TAATTTTTGACCTAATTTAGAATAATTATAGGAGACATCCCTTATGcaa
ttgGTAATTACAAATAGCAAAAAGAAAAAGTAACAATTCAAATTGGT
TTCGTGAAGCAGATTTCGCTAAAGAAGTTCCAAATTATAAAGCAACGAA
GGATGAAAAAATTGAAGAAATTATTGGACAAAATGGAGAACGTATTACA
AGTAAACAAGTAGATGACTTAATCGCAAAAGGTAACGGAAAAATTACTC
AGGATGAATTATCGAAGGTGGTAGATAACTATGAAggatccTTTAACGG
TGGTGATGGTGTCGATACTATTGACGGTAACGACGGCAATGACCGCTTA
TTTGGTGGTAAAGGCGATGATATTCTCGATGGTGGAAATGGTGATGATT
TTATCGATGGCGGTAAAGGCAACGACCTATTACACGGTGGCAAGGGCGA
TGATATTTTCGTTCACCGTAAAGGCGATGGTAATGATATTATTACCGAT
TCTGACGGCAATGATAAATTATCATTCTCTGATTCGAACTTAAAAGATT
TAACATTTGAAAAAGTTAAACATAATCTTGTCATCACGAATAGCAAAAA
AGAGAAAGTGACCATTCAAAACTGGTTCCGAGAGGCTGATTTTGCTAAA
GAAGTGCCTAATTATAAAGCAACTAAAGATGAGAAAATCGAAGAAATCA
TCGGTCAAAATGGCGAGCGGATCACCTCAAAGCAAGTTGATGATCTTAT
CGCAAAAGGTAACGGCAAAATTACCCAAGATGAGCTATCAAAAGTTGTT
GATAACTATGAATTGCTCAAACATAGCAAAAATGTGACAAACAGCTTAG
ATAAGTTAATCTCATCTGTAAGTGCATTTACCTCGTCTAATGATTCGAG
AAATGTATTAGTGGCTCCAACTTCAATGTTGGATCAAAGTTTATCTTCT
CTTCAATTTGCTAGAGCAGCTTAATTTTTAATGATTGGCAACTCTATAT
TGTTTCACACATTATAGAGTTGCCGTTTTATTTTATAAAAGGAGACAAT
ATGGAAGCTAACCATCAAAGGAATGATCTTGGTTTAGTTGCCCTCACTA
TGTTGGCACAATACCATAATATTTCGCTTAATCCGGAATTC, set
forth in SEQ ID NO: 12.
```

The *M. haemolytica* ΔlktCAV4 cassette encodes the amino acid sequence

```
MQLVITNSKKEKVTIQNWFREADFAKEVPNYKATKDEKIEEIIGQNGER
ITSKQVDDLIAKGNGKITQDELSKVVDNYEGSFNGGDGVDTIDGNDGND
RLFGGKGDDILDGGNGDDFIDGGKGNDLLHGGKGDDIFVHRKGDGNDII
TDSDGNDKLSFSDSNLKDLTFEKVKHNLVITNSKKEKVTIQNWFREADF
AKEVPNYKATKDEKIEEIIGQNGERITSKQVDDLIAKGNGKITQDELSK
VVDNYELLKHSKNVTNSLDKLISSVSAFTSSNDSRNVLVAPTSMLDQSL
SSLQFARAA*, which is set forth in SEQ ID NO: 13.
```

To add a selectable marker and a temperature-sensitive origin of replication, the *M. haemolytica* ΔlktCAV4 cassette was inserted in the plasmid pCT109GA189-Kan. Plasmid pCT109GA189-Kan (described in Briggs, R. E. and Tatum, F. M., 2005, "Generation and Molecular Characterization of New Temperature-Sensitive Plasmids Intended for Genetic Engineering of Pasteurellaceae," Appl. Environ. Microbiol. 71(11): 7187-7195) and plasmid pBCSKlktUp-Down were digested with restriction endonuclease enzyme XbaI, treated with Shrimp alkaline phosphatase, and ligated to each other to generate the replacement plasmid pBCΔlktCAV4-pCT109GA189-Kan.

To generate modified *M. haemolytica* D153 (serotype 1) and *M. haemolytica* D174 (serotype 6) bacteria containing the ΔlktCAV4 cassette, the replacement plasmid pBCΔlktCAV4-pCT109GA189-Kan was introduced into *M. haemolytica* D153 (serotype 1) and *M. haemolytica* D174 (serotype 6) using electroporation as described by Briggs, R. E., et al. ("*Characterization of a Restriction Endonuclease, PhaI, from Pasteurella haemolytica Serotype A1 and Pro-* tection of Heterologous DNA by a cloned Pha I methyltransferase gene," 1994, Appl. Environ. Microbiol. 60(6): 2006-2010) except that the replacement plasmid was not subjected to passage through E. coli strain PhaI Mtase. The two M. haemolytica strains transformed with the replacement plasmid were treated by the steps described in Tatum, F. M. and Briggs R. E. ("Construction of In-Frame aroA Deletion Modifieds of Mannheimia haemolytica, Pasteurella multocida, and Haemophilus somnus by Using a New Temperature-Sensitive Plasmid," 2005, Appl. Environ. Microbiol. 71(11): 7196-7202) to generate the modified M. haemolytica modified products D153ΔlktCAV4 and D174ΔlktCAV4 containing the modified M. haemolytica lktCA cassette. These modified M. haemolytica strains D153ΔlktCAV4 and D174ΔlktCAV4 are useful as vaccine products.

Example 2

Generation of M. bovis Vaccine Product

A polynucleotide fragment encoding an M. bovis Elongation Factor Tu (EF-Tu) and DnaK chimera was inserted into the unique MfeI restriction endonuclease recognition site of the M. haemolytica ΔlktCAV4 cassette to generate ΔlktCAV4Mbovis cassette.

A synthetic polynucleotide fragment encoding an M. bovis EF-Tu/DnaK chimera, having the nucleotide sequence

CAATTGATGAACGCGGTCGATACATGGATTGAGA CACCTGTT

AAAGATTTCGAGAAACCGTTCTTAATGGCGGTAGAAGACGTGTTTACAA

TTTCAGGTCGTGGCACCGTTGCAACAGGTCGTGTAGAACGTGGACGCTT

AAGTTTAAATGAGGAAGTGGAGATTGTAGGTTTAAAGCCCACTAAAAAA

ACAGTCGTTACAGGTATCGAAATGTTTCGCAAAAACTTAAAAGAAGCCC

AAGCAGGAGATAACGCAGGTTTATTATTACGTGGAGTTGAACGCAGTGC

CATTGAACGTGGTCAAGTATTAGCAAAACCAGGGAGTATCGTTCCTCAT

GCCGAATTTGAAGCCGCCATTTATGCATTGACAAAAGAAGAAGGCGGAC

GTCATACTCCGTTTTTCGTAAACTATAAACCTCAATTTTATTTCCGTAC

AACAGATGTGACTGGTGGCCTTGAGTTTGAGAAAGGACGTGAATTTGTA

CAACCGGGAGAAAATGTCAACTTGAAAGTAAAATTAATTGCACCAATCG

CCGTAGAGGAAGGAACAAAATTCAGTATTCGTGAAGGTGGGCGCACAGT

AGGGTATGGTAGTGTAACTAAAATTTTAAAGTTAGTCGATGTAACCCCT

TTAACTTTAGGTATTGAAACAGCAGGCGGCATTGCAACCCCTTTAATCC

CACGTAACACTCGTATTCCCATTACAAAGTCAGAAGTTTTTACAACGTT

TGAAGATAACCAAAGTGAAGTAACAATTCGTATCGTGCAAGGTGAACGT

CCATTAGCGTCTGAAAATAAATTATTAGGACAATTTAACTTAGGTGGAA

TCCGTATCGCACCCCGTGGAGTACCTCAAATCGAAGTCAGTTTCAAAAT

CGATGCAAACGGCATTACGACAGTATTAGCAAAAGATAAAGATACCAAC

AAAGAACAATCTATTACAATTAAAAACAGCTCTAAATTAAGTGACGCAG

AAATCGAAGAAATGATCAAAGATGCAGAAAAAACCGTGAAGCAGATGC

CAAACGTGCCGAAGAAATTAGTACAATTATTCAAGCAGAAAACTTAGTA

AACTCATTAGAAAAGAAATGAACGAAGGTAACATTGTAATTCCAGAAG

AAGAAAAAACTAAAATCGCCGAATATATTAAAGAAGTAAAAGAGTTAAT

CAACAATAAAGATGTAGAACAATTAAAAAAGAAAATTGATGAATTAAAC

GCAGCATATAATATGGCCAAATCAGCAGCAGCCTCAGCAAATAAAGATG

ATAGTAGTAATTCGGATGAAGAAACTTTCGAATTC, set forth in

SEQ ID NO: 18, was synthesized by Blue Heron Biotech (Bothell, Wash., USA). In a 5' to 3' orientation, the synthetic polynucleotide fragment contains nucleotides corresponding to a codon-optimized nucleotide sequence encoding a segment of M. bovis EF-Tu having the nucleotide sequence

ATGAACGCGGTCGATA CATG

GATTGAGACACCTGTTAAAGATTTCGAGAAACCGTTCTTAATGGCGGTA

GAAGACGTGTTTACAATTTCAGGTCGTGGCACCGTTGCAACAGGTCGTG

TAGAACGTGGACGCTTAAGTTTAAATGAGGAAGTGGAGATTGTAGGTTT

AAAGCCCACTAAAAAACAGTCGTTACAGGTATCGAAATGTTTCGCAAA

AACTTAAAAGAAGCCCAAGCAGGAGATAACGCAGGTTTATTATTACGTG

GAGTTGAACGCAGTGCCATTGAACGTGGTCAAGTATTAGCAAAACCAGG

GAGTATCGTTCCTCATGCCGAATTTGAAGCCGCCATTTATGCATTGACA

AAAGAAGAAGGCGGACGTCATACTCCGTTTTTCGTAAACTATAAACCTC

AATTTTATTTCCGTACAACAGATGTGACTGGTGGCCTTGAGTTTGAGAA

AGGACGTGAATTTGTACAACCGGGAGAAAATGTCAACTTGAAAGTAAAA

TTAATTGCACCAATCGCCGTAGAGGAAGGAACAAAATTCAGTATTCGTG

AAGGTGGGCGCACAGTAGGGTATGGTAGTGTAACTAAAATTTTAAAG, set forth in SEQ ID NO: 14, followed by a codon-optimized nucleotide sequence encoding a segment of M. bovis DnaK having the nucleotide sequence

TTAGTCGATGTAACCCCTTTAACTTTAGGTATTGAAACAGCAGGCGGCA

TTGCAACCCCTTTAATCCCACGTAACACTCGTATTCCCATTACAAAGTC

AGAAGTTTTTACAACGTTTGAAGATAACCAAAGTGAAGTAACAATTCGT

ATCGTGCAAGGTGAACGTCCATTAGCGTCTGAAAATAAATTATTAGGAC

AATTTAACTTAGGTGGAATCCGTATCGCACCCCGTGGAGTACCTCAAAT

CGAAGTCAGTTTCAAAATCGATGCAAACGGCATTACGACAGTATTAGCA

AAAGATAAAGATACCAACAAAGAACAATCTATTACAATTAAAAACAGCT

CTAAATTAAGTGACGCAGAAATCGAAGAAATGATCAAAGATGCAGAAAA

AAACCGTGAAGCAGATGCCAAACGTGCCGAAGAAATTAGTACAATTATT

CAAGCAGAAAACTTAGTAAACTCATTAGAAAAGAAATGAACGAAGGTA

ACATTGTAATTCCAGAAGAAGAAAAAACTAAAATCGCCGAATATATTAA

AGAAGTAAAAGAGTTAATCAACAATAAAGATGTAGAACAATTAAAAAAG

AAAATTGATGAATTAAACGCAGCATATAATATGGCCAAATCAGCAGCAG

CCTCAGCAAATAAAGATGATAGTAGTAATTCGGATGAAGAAACTTC, set forth in SEQ ID NO: 16.

The synthetic polynucleotide fragment contains nucleotides corresponding to an MfeI restriction endonuclease recognition site at the 5' end, and nucleotides corresponding to an EcoRI restriction endonuclease recognition site at the 3' end.

The synthetic *M. bovis* EF-Tu/DnaK fragment was digested with MfeI and EcoRI, and inserted into MfeI-digested *M. haemolytica* replacement plasmid pBCΔlktCAV4 to generate plasmid pBCΔlktCAV4Mbovis. The correct orientation of the inserted *M. bovis* EF-Tu/DnaK fragment in the plasmid pBCΔlktCAV4Mbovis was determined using standard Sanger DNA sequencing. The nucleotide sequence of ΔlktCAV4Mbovis, a modified lktCA cassette with the *M. bovis* antigen is GGATCCGAATTCTCTTTTGCTAAATAGTGTTGGTAAGTAGTCCC
ATTTTGCACACCAATCGTTTTCACCTTAGCAAATCTGTATCTTTTTC
GCAATGAAGGCAGCAGAGCTTGGAAAGTAAGGCTCGCTAAATAATACTT
GTTTCTTACGTGGTTCCGTAATACCCATACCTGAAATTGCAGCATCAAA
TTGTTTTTGTTTTAGGCTTTGGATTAAGCTATCAAAAGGTTGGCTATGG
AATGTACAATTTGCATTCATCTCTTTACAGATAGCATTTGCAATATCCA
CATCAAAACCGATAATTTCTCCCTTCTCTTCGGTCATTTCAAATGGAGG
ATAGCTTGGCTCCATCACAAATTTGATATCTTGTGCCTGCGCAGTAACC
ACACACCCGAATAAAAGGGTCAAAAGTGTTTTTTTCATAAAAAGTCCCT
GTGTTTTCATTATAAGGATTACCACTTTAACGCAGTTACTTTCTTAAAA
AAAGTCTTCTTTTCATAAAGTTTGTTTTATGTCATACAAACACATCAAA
TTGAGATGTAGTTTCTCAATCCTCTTGATTCCTCTATCTCAAAAAAACA
ACCCAAAAGAAAAAGAAAAGTATATGTTACATTAATATTACAATGTAA
TTATTTTGTTTAATTTCCCTACATTTTGTATAACTTTAAAACACTCCTT
TTTCTCTTCTGATTATATAAAAGACAAAAAATACAATTTAAGCTACAAA
AAACAACAAAAACAACAAAAAACACGACAATAAGATCGAGTAATGATT
ATATTATGTTATAATTTTTGACCTAATTTAGAATAATTATAGGAGACAT
CCCTTATGcaattgATGAACGCGGTCGATACATGGATTGAGACACCTGT
TAAAGATTTCGAGAAACCGTTCTTAATGGCGGTAGAAGACGTGTTTACA
ATTTCAGGTCGTGGCACCGTTGCAACAGGTCGTGTAGAACGTGGACGCT
TAAGTTTAAATGAGGAAGTGGAGATTGTAGGTTTAAAGCCCACTAAAAA
AACAGTCGTTACAGGTATCGAAATGTTTCGCAAAAACTTAAAAGAAGCC
CAAGCAGGAGATAACGCAGGTTTATTATTACGTGGAGTTGAACGCAGTG
CCATTGAACGTGGTCAAGTATTAGCAAAACCAGGGAGTATCGTTCCTCA
TGCCGAATTTGAAGCCGCCATTTATGCATTGACAAAAGAAGAAGGCGGA
CGTCATACTCCGTTTTTCGTAAACTATAAACCTCAATTTTATTTCCGTA
CAACAGATGTGACTGGTGGCCTTGAGTTTGAGAAAGGACGTGAATTTGT
ACAACCGGGAGAAAATGTCAACTTGAAAGTAAAATTAATTGCACCAATC
GCCGTAGAGGAAGGAACAAAATTCAGTATTCGTGAAGGTGGGCGCACAG
TAGGGTATGGTAGTGTAACTAAAATTTTAAAGTTAGTCGATGTAACCCC
TTTAACTTTAGGTATTGAAACAGCAGGCGGCATTGCAACCCCTTTAATC
CCACGTAACACTCGTATTCCCATTACAAAGTCAGAAGTTTTTACAACGT
TTGAAGATAACCAAAGTGAAGTAACAATTCGTATCGTGCAAGGTGAACG
TCCATTAGCGTCTGAAAATAAATTATTAGGACAATTTAACTTAGGTGGA
ATCCGTATCGCACCCCGTGGAGTACCTCAAATCGAAGTCAGTTTCAAAA
TCGATGCAAACGGCATTACGACAGTATTAGCAAAAGATAAAGATACCAA
CAAAGAACAATCTATTACAATTAAAAACAGCTCTAAATTAAGTGACGCA
GAAATCGAAGAAATGATCAAAGATGCAGAAAAAAACCGTGAAGCAGATG
CCAAACGTGCCGAAGAAATTAGTACAATTATTCAAGCAGAAAACTTAGT
AAACTCATTAGAAAAAGAAATGAACGAAGGTAACATTGTAATTCCAGAA
GAAGAAAAAACTAAAATCGCCGAATATATTAAAGAAGTAAAAGAGTTAA
TCAACAATAAAGATGTAGAACAATTAAAAAAGAAAATTGATGAATTAAA
CGCAGCATATAATATGGCCAAATCAGCAGCAGCCTCAGCAAATAAAGAT
GATAGTAGTAATTCGGATGAAGAAACTTTCgaattgGTAATTACAAATA
GCAAAAAGAAAAAGTAACAATTCAAAATTGGTTTCGTGAAGCAGATTT
CGCTAAAGAAGTTCCAAATTATAAAGCAACGAAGGATGAAAAAATTGAA
GAAATTATTGGACAAAATGGAGAACGTATTACAAGTAAACAAGTAGATG
ACTTAATCGCAAAAGGTAACGGAAAAATTACTCAGGATGAATTATCGAA
GGTGGTAGATAACTATGAAGGATCCTTTAACGGTGGTGATGGTGTCGAT
ACTATTGACGGTAACGACGGCAATGACCGCTTATTTGGTGGTAAAGGCG
ATGATATTCTCGATGGTGGAAATGGTGATGATTTATCGATGGCGGTAA
AGGCAACGACCTATTACACGGTGGCAAGGGCGATGATATTTTCGTTCAC
CGTAAAGGCGATGGTAATGATATTATTACCGATTCTGACGGCAATGATA
AATTATCATTCTCTGATTCGAACTTAAAAGATTTAACATTTGAAAAAGT
TAAACATAATCTTGTCATCACGAATAGCAAAAAAGAGAAAGTGACCATT
CAAAACTGGTTCCGAGAGGCTGATTTTGCTAAAGAAGTGCCTAATTATA
AAGCAACTAAAGATGAGAAAATCGAAGAAATCATCGGTCAAAATGGCGA
GCGGATCACCTCAAAGCAAGTTGATGATCTTATCGCAAAAGGTAACGGC
AAAATTACCCAAGATGAGCTATCAAAAGTTGTTGATAACTATGAATTGC
TCAAACATAGCAAAAATGTGACAAACAGCTTAGATAAGTTAATCTCATC
TGTAAGTGCATTTACCTCGTCTAATGATTCGAGAAATGTATTAGTGGCT
CCAACTTCAATGTTGGATCAAAGTTTATCTTCTCTTCAATTTGCTAGAG
CAGCTTAATTTTTAATGATTGGCAACTCTATATTGTTTCACACATTATA
GAGTTGCCGTTTTATTTTATAAAAGGAGACAATATGGAAGCTAACCATC
AAAGGAATGATCTTGGTTTAGTTGCCCTCACTATGTTGGCACAATACCA
TAATATTTCGCTTAATCCGGAATTC, and is set forth in

SEQ ID NO: 20.

The amino acid sequence of the polypeptide encoded by ΔlktCAV4Mbovis cassette is MQLMNAVDTWIETPVKDFEKPFLMAVEDVFTISGRGTVATGRVERGRLS
LNEEVEIVGLKPTKKTVVTGIEMFRKNLKEAQAGDNAGLLLRGVERSAI
ERGQVLAKPGSIVPHAEFEAAIYALTKEEGGRHTPFFVNYKPQFYFRTT -continued

```
DVTGGLEFEKGREFVQPGENVNLKVKLIAPIAVEEGTKFSIREGGRTVG

YGSVTKILKLVDVTPLTLGIETAGGIATPLIPRNTRIPITKSEVFTTFE

DNQSEVTIRIVQGERPLASENKLLGQFNLGGIRIAPRGVPQIEVSFKID

ANGITTVLAKDKDTNKEQSITIKNSSKLSDAEIEEMIKDAEKNREADAK

RAEEISTIIQAENLVNSLEKEMNEGNIVIPEEEKTKIAEYIKEVKELIN

NKDVEQLKKKIDELNAAYNMAKSAAASANKDDSSNSDEETFELVITNSK

KEKVTIQNWFREADFAKEVPNYKATKDEKIEEIIGQNGERITSKQVDDL

IAKGNGKITQDELSKVVDNYEGSFNGGDGVDTIDGNDGNDRLFGGKGDD

ILDGGNGDDFIDGGKGNDLLHGGKGDDIFVHRKGDGNDIITDSDGNDKL

SFSDSNLKDLTFEKVKHNLVITNSKKEKVTIQNWFREADFAKEVPNYKA

TKDEKIEEIIGQNGERITSKQVDDLDQSLSSLQFARAA*, and set forth in SEQ ID NO: 21.
```

The codon-optimized nucleotide sequence encoding *M. bovis* EF-Tu/DnaK chimera encodes the amino acid sequence

```
QLMNAVDTWIETPVKDFEKPFLMAVEDVFTISGRGTVATGRVERGRLSL

NEEVEIVGLKPTKKTWTGIEMFRKNLKEAQAGDNAGLLLRGVERSAIER

GQVLAKPGSIVPHAEFEAAIYALTKEEGGRHTPFFVNYKPQFYFRTTDV

TGGLEFEKGREFVQPGENVNLKVKLIAPIAVEEGTKFSIREGGRTVGYG

SVTKILKLVDVTPLTLGIETAGGIATPLIPRNTRIPITKSEVFTTFEDN

QSEVTIRIVQGERPLASENKLLGQFNLGGIRIAPRGVPQIEVSFKIDAN

GITTVLAKDKDTNKEQSITIKNSSKLSDAEIEEMIKDAEKNREADAKRA

EEISTIIQAENLVNSLEKEMNEGNIVIPEEEKTKIAEYIKEVKELINNK

DVEQLKKKIDELNAAYNMAKSAAASANKDDSSNSDEETFEF, which is set forth in SEQ ID NO: 19.
```

FIG. 2 depicts a schematic of the construction of the ΔlktCAV4Mbovis cassette from the ΔlktCAV4 cassette. The top portion of the figure shows the *M. haemolytica* ΔlktCAV4 cassette, which contains the lkt promotor (grey arrow); the lktC-lktA intergenic region (white arrow); and lktA nucleotides 2192 to 3022 (ΔlktA, dotted arrow) comprising the inserted synthetic polynucleotide encoding leukotoxin NE (striped slashes); the polynucleotide encoding leukotoxin GRR (diagonal bricks); and the polynucleotide encoding the native NE (alternating horizontal dashes). The polynucleotides encoding EF-Tu and DnaK are depicted above the *M. haemolytica* ΔlktCAV4 cassette. The bottom portion of the figure shows the ΔlktCAV4Mbovis cassette.

To add a selectable marker and a temperature-sensitive origin of replication, plasmids pBCΔlktCAV4Mbovis and pCT109GA189-Kan were digested with restriction endonuclease enzyme XbaI, treated with Shrimp alkaline phosphatase, and ligated to each other to generate the plasmid pBCΔlktCAV4Mbovis-pCT109GA189-Kan. To generate modified *M. haemolytica* D153 (serotype 1) and *M. haemolytica* D174 (serotype 6) containing the ΔlktCAV4Mbovis cassette, the replacement plasmid pBCΔlktCAV4Mbovis-pCT109GA189-Kan was introduced into *M. haemolytica* D153 (serotype 1) and *M. haemolytica* D174 (serotype 6) using electroporation as described in Example 1, above. The two *M. haemolytica* strains transformed with the plasmid containing nucleotides encoding EF-Tu and DnaK were treated by the steps described above in Example 1, to generate D153ΔlktCAV4Mbovis vaccine product and D174ΔlktCAV4Mbovis vaccine product.

Example 3

Cattle Vaccination for *Mycoplasma* Challenge

Calves were vaccinated with a mixture of D153ΔlktCAV4 and D174ΔlktCAV4; or a mixture of ΔlktCAV4Mbovis and D174ΔlktCAV4Mbovis, followed by challenge with *M. bovis* isolate KRB5. After challenge, cattle vaccinated with a mixture of ΔlktCAV4Mbovis and D174ΔlktCAV4Mbovis showed little to no *M. bovis* lung load, while cattle vaccinated with a mixture of D153ΔlktCAV4 and D174ΔlktCAV4 showed a high *M. bovis* lung load.

Twelve Holstein calves, approximately 40 days of age and started on solid feed, were enrolled in the study. The calves had been caught, colostrum deprived, and were isolated in individual hutches until shipment to the USDA's National Animal Disease Center (NADC). Upon arrival the calves were randomly allocated to 2 groups (n=6 per group) housed indoors in a climate-controlled biocontainment facility. Each group was divided among 3 rooms, for a total of 6 rooms, with 2 calves in each room. The calves were fed twice per day calf starter (Calf STARTENA; Purina Mills, Gray Summit, Mo., USA) and hay cubes as much as they would clean up before the next feeding. Fresh water was provided ad libitum.

Six days post arrival (designated day 0) the calves were vaccinated by intranasal instillation of the above experimental vaccine preparations. Group 1 calves received *M. haemolytica* ΔlktCAV4 vaccine product (vaccine without *M. bovis* antigen payload), while Group 2 calves received ΔlktCAV4Mbovis vaccine product (vaccine with *M. bovis* antigen payload).

Serotype 1 and serotype 6 modified-live *M. haemolytica* strains D153ΔlktCAV4 and D174ΔlktCAV4 prepared as in Example 1, and the D153ΔlktCAV4Mbovis and D174ΔlktCAV4Mbovis vaccine products prepared as in Example 2, were grown overnight on Columbia agar plates with 5% defibrinated bovine blood (4 total cultures). Pure culture growth was harvested with DACRON polyester fiber (Du Pont de Nemours and Company, Wilmington, Del., USA) swabs, and each inoculated into 50 mL Columbia broth (in 200 mL Erlenmeyer flasks) until an OD 600 of 0.1 was achieved. The flasks were incubated at 37° C. with shaking at 200 rpm until an OD 600 of approximately 0.4 was achieved, at which point 25 mL of each culture was transferred to a 50 mL conical tube and placed on ice for transport to the animal barn. At the barn, two inocula were formed by combining serotype 1 and serotype 6 of modified-live *M. haemolytica* ΔlktCAV4 and of ΔlktCAV4Mbovis vaccine product. An aliquot of each inoculum was returned to the laboratory for quantitative culture and PCR analysis.

The inoculum with *M. haemolytica* ΔlktCAV4 was determined to contain $3.5 \times 10^8$ CFU/mL for a total dose of $1.4 \times 10^9$ CFU per calf. Twenty representative colonies were tested by PCR and were determined to be evenly divided between *M. haemolytica* serotype 1 and *M. haemolytica* serotype 6. All were confirmed to contain the expected changes in the *M. haemolytica* lktCA gene cluster, and not to contain *M. bovis* insert. The inoculum with ΔlktCAV4Mbovis was determined to contain $3.9 \times 10^8$ CFU/mL for a total dose of $1.6 \times 10^9$ CFU per calf. Nearly two thirds of the inoculum was determined to be serotype 6 and all representative colonies were confirmed to contain the expected changes in the *M. haemolytica* lktCA gene cluster, and to contain the *M. bovis* insert.

Four mL of the vaccine was deposited, 2 mL per nostril, utilizing a MAD NASAL, intranasal mucosal atomization device (Teleflex; Limerick, Pa., USA) attached to a 5 mL disposable syringe. The devices were reused for calves within each room, but new devices were used in each successive room. An aliquot of each challenge inoculum was placed on ice prior to mixing and afterwards for quantitative culture.

Example 4

Challenge with *M. bovis*

This example shows that vaccination with D153ΔlktCAV4Mbovis and D174ΔlktCAV4Mbovis vaccine products protect cattle from *M. bovis* challenge.

All calves were observed twice daily for general health, appetite, and demeanor, for the duration of the experiment. Following *Mycoplasma* challenge an additional daily observation time point was included, for a total of 3 observations per day, which were continued for the remainder of the experiment. Jugular blood (for serum), nasal swabs (for culture, aspirated nasal mucus (for ELISA), tonsil wash specimens (for culture), and tears (for ELISA) were collected weekly. Rectal temperatures were collected 3 times daily following BHV-1 challenge until necropsy.

A two phase challenge system was utilized which employed bovine herpesvirus 1 (BHV-1) pre-challenge in an effort to predispose to virulent *M. bovis* challenge. On day 34 post vaccination all calves were exposed to $10^{8.2}$ total TCID50 BHV-1 Cooper (kindly supplied by National Veterinary Services Laboratories, Ames, Iowa, USA) in a volume of 4 mL (2 mL per nostril) using MAD NASAL devices as above. Four days later all calves were exposed to *M. bovis* isolate KRB5 (kindly supplied by Dr. Karen Register, National Animal Disease Center (NADC); Ames, Iowa, USA). Five mL of the challenge *Mycoplasma* were delivered, 2.5 mL per nostril, using MAD NASAL devices as above.

The KRB5 isolate was recovered in 2014 from pneumonic lung of a Kansas (USA) feedlot calf and identified as *M. bovis* based on colony morphology and species-specific PCR. The isolate was grown for 24 hours at 37° C. in PPLO, selective *Mycoplasma* media (BD Diagnostic Systems; Hunt Valley, Md., USA) supplemented with 10 g/L yeast extract (BD Diagnostic Systems) and 20% horse serum (Life Technologies; Carlsbad, Calif., USA) in a 5% $CO_2$ atmosphere. The resultant bacteria were pelleted by centrifugation at 15,000×g for 20 minutes, followed by resuspension in 1/100th of the original volume in PPLO broth. The suspension was gently passed through a 25-gauge needle, aliquoted, snap-frozen in dry ice/ethanol bath, and stored at −80° C. An aliquot was thawed, serially diluted, and plated on PPLO agar in triplicate to determine bacterial titer. On the day of *M. bovis* challenge an aliquot was thawed and diluted in PPLO broth to achieve a concentration of 2×10⁹ CFU/mL.

A semi-quantitative technique was used for bacterial specimen culture whereby nasal swabs were struck in a consistent manner on the primary zone of blood agar plates, then a sterile loop was used to generate secondary and tertiary zones. Tonsil wash specimens were cultured in a similar manner. The specimens were briefly sonicated, then a sterile swab was dipped and struck as with the nasal swabs. Following overnight incubation, suspect colonies were enumerated, and representative colonies were passed for PCR confirmation of identity and serotype.

With respect to colonization and shedding of vaccine strains, nasal swabs yielded generally little or no *M. haemolytica*. Two out of 6 calves in Group 1 (vaccine with no *M. bovis* payload) yielded *M. haemolytica* serotype 1, serotype 6, or both on day 3, 7 and 21, skipping day 14. Two out of 6 calves in Group 2 (vaccine with *M. bovis* payload) yielded *M. haemolytica* serotype 6 on day 3, and were nasal culture-negative thereafter. All recovered colonies were confirmed by PCR to contain the expected changes in the lktCA gene cluster. Tonsil wash specimens yielded much higher bacterial numbers for a longer period of time. Group 1 calves yielded moderate to high bacterial numbers (numerous colonies in secondary or tertiary zones of the plates) on day 3. Bacterial numbers slowly diminished over successive weeks to become low (isolated colonies in primary zone) to moderate recovery of mixed serotype on Day 35. Only one Group 1 calf ceased shedding at day 35. Group 2 calves yielded similar moderate to high numbers of *M. haemolytica* at day 3, which slowly diminished to low numbers on day 35. Initial recovery was mixed with respect to serotype, but serotype 6 become more prominent over time until only serotype 6 was recovered on day 35. Two Group 2 calves ceased shedding on day 35. All representative isolates were confirmed to contain the expected genetic deletion in the lktCA gene cluster.

Group 1 and Group 2 calves became febrile 3 days following BHV-1 challenge, the highest individual temperature reaching 41.3 C in Group 2 (vaccinated with ΔlktCAV4Mbovis). As seen in FIG. 3, at the time of *Mycoplasma* challenge both groups were febrile. Rectal temperatures generally declined on successive days with an inflection point for Group 1 (vaccinated with ΔlktCAV4) at 10 days post-BHV-1 challenge and Group 2 (vaccinated with ΔlktCAV4Mbovis) at 8 days post-BHV-1 challenge. Starting 8 days post-BHV-1 challenge, and for several days thereafter, Group 2 calves exhibited lower rectal temperatures than did those of Group 1, significantly (P<0.05). A graph of the mean rectal temperature of calves challenged with BHV-1, and four days later challenged with *M. bovis* is depicted on FIG. 3. Results for calves vaccinated with *M. haemolytica* ΔlktCAV4 are labeled Group 1; and results for calves vaccinated with ΔlktCAV4Mbovis vaccine product are labeled Group 2.

Three calves in Group 1 exhibited tachypnea, depression, drooped ears and head-tilt beginning 2 days post-*Mycoplasma* challenge for 2 calves, and beginning 7 days post-*Mycoplasma* challenge for the third. One Group 1 calf exhibited a crusty right eye beginning 12 days after *Mycoplasma* challenge. Some increase in nasal discharge was noted in both groups of calves starting 3 days post-*Mycoplasma* challenge and extending up to 8 days post-challenge.

Three Group 1 calves were euthanized before schedule due to reaching clinical endpoints (July 5, 13 days post-*M. bovis* challenge). Of these calves, one did not exhibit gross lung lesions, while the other two exhibited multifocal lesions involving multiple lobes. While the left middle lobe of one calf showed 50% involvement, the percentage involvement was generally modest. These early-euthanized calves yielded 0.0, 3.7%, and 1.5% lung involvement respectively when lesion volume was multiplied by individual lobe contribution to air exchange. Tympanic bullae from all these calves were filled with purulent to caseous material.

The calves euthanized on-schedule generally showed minor or no lung lesions. Two additional Group 1 calves were found to contain small lesions in one or two lobes totaling 0.05% and 0.03% of total air exchange, while one calf did not show any visible lesions. Tympanic bullae of these 3 Group 1 calves were grossly normal. Group 2 calves fared a bit better with respect to gross lung lesions. Five of 6 showed no visible lesions, while 1 calf evidenced one minor lesion in the right caudal lobe totaling 0.035% of air exchange. One Group 2 calf exhibited unilateral involvement of the tympanic bullae.

Quantitative culture of affected and unaffected lung tissue demonstrated dramatic differences between the calves in Group 1 and Group 2 with respect to infectious *Mycoplasma bovis* lung loading. As seen in FIG. 4, geometric mean *Mycoplasma bovis* recovery from Group 1 lung was $10^{4.2}$ CFU/gram (17000 CFU/gram) in Group 1 whereas geometric mean recovery from Group 2 was $10^{0.32}$ CFU/gram (2 CFU/gram). Six of 6 Group 1 calves yielded culture-positive lung specimens whereas only 2 of 6 Group 2 calves yielded culture-positive lung specimens. Recovery of *M. bovis* from Group 1 calves was compared between individual specimens from lesion vs non-lesion regions. Lesion lung geometric mean titer was $10^{4.4}$ CFU/gram while non-lesion lung was $10^{4.1}$ CFU/gram (P=0.73). A graph of the quantitative *M. bovis* recovery from lung is depicted on FIG. 4. Results for calves vaccinated with M *haemolytica* ΔlktCAV4 are labeled Group 1 and results for calves vaccinated with ΔlktCAV4Mbovis vaccine product are labeled Group 2. Two Group 1 calves yielded *M. bovis* from hock joints; these two calves were not among the calves euthanized early related to symptomatic middle ear disease. No *M. bovis* was recovered from the hocks of Group 2 calves.

Histopathologic findings were generally consistent with gross findings. Examination of lung specimens revealed bronchopneumonia in multiple lobes of 3 Group 1 calves, two of which had been euthanized early due to clinical presentation, and one which was euthanized on-schedule. The remaining three Group 1 calves consistently showed interstitial thickening in all lobes examined without evidence of pneumonia. In Group 2 calves, the minor gross lesion detected in the caudal lobe of a single calf was confirmed to be bronchopneumonia. Three Group 2 calves variably evidenced interstitial thickening without evidence of pneumonia or no significant lesion found. Two Group 2 calves evidenced no significant lesion in any lobe examined.

Examination of tympanic bullae revealed bilateral necrotizing otitis media in three of the six Group 1 calves. The remaining three Group 1 calves showed no significant lesion in tympanic bullae. One Group 2 calf evidenced unilateral necrotizing otitis media with the opposing middle ear (which had appeared grossly normal) exhibiting lymphocytic otitis media. The remaining five Group 2 calves showed no significant lesion in middle ears.

Indirect ELISA was conducted using recombinant *Mycoplasma bovis* EF-Tu produced in *E. coli* and anti-bovine IgG whole molecule secondary antibody. The results are shown in FIG. 5. Group 1 calves exhibited steady low antibody titers until the time of BHV-1 challenge, then trended slightly upwards largely associated with the response of a single calf. Group 2 antibody titers trended upwards throughout the trial, becoming significantly higher (P<0.05) 7 days post vaccination and remaining significantly higher than Group 1 thereafter.

T-test for lung lesion P=0.094; Fisher exact number of involved middle ears P=0.034; Fisher exact number of calves with systemic *Mycoplasma* infection (middle ear or joint) P=0.040; T-test log lung load P=3.3E-07; T-test for rectal temperatures between June 26 and euthanasia P=0.0030.

Mucosal (intranasal) exposure to modified-live *Mannheimia haemolytica* resulted in nasopharyngeal colonization by the organism and a significant systemic immunological response. In this particular trial serotype 6 *Mannheimia haemolytica* colonized to a higher degree than did serotype 1, underscoring the potential importance of combining these serotypes for usage as vaccine vectors to improve the odds of successful colonization and therefore immune response. The antibody response to the *Mycoplasma bovis* antigen payload increased steadily throughout the trial, becoming significantly higher in Group 2 animals when compared to Group 1 (control) animals as early as 7 days post-vaccination. The antibody response to the *Mycoplasma bovis* antigen payload remained higher in Group 2 calves through the remainder of the trial.

BHV-1 viral challenge was utilized to predispose to *Mycoplasma bovis* disease; failure of *Mycoplasma bovis* challenge alone to elicit clinical disease in calves is a frequent problem faced by researchers. BHV-1 is known to elicit a significant febrile response during clinical infection starting on days 3 or 4 following challenge. The current results are consistent with that observation where febrile calves were observed 3 days following BHV-1 challenge. *Mycoplasma* was delivered on day 4 following BHV-1 challenge at the peak of fever. Interestingly, the vaccinated calves recovered more quickly with respect to rectal temperatures. Non-vaccinated calves' rectal temperatures remained elevated longer than did those of vaccinates, significantly higher for the period of 2 weeks prior to euthanasia (P=0.0030). Pneumonic *Mycoplasma* disease in calves is generally associated with mild symptoms with only modest elevation in body temperature, often below 40° C. above which many producers would consider antimicrobial treatment. The more rapid decline in body temperatures of vaccinates are likely a reflection of improved control of *Mycoplasma* infection among vaccinated animals.

Recovery of live *Mycoplasma* from individual lung specimens at post-mortem was strikingly reduced among vaccinates. All non-vaccinated animals yielded multiple lung specimens which contained in excess of 1000 CFU/gram *Mycoplasma bovis* (ranging up to over a million CFU/gram), whereas no vaccinate yielded any lung specimen exceeding 1000 CFU/gram. Four of 6 vaccinates yielded only sterile lung specimens, the other two calves yielded low numbers from one or more lung specimens. Geometric mean lung loading was reduced approximately 1000-fold among vaccinates (P<3.4E-07). It is likely that reduced infectious lung load is associated with reduced risk of lung disease.

Middle ear infection, otitis media, and joint disease are known sequellae of *Mycoplasma bovis* infection. Nevertheless, the relatively high incidence observed in this particular trial is notable. Five of 6 non-vaccinates exhibited either middle ear infection or joint infection while one vaccinate exhibited middle ear infection (P<0.05). Three of the non-vaccinates were euthanized prior to schedule due to symptoms associated with otitis media. It may be that the BHV-1 challenge did predispose to disease as intended with effects which extended to peripheral sites.

Vaccination was associated with reductions in numbers of calves exhibiting lung disease and the percentage involvement of lung. Vaccination was also associated with reductions in numbers of calves exhibiting lung disease and the percentage involvement of lung. With the relatively small group size, however, neither of these reductions were significant at the P<0.05 level. T-test for reduction in lung lesion was P=0.094; Fisher Exact test for numbers of calves with detectable *Mycoplasma* lesions was P=0.12. Given the very large observed difference in infectious lung loading by *Mycoplasma* between vaccinates and non-vaccinates, it is likely that larger experimental groups will yield improved statistical evidence of vaccine efficacy.

Example 5

Identification of Recovered *M. Haemolytica*

Representative isolates of *M. haemolytica* recovered from nasal swabs and from palatine tonsils of calves challenged in Example 4 were positively identified using PCR analyses.

A primer pair spanning the lktCA deletion and inserted synthetic leukotoxin neutralizing epitope, ΔlktCAV4diag, was utilized. The forward diagnostic primer anneals approximately 270 bp upstream of the MfeI site; the reverse diagnostic primer anneals approximately 60 bp downstream of the BamH1 site. The sequence of the forward primer ΔlktCAV4diagF is 5'-gttctcaatcctcttgattcctc-3' and is set forth in SEQ ID NO: 22; the sequence of the reverse primer ΔlktCAV4diagR is 5'-gttaccgtcaatagtatcgacacc-3' and is set forth in SEQ ID NO: 23. Amplification products of 571 base pairs were expected for either *M. haemolytica* serotype 1 or serotype 6 bacteria strain containing the ΔlktCAV4 cassette. Amplification products of 1867 base pairs were expected for either *M. haemolytica* serotype 1 or serotype 6 bacteria strain containing the *M. bovis* insert (ΔlktCAV4Mbovis). Because the expected amplification product from the ΔlktCAV4Mbovis cassette is relatively large, a second primer pair was utilized to assure positive identification. This primer pair was designed to amplify an internal fragment of the synthetic *M. bovis* DNA insert. The sequence of the forward primer MbovispolyF is 5'-ggagaaaatgtcaacttgaaagta-3' and is set forth in SEQ ID NO: 24; the sequence of the reverse primer MbovispolyR is 5'-ggattccacctaagt-taaattgt-3' and is set forth in SEQ ID NO: 25. The expected size of this amplification product is 340 bp and is only produced from *M. haemolytica* carrying the synthetic *M. bovis* insert.

The representative colonies were also subjected to multiplex PCR analysis to determine their capsular type (serotype). Two separate primer pairs were utilized which target biosynthetic genes in the *M. haemolytica* capsular biosynthetic operons of serotype 1 and serotype 6. The sequence of the forward primer MhSt1F is 5'-acaccaaagcaacagactgc-3' and is set forth in SEQ ID NO: 26; the sequence of the reverse primer MhSt1R is 5'-cctgtaaaggcatctgccca-3' and is set forth in SEQ ID NO: 27. This primer pair produces an amplification product of 125 base pairs from only serotype 1 *M. haemolytica*. The sequence of the forward primer MhSt6F is 5'-ttggtgcttgggagtatgcc-3' and is set forth in SEQ ID NO: 27, and the sequence of the reverse primer MhSt6R is 5'-atcggaaacggtttgctgga-3' and is set forth in SEQ ID NO: 28. This primer pair produces an amplification product of 294 base pairs from only serotype 6 *M. haemolytica*.

Example 6

Cattle Vaccination for *Mannheimia* Challenge

Calves were vaccinated with a mixture of D153ΔlktCAV4 and D174ΔlktCAV4; or a mixture of ΔlktCAV4Mbovis and D174ΔlktCAV4Mbovis, followed by challenge with *M. haemolytica* isolate D153. An unvaccinated control group of calves were used for comparison. After challenge, cattle vaccinated with either mixture, with or without an Mbovis payload, showed reduced *M. haemolytica* lung load, reduced gross lung lesions, and reduced mortality, compared to unvaccinated cattle vaccinated which showed high *M. haemolytica* lung load, severe lung lesions, and severe symptoms which warranted euthanasia.

Twenty Holstein calves, approximately 8 weeks of age and started on solid feed, were enrolled in the study. The calves had been caught, colostrum deprived, and were isolated in individual hutches until shipment to the USDA's National Animal Disease Center (NADC). Upon arrival the calves were randomly allocated to 3 groups (one group unvaccinated n=8, and two groups vaccinated n=6 per group) housed indoors in a climate-controlled biocontainment facility. Each group was divided among 3-4 rooms, for a total of 10 rooms, with 2 calves in each room. The calves were fed twice per day calf starter (Calf STARTENA; Purina Mills, Gray Summit, Mo., USA) and hay cubes as much as they would clean up before the next feeding. Fresh water was provided ad libitum.

One week post arrival (designated day 0) the calves were vaccinated by intranasal instillation of the above experimental vaccine preparations. Group 1 calves remained unvaccinated, Group 2 calves received *M. haemolytica* ΔlktCAV4 vaccine product (vaccine without *M. bovis* antigen payload), while Group 3 calves received ΔlktCAV4Mbovis vaccine product (vaccine with *M. bovis* antigen payload).

Serotype 1 and serotype 6 modified-live *M. haemolytica* strains D153ΔlktCAV4 and D174ΔlktCAV4 prepared as in Example 1, and the D153ΔlktCAV4Mbovis and D174ΔlktCAV4Mbovis vaccine products prepared as in Example 2, were grown overnight on Columbia agar plates with 5% defibrinated bovine blood (4 total cultures). Pure culture growth was harvested with DACRON polyester fiber (Du Pont de Nemours and Company; Wilmington, Del., USA) swabs, and each inoculated into 400 mL Columbia broth (in 1 liter Erlenmeyer flasks) until an OD 600 of 0.1 was achieved. The flasks were incubated at 37° C. with shaking at 200 rpm until an OD 600 of approximately 0.65 was achieved, at which point 40 g skim milk powder (Merck 115363) was thoroughly mixed and the cultures were flash-frozen in trays for lyophilization. The lyophilized powders so generated were evaluated by culture to quantitate viable *Mannheimia*. The day of vaccination the lyophilized powders were resuspended in EBSS to produce approximately $2.5 \times 10^8$ CFU/mL for each vaccine strain and the suspensions placed on ice. At the barn, two inocula were formed by combining serotype 1 and serotype 6 of modified-live *M. haemolytica* ΔlktCAV4 and of ΔlktCAV4Mbovis vaccine product. An aliquot of each inoculum was returned to the laboratory for quantitative culture and PCR analysis.

The inoculum with *M. haemolytica* ΔlktCAV4 was determined to contain $2.2 \times 10^8$ CFU/mL for a total dose of $8.8 \times 10^8$ CFU per calf. Twenty representative colonies were tested by PCR and were determined to be evenly divided between *M. haemolytica* serotype 1 and *M. haemolytica* serotype 6. All were confirmed to contain the expected changes in the *M. haemolytica* lktCA gene cluster, and not to contain *M. bovis* insert. The inoculum with ΔlktCAV4Mbovis was determined to contain $3.0 \times 10^8$ CFU/mL for a total dose of $1.2 \times 10^9$ CFU per calf. The inoculum was determined to be evenly divided between *M. haemolytica* serotype 1 and *M. haemolytica* serotype 6 and all representative colonies were confirmed to contain the expected changes in the *M. haemolytica* lktCA gene cluster, and to contain the *M. bovis* insert.

Four mL of the vaccine was deposited, 2 mL per nostril, utilizing a MAD NASAL, intranasal mucosal atomization device (Teleflex; Limerick, Pa., USA) attached to a 5 mL disposable syringe. The devices were reused for calves within each room, but new devices were used in each successive room. An aliquot of each challenge inoculum was placed on ice prior to mixing and afterwards for quantitative culture.

Example 7

Challenge with *M. haemolytica*

This example shows that vaccination with D153ΔlktCAV4, D174ΔlktCAV4, D153ΔlktCAV4Mbovis, and D174ΔlktCAV4Mbovis vaccine products protect cattle from *M. haemolytica* challenge.

All calves were observed twice daily for general health, appetite, and demeanor, for the duration of the experiment. Following *Mannheimia* challenge an additional daily observation time point was included, for a total of 3 observations per day, which were continued for the remainder of the experiment. Jugular blood (for serum), nasal swabs (for culture), and tears (for ELISA) were collected weekly. Rectal temperatures were collected twice daily following virulent *Mannheimia* challenge until necropsy.

An intratracheal challenge system was utilized over a span of 3 days where a subset of each group was challenged on any given day. A stock of lung homogenate was grown overnight on Columbia Blood Agar +5% bovine blood. *Mannheimia* growth was harvested then diluted in EBSS to create a stock at an OD600=0.6. For each calf, 1.25 mL stock diluted in 100 mL EBSS was administered for challenge followed by 100 mL sterile EBSS. *Mannheimia* was used unwashed, all preparations were kept on ice prior to animal inoculation. Administration utilized an 18-gauge hypodermic needle inserted into the tracheal lumen. This procedure was repeated for all three challenge days whereby 2 calves of each group were challenged on days 29 and 30, and the remaining calves (a total of 8 calves including 4 controls) were challenged on day 30. Challenge dose was quantitated each day of preparation.

A semi-quantitative technique was used for bacterial specimen culture whereby nasal swabs were struck in a consistent manner on the primary zone of blood agar plates, then a sterile swab was used to generate secondary and tertiary zones. Following overnight incubation, suspect colonies were enumerated, and representative colonies were passed for PCR confirmation of identity and serotype.

With respect to colonization and shedding of vaccine strains, both serotypes of the vaccine strains were detected in nasal swab specimens in the two vaccinated groups (Group 2 and Group 3). Recovery of the vaccine strains was high initially and progressively waned throughout the 4 weeks vaccination phase. Vaccine strains were still detected in 2 of 3 rooms for each of the vaccinated groups at the time of challenge. No adverse reactions were observed in the vaccinated calves. No *Mannheimia* were detected in the unvaccinated group prior to challenge (Group 1). All representative isolates were confirmed to contain the expected genetic deletion in the lktCA gene cluster.

*Mannheimia* recovery from nasal swabs following vaccination. Numbers of culture-positive animals and semi-quantitative shedding score are shown on Table 2, below.

| | Days after vaccination | | | | | | | |
|---|---|---|---|---|---|---|---|---|
| | D-5 | D0 | D1 | D3 | D7 | D14 | D21 | D28 |
| Control | 0/8 | 0/8 | NS | 0/8 | 0/8 | 0/8 | 0/8 | 0/8 |
| LktV4 | 0/6 | 0/6 | 6/6 | 6/6 | 3/6 | 2/6 | 2/6 | 2/6 |
| | | | 14+ | 7.5+ | 6.0+ | 3.5+ | 4.0+ | 1.0+ |
| LktV4 Mb | 0/6 | 0/6 | 6/6 | 6/6 | 4/6 | 2/6 | 2/6 | 2/6 |
| | | | 15+ | 6.0+ | 5.0+ | 4.5+ | 4.5+ | 5.0+ |

Following challenge, unvaccinated Group 1 calves exhibited a steady rise in rectal temperatures until mortality or euthanasia. In contrast to unvaccinated calves, the vaccinated Group 2 and Group 3 calves exhibited an early rise in rectal temperature within hours of challenge which then declined on successive days.

All 12 vaccinated calves survived to scheduled euthanasia 3 days after challenge. In the unvaccinated control group (Group 1) 2 of 8 calves reached clinical endpoints which warranted euthanasia prior to schedule, 4 succumbed to pneumonia prior to schedule, and only 2 survived to scheduled euthanasia. Seven of 8 Group 1 calves exhibited depression, tachypnea, and anorexia. In general, the vaccinated calves remained alert and feeding, though feed intake was reduced the day following challenge. One vaccinated calf exhibited tachypnea 2 days following challenge.

Heavy growth of the challenge strain of *Mannheimia* was recovered from liver tissue and tracheal swab specimens of all unvaccinated Group 1 calves. Seven of 8 Group 1 calves also yielded heavy growth from spleen specimens. No growth was observed from liver or spleen specimens of Group 2 vaccinates (ΔlktCAV4 vaccine), and light growth was observed from 1 of 6 tracheal swab specimens in this group. Group 3 (ΔlktCAV4Mbovis vaccine) calves yielded light growth from 2 of 6 spleen swabs and 1 of 6 liver swabs. Light growth was also observed from tracheal swab specimens of Group 3.

Total lung lesion volume, corrected for the air exchange contribution of each lung lobe, was significantly higher in the unvaccinated Group 1. An average of 49.7% of unvaccinated Group 1 calf lung was visibly damaged compared to an average of 8.2% damage in Group 2 vaccinates and 17.3% in Group 3 vaccinates. All Group 1 calves exhibited extensive fibrinous consolidation with numerous pleural adhesions, including 6 calves which exhibited pleural effusion. One Group 2 calf exhibited a single pleural adhesion, and 2 Group 3 calves exhibited multiple pleural adhesions. The lung lesions were significantly reduced, P<0.000001 comparing Group 2 with Group 1, and P<0.001 comparing Group 3 with Group 1, based on two-tailed Student's t-test. Group 2 did not statistically differ from Group 3, P>0.25.

Quantitative culture of affected and unaffected lung tissue demonstrated a reduction in infectious bacterial load in both vaccinated Group 2 and Group 3 calves compared to unvaccinated Group 1 control calves. All lobes tested from Group 1 were culture positive for *Mannheimia* with a geometric mean load of $6.2 \times 10^9$ CFU recovered per gram of lung tissue. In vaccinated Group 2 (no *M. bovis* payload), 17 of 30 lung specimens were culture positive for *Mannheimia* with a geometric mean load of $2.8 \times 10^4$ CFU/gram of lung tissue. In vaccinated Group 3 (plus *M. bovis* payload), 25 of 30 lung specimens were culture positive for *Mannheimia* with a geometric mean load of $2.4 \times 10^6$ CFU/gram of lung tissue.

Indirect ELISA was conducted using *Mannheimia* whole cell antigen and secondary antibodies anti-bovine IgG1 and anti-bovine IgG2 for serum specimens or anti-bovine IgG whole molecule and anti-bovine IgA for tear secretion specimens. The IgG1 *Mannheimia* titers in serum from calves challenged with *Mannheamia* are shown in FIG. 6. The IgG2 *Mannheimia* titers in serum from calves challenged with *Mannheamia* are shown in FIG. 7. The IgG *Mannheimia* titers in tear secretions from calves challenged with *Mannheamia* are shown in FIG. 8. The IgA *Mannheimia* titers in tear secretions from calves challenged with *Mannheamia* are shown in FIG. 9. These results show that Group 1 calves exhibited low and relatively steady serum and tear secretion titers throughout the trial. Calves from Groups 2 and 3 exhibited increased IgG1 and IgG2 serum titers within 2 weeks of vaccination which continued to rise throughout the trial. These vaccinated groups also exhibited increased mucosal antibody titers in tear secretions, both IgG and IgA, within 1 week of vaccination.

We claim:

1. An *M. bovis* antigen comprising elongation factor thermos-unstable protein (EF-Tu) and a heat shock protein DnaK chimera.

2. A composition comprising the *M. bovis* antigen of claim 1, wherein the composition is an *M bovis* antigen polypeptide, a vaccine, or an immunogenic composition.

3. A method for provoking an immune response in an animal, the method comprising administering to the animal at least one effective dose of a composition of claim 2.

4. The composition of claim 2, further comprising a pharmaceutically-acceptable carrier or adjuvant.

5. The method of claim 3, wherein the animal is cattle, sheep, goats, pigs, bison, elk, camels, dogs, or deer.

* * * * *